US012605399B2

(12) United States Patent
Dias et al.

(10) Patent No.: US 12,605,399 B2
(45) Date of Patent: Apr. 21, 2026

(54) COMPOSITIONS FOR CFTR MRNA THERAPY

(71) Applicant: TRANSLATE BIO, INC., Waltham, MA (US)

(72) Inventors: Anusha Dias, Cambridge, MA (US); Khang Anh Tran, Cambridge, MA (US); Lianne Boeglin, Cambridge, MA (US); Frank Derosa, Cambridge, MA (US); John Androsavich, Cambridge, MA (US); Shraddha Sharma, Cambridge, MA (US); Gang Sun, Cambridge, MA (US); Neha Kaushal, Cambridge, MA (US); Shrirang Karve, Cambridge, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 706 days.

(21) Appl. No.: 17/923,470

(22) PCT Filed: May 7, 2021

(86) PCT No.: PCT/US2021/031313
§ 371 (c)(1),
(2) Date: Nov. 4, 2022

(87) PCT Pub. No.: WO2021/226468
PCT Pub. Date: Nov. 11, 2021

(65) Prior Publication Data
US 2023/0181619 A1      Jun. 15, 2023

Related U.S. Application Data

(60) Provisional application No. 63/111,308, filed on Nov. 9, 2020, provisional application No. 63/021,327, filed on May 7, 2020.

(51) Int. Cl.
*A61K 31/7105*     (2006.01)
*A61K 9/00*     (2006.01)
*A61K 9/1271*     (2025.01)
*A61K 31/47*     (2006.01)
*A61P 11/00*     (2006.01)

(52) U.S. Cl.
CPC ........ *A61K 31/7105* (2013.01); *A61K 9/0078* (2013.01); *A61K 9/1271* (2013.01); *A61K 31/47* (2013.01); *A61P 11/00* (2018.01)

(58) Field of Classification Search
None
See application file for complete search history.

(56) References Cited

U.S. PATENT DOCUMENTS

| | | |
|---|---|---|
| 4,737,323 A | 4/1988 | Martin et al. |
| 5,171,678 A | 12/1992 | Behr et al. |
| 5,334,761 A | 8/1994 | Gebeyehu et al. |
| 5,744,335 A | 4/1998 | Wolff et al. |
| 5,885,613 A | 3/1999 | Holland et al. |
| 2011/0081708 A1 | 4/2011 | Liu et al. |
| 2012/0195936 A1 | 8/2012 | Rudolph et al. |
| 2015/0376220 A1 | 12/2015 | DeRosa et al. |
| 2016/0032356 A1 | 2/2016 | Heartlein et al. |
| 2016/0040154 A1 | 2/2016 | Heartlein et al. |

FOREIGN PATENT DOCUMENTS

| | | |
|---|---|---|
| WO | WO 2005/121348 A1 | 12/2005 |
| WO | WO 2010/042877 A1 | 4/2010 |
| WO | WO 2010/053572 A2 | 5/2010 |
| WO | WO 2010/144740 A1 | 12/2010 |
| WO | WO 2011/012316 A2 | 2/2011 |
| WO | WO 2012/170889 A1 | 12/2012 |
| WO | WO 2013/063468 A1 | 5/2013 |
| WO | WO 2013/149140 A1 | 10/2013 |
| WO | WO 2015/061467 A1 | 4/2015 |
| WO | WO 2015/095340 A1 | 6/2015 |
| WO | WO 2015/184256 A2 | 12/2015 |
| WO | WO 2015/199952 A1 | 12/2015 |
| WO | WO 2016/004202 A1 | 1/2016 |
| WO | WO 2016/004318 A1 | 1/2016 |
| WO | WO 2016/118724 A1 | 7/2016 |
| WO | WO 2016/118725 A1 | 7/2016 |
| WO | WO 2016/205691 A1 | 12/2016 |
| WO | WO 2017/004143 A1 | 1/2017 |
| WO | WO 2017/049245 A2 | 3/2017 |
| WO | WO 2017/066573 A1 | 4/2017 |
| WO | WO 2017/075531 A1 | 5/2017 |
| WO | WO 2017/117528 A1 | 7/2017 |
| WO | WO 2017/173054 A1 | 10/2017 |
| WO | WO 2018/089790 A1 | 5/2018 |
| WO | WO 2018/089801 A1 | 5/2018 |
| WO | WO 2018/104385 A1 | 6/2018 |

(Continued)

OTHER PUBLICATIONS

Sequence alignment—SEQ ID No. 2, 2025.*
Sequence alignment—SEQ ID No. 3, 2025.*
Sequence alignment_Dias—SEQ ID No. 2, 2025.*
Alton et al., "Cationic lipid-mediated CFTR gene transfer to the lungs and nose of patients with cystic fibrosis: a double-blind placebo-controlled trial," Lancet, vol. 353, Issue 9157, pp. 947-954 (1999).

(Continued)

*Primary Examiner* — Ileana Popa

(74) *Attorney, Agent, or Firm* — LATHROP GPM LLP; James H. Velema, Esq.

(57) ABSTRACT

The present invention provides, among other things, improved methods and pharmaceutical compositions for treating cystic fibrosis based on codon optimized mRNA encoding a wild-type Cystic Fibrosis Transmembrane Conductance Regulator (CFTR) protein.

20 Claims, 24 Drawing Sheets

Specification includes a Sequence Listing.

(56)                    References Cited

FOREIGN PATENT DOCUMENTS

| WO | WO 2018/157133 A1 | 8/2018 |
| WO | WO 2018/157141 A1 | 8/2018 |
| WO | WO 2018/157154 A2 | 8/2018 |
| WO | WO 2018/213476 A1 | 11/2018 |
| WO | WO 2019/207060 A1 | 10/2019 |
| WO | WO 2019/222424 A1 | 11/2019 |
| WO | WO 2020/047061 A1 | 3/2020 |
| WO | WO 2020/097384 A1 | 5/2020 |
| WO | WO 2021/055609 A1 | 3/2021 |

OTHER PUBLICATIONS

Alton et al., "A randomised, double-blind, placebo-controlled trial of repeated nebulisation of non-viral cystic fibrosis transmembrane conductance regulator (CFTR) gene therapy in patients with cystic fibrosis", National Institute for Health Research, vol. 3, Issue 5, (2016), (240 pages).

Behr et al., "Efficient gene transfer into mammalian primary endocrine cells with lipopolyamine-coated DNA", Proc. Natl. Acad. Sci. USA, vol. 86, Sep. 1989, pp. 6982-6986, (5 pages).

Bloomfield, Victor A., "Quasi-Elastic Light Scattering Applications in Biochemistry and Biology", Ann. Rev. Biophys. Bioeng., vol. 10, 1981, pp. 421-450, (30 pages).

Budker et al., "Protein/amphipathic polyamine complexes enable highly efficient transfection with minimal toxicity", Biotechniques, vol. 23, No. 1, 1997, pp. 139-147, DOI: 10.2144/97231rr02, (8 pages).

Conese et al., "Gene and cell therapy for cystic fibrosis: From bench to bedside," J. Cyst. Fibros., vol. 10, Suppl 2, pp. S114-S128(2011).

Costa et al., "Fusion tags for protein solubility, purification, and immunogenicity in *Escherichia coli*: the novel Fh8 system", Front. Microbiol., vol. 5, 2014, Article No. 63, DOI: 10.3389/fmicb.2014. 00063, (20 pages).

Gao et al., "A Novel Cationic Liposome Reagent for Efficient Transfection of Mammalian Cells", Biochemical and Biophysical Research Communications, vol. 179, No. 1, 1991, pp. 280-285, (6 pages).

Heyes et al., "Cationic lipid saturation influences intracellular delivery of encapsulated nucleic acids", Journal of Controlled Release, vol. 107, 2005, pp. 276-287, (12 pages).

International Search Report and Written Opinion for PCT/US21/31313, dated Oct. 18, 2021. 13 pages.

Kasuya et al., "In Delivery of Bionanocapsules Phaseolus vulgaris Agglutinin-L4 Isolectin to Malignant Tumors Overexpressing N-Acetylglucosaminyltransferase V", Human Gene Therapy, vol. 19, No. 9, 2008, pp. 887-895, DOI: 10.1089/hum.2008.037, (9 pages).

Klibanov et al., "Amphipathic polyethyleneglycols effectively prolong the circulation time of liposomes", FEBS Letters, vol. 268, No. 1, 1990, pp. 235-237, (3 pages).

Lasic, Dan D., "Novel applications of liposomes", Trends in Biotechnology, vol. 16, No. 7, 1998, pp. 307-321, DOI: 10.1016/S0167-7799(98)01220-7, (15 pages).

Lasic et al., "Gelation of liposome interior", FEBS Letters, vol. 312, No. 2, 1992, pp. 255-258, (4 pages).

Mauro, "Codon Optimization in the Production of Recombinant Biotherapeutics: Potential Risks and Considerations", Biodrugs, vol. 32, No. 1, Feb. 1, 2018 (Feb. 1, 2018), pp. 69-81.

Mauro et al., "A critical analysis of codon optimization in human therapeutics", Trends in Molecular Medicine, vol. 20, No. 11, 2014, pp. 604-613, (10 pages).

McClellan et al., "Genetic Heterogeneity in Human Disease", Cell, vol. 141, No. 2, 2010, pp. 210-217, DOI: 10.1016/j.cell.2010.03. 032, (8 pages).

Morrissey et al., "Potent and persistent in vivo anti-HBV activity of chemically modified siRNAs", Nature Biotechnology, vol. 23, No. 8, 2005, pp. 1003-1007, (6 pages).

Pearson, "One gene, twenty years: when the cystic fibrosis gene was found in 1989, therapy seemed around the corner. Two decades on, biologists still have a long way to go," Nature, vol. 460, Issue 7252, pp. 164-169 (2009).

Plotkin et al., "Synonymous but not the same: the causes and consequences of codon bias", Nature Reviews Genetics, Nature Publishing Group, GB, vol. 12, No. 1, Jan. 1, 2011 (Jan. 1, 2011), pp. 32-42.

Rosenecker et al., "Interaction of bronchoalveolar lavage fluid with polyplexes and lipoplexes: analysing the role of proteins and glycoproteins," J Gene Med., vol. 5, Issue 1, pp. 49-60 (2003).

Rosenecker et al., "Gene therapy for cystic fibrosis lung disease: Current status and future Perspectives," Curr. Opin. Mol. Ther., vol. 8, No. 5, pp. 439-445 (2006).

Rowe et al., "Mechanisms of Disease: Cystic Fibrosis," New Engl. J. Med., vol. 352, pp. 1992-2001 (2005).

Semple et al., "Rational design of cationic lipids for siRNA delivery", Nature Biotechnology, vol. 28, No. 2, 2010, pp. 172-176, (7 pages).

Sharp et al., "The codon adaptation index—a measure of directional synonymous codon usage bias, and its potential applications", Nucleic Acids Research, vol. 15, No. 3, 1987, pp. 1281-1295, (15 pages).

Villalobos et al., "Gene Designer: a synthetic biology tool for constructing artificial DNA segments", BMC Bioinformatics, Biomed Central, London, GB, vol. 7, No. 1, Jun. 6, 2006 (Jun. 6, 2006), pp. 1-8.

Whitehead et al., "Degradable lipid nanoparticles with predictable in vivo siRNA delivery activity", Nature Communication, vol. 5, 2014, Article No. 4277, DOI: 10.1038/ncomms5277, (10 pages).

* cited by examiner

List of codon-optimized
nucleotide sequences

Motif Screen

GC content
analysis

Codon Adaptation
Index (CAI) analysis

Updated list of
optimized nucleotide
sequences

Low Resolution

Medium Resolution

Saline control                    mRNA in LNP

High Resolution

Saline mRNA in LNP mRNA in LNP

ALI Culture

ALI Culture Timeline

ALI Culture

ROC For HBEC Screening

Similar Results Obtained with Mouse &
Human Lung Homogenates

| mouse lung S9 $T_{1/2}$ (hr) | human lung S9 $T_{1/2}$ (hr) |
|---|---|
| 4.5 | 3.6 |

COMPOSITIONS FOR CFTR MRNA THERAPY

CROSS-REFERENCE TO RELATED APPLICATIONS

This application is a 35 U.S.C. § 371 National Stage Application of International Application No. PCT/US2021/031313, filed on May 7, 2021, which benefit of, and priority to, U.S. Provisional Patent Ser. No. 63/021,327, filed on May 7, 2020, and U.S. Provisional Application Ser. No. 63/111,308, filed on Nov. 9, 2020. The contents of each of the foregoing applications are hereby incorporated by reference in their entireties.

SEQUENCE LISTING

The present specification makes reference to a Sequence Listing (submitted electronically as a .txt file named "MRT-2175WO_ST25" on May 7, 2021). The .txt file was generated on May 7, 2021 and is 91 KB in size. The entire contents of the sequence listing are herein incorporated by reference.

BACKGROUND

Cystic fibrosis is an autosomal inherited disorder resulting from mutation of the CFTR gene, which encodes a chloride ion channel believed to be involved in regulation of multiple other ion channels and transport systems in epithelial cells. Loss of function of CFTR results in chronic lung disease, aberrant mucus production, and dramatically reduced life expectancy. See generally Rowe et al., New Engl. J. Med. 352, 1992-2001 (2005).

Currently there is no cure for cystic fibrosis. The literature has documented numerous difficulties encountered in attempting to induce expression of CFTR in the lung. For example, viral vectors comprising CFTR DNA triggered immune responses and CF symptoms persisted after administration. Conese et al., J. Cyst. Fibros. 10 Suppl 2, S114-28 (2011); Rosenecker et al., Curr. Opin. Mol. Ther. 8, 439-45 (2006). Non-viral delivery of DNA, including CFTR DNA, has also been reported to trigger immune responses. Alton et al., Lancet 353, 947-54 (1999); Rosenecker et al., J Gene Med. 5, 49-60 (2003). Furthermore, non-viral DNA vectors encounter the additional problem that the machinery of the nuclear pore complex does not ordinarily import DNA into the nucleus, where transcription would occur. Pearson, Nature 460, 164-69 (2009).

SUMMARY OF THE INVENTION

The present invention provides, among other things, pharmaceutical compositions comprising messenger RNA (mRNA) encoding a Cystic Fibrosis Transmembrane Conductance Regulator (CFTR) protein and methods of making and using thereof. Notably, mRNAs encoding CFTR proteins described herein are codon-optimized using a new algorithm and exhibit an increased CFTR protein expression and activity level. Furthermore, cationic lipids described herein exhibit increased potency for pulmonary delivery and increased CFTR expression. These pharmaceutical compositions can be used for improved treatment of cystic fibrosis.

In one aspect, the present invention provides a codon-optimized mRNA molecule comprising a coding sequence encoding Cystic Fibrosis Transmembrane Conductance Regulator (CFTR) protein, wherein the coding sequence encodes the amino acid sequence of SEQ ID NO: 1 and the coding sequence is at least 85% identical to SEQ ID NO: 2 or SEQ ID NO: 3.

In some embodiments, a codon-optimized mRNA molecule is at least 85% identical to SEQ ID NO: 2. In some embodiments, a codon-optimized mRNA molecule is at least 90% identical to SEQ ID NO: 2. In some embodiments, a codon-optimized mRNA molecule is at least 92% identical to SEQ ID NO: 2. In some embodiments, a codon-optimized mRNA molecule is at least 95% identical to SEQ ID NO: 2. In some embodiments, a codon-optimized mRNA molecule is at least 96% identical to SEQ ID NO: 2. In some embodiments, a codon-optimized mRNA molecule is at least 97% identical to SEQ ID NO: 2. In some embodiments, a codon-optimized mRNA molecule is at least 98% identical to SEQ ID NO: 2. In some embodiments, a codon-optimized mRNA molecule is at least 99% identical to SEQ ID NO: 2. In some embodiments, a codon-optimized mRNA molecule is identical to SEQ ID NO: 2.

In some embodiments, a codon-optimized mRNA molecule is at least 85% identical to SEQ ID NO: 3. In some embodiments, a codon-optimized mRNA molecule is at least 90% identical to SEQ ID NO: 3. In some embodiments, a codon-optimized mRNA molecule is at least 92% identical to SEQ ID NO: 3. In some embodiments, a codon-optimized mRNA molecule is at least 95% identical to SEQ ID NO: 3. In some embodiments, a codon-optimized mRNA molecule is at least 96% identical to SEQ ID NO: 3. In some embodiments, a codon-optimized mRNA molecule is at least 97% identical to SEQ ID NO: 3. In some embodiments, a codon-optimized mRNA molecule is at least 98% identical to SEQ ID NO: 3. In some embodiments, a codon-optimized mRNA molecule is at least 99% identical to SEQ ID NO: 3. In some embodiments, a codon-optimized mRNA molecule is identical to SEQ ID NO: 3.

In some embodiments, a codon-optimized mRNA molecule is at least 85% identical to SEQ ID NO: 4. In some embodiments, a codon-optimized mRNA molecule is at least 90% identical to SEQ ID NO: 4. In some embodiments, a codon-optimized mRNA molecule is at least 92% identical to SEQ ID NO: 4. In some embodiments, a codon-optimized mRNA molecule is at least 95% identical to SEQ ID NO: 4. In some embodiments, a codon-optimized mRNA molecule is at least 96% identical to SEQ ID NO: 4. In some embodiments, a codon-optimized mRNA molecule is at least 97% identical to SEQ ID NO: 4. In some embodiments, a codon-optimized mRNA molecule is at least 98% identical to SEQ ID NO: 4. In some embodiments, a codon-optimized mRNA molecule is at least 99% identical to SEQ ID NO: 4. In some embodiments, a codon-optimized mRNA molecule is identical to SEQ ID NO: 4.

In some embodiments, a codon-optimized mRNA molecule is at least 85% identical to SEQ ID NO: 5. In some embodiments, a codon-optimized mRNA molecule is at least 90% identical to SEQ ID NO: 5. In some embodiments, a codon-optimized mRNA molecule is at least 92% identical to SEQ ID NO: 5. In some embodiments, a codon-optimized mRNA molecule is at least 95% identical to SEQ ID NO: 5. In some embodiments, a codon-optimized mRNA molecule is at least 96% identical to SEQ ID NO: 5. mRNA molecule In some embodiments, a codon-optimized mRNA molecule is at least 98% identical to SEQ ID NO: 5. In some embodiments, a codon-optimized mRNA molecule is at least 99% identical to SEQ ID NO: 5. In some embodiments, a codon-optimized mRNA molecule is identical to SEQ ID NO: 5.

In some embodiments, a codon-optimized mRNA molecule is at least 85% identical to SEQ ID NO: 6. In some embodiments, a codon-optimized mRNA molecule is at least 90% identical to SEQ ID NO: 6. In some embodiments, a codon-optimized mRNA molecule is at least 92% identical to SEQ ID NO: 6. In some embodiments, a codon-optimized mRNA molecule is at least 95% identical to SEQ ID NO: 6. In some embodiments, a codon-optimized mRNA molecule is at least 96% identical to SEQ ID NO: 6. In some embodiments, a codon-optimized mRNA molecule is at least 97% identical to SEQ ID NO: 6. In some embodiments, a codon-optimized mRNA molecule is at least 98% identical to SEQ ID NO: 6. In some embodiments, a codon-optimized mRNA molecule is at least 99% identical to SEQ ID NO: 6. In some embodiments, a codon-optimized mRNA molecule is identical to SEQ ID NO: 6.

In some embodiments, a codon-optimized mRNA molecule is at least 85% identical to SEQ ID NO: 7. In some embodiments, a codon-optimized mRNA molecule is at least 90% identical to SEQ ID NO: 7. In some embodiments, a codon-optimized mRNA molecule is at least 92% identical to SEQ ID NO: 7. In some embodiments, a codon-optimized mRNA molecule is at least 95% identical to SEQ ID NO: 7. In some embodiments, a codon-optimized mRNA molecule is at least 96% identical to SEQ ID NO: 7. In some embodiments, a codon-optimized mRNA molecule is at least 97% identical to SEQ ID NO: 7. In some embodiments, a codon-optimized mRNA molecule is at least 98% identical to SEQ ID NO: 7. In some embodiments, a codon-optimized mRNA molecule is at least 99% identical to SEQ ID NO: 7. In some embodiments, a codon-optimized mRNA molecule is identical to SEQ ID NO: 7.

In some embodiments, a codon-optimized mRNA molecule is at least 85% identical to SEQ ID NO: 8. In some embodiments, a codon-optimized mRNA molecule is at least 90% identical to SEQ ID NO: 8. In some embodiments, a codon-optimized mRNA molecule is at least 92% identical to SEQ ID NO: 8. In some embodiments, a codon-optimized mRNA molecule is at least 95% identical to SEQ ID NO: 8. In some embodiments, a codon-optimized mRNA molecule is at least 96% identical to SEQ ID NO: 8. In some embodiments, a codon-optimized mRNA molecule is at least 97% identical to SEQ ID NO: 8. In some embodiments, a codon-optimized mRNA molecule is at least 98% identical to SEQ ID NO: 8. In some embodiments, a codon-optimized mRNA molecule is at least 99% identical to SEQ ID NO: 8. In some embodiments, a codon-optimized mRNA molecule is identical to SEQ ID NO: 8.

In some embodiments, a codon-optimized mRNA molecule is at least 85% identical to SEQ ID NO: 9. In some embodiments, a codon-optimized mRNA molecule is at least 90% identical to SEQ ID NO: 9. In some embodiments, a codon-optimized mRNA molecule is at least 92% identical to SEQ ID NO: 9. In some embodiments, a codon-optimized mRNA molecule is at least 95% identical to SEQ ID NO: 9. In some embodiments, a codon-optimized mRNA molecule is at least 96% identical to SEQ ID NO: 9. In some embodiments, a codon-optimized mRNA molecule is at least 97% identical to SEQ ID NO: 9. mRNA molecule In some embodiments, a codon-optimized mRNA molecule is at least 99% identical to SEQ ID NO: 9. In some embodiments, a codon-optimized mRNA molecule is identical to SEQ ID NO: 9.

In some embodiments, a codon-optimized mRNA molecule is at least 85% identical to SEQ ID NO: 10. In some embodiments, a codon-optimized mRNA molecule is at least 90% identical to SEQ ID NO: 10. In some embodiments, a codon-optimized mRNA molecule is at least 92% identical to SEQ ID NO: 10. In some embodiments, a codon-optimized mRNA molecule is at least 95% identical to SEQ ID NO: 10. In some embodiments, a codon-optimized mRNA molecule is at least 96% identical to SEQ ID NO: 10. In some embodiments, a codon-optimized mRNA molecule is at least 97% identical to SEQ ID NO: 10. In some embodiments, a codon-optimized mRNA molecule is at least 98% identical to SEQ ID NO: 10. In some embodiments, a codon-optimized mRNA molecule is at least 99% identical to SEQ ID NO: 10. In some embodiments, a codon-optimized mRNA molecule is identical to SEQ ID NO: 10.

In some embodiments, a codon-optimized mRNA molecule is at least 85% identical to SEQ ID NO: 11. In some embodiments, a codon-optimized mRNA molecule is at least 90% identical to SEQ ID NO: 11. In some embodiments, a codon-optimized mRNA molecule is at least 92% identical to SEQ ID NO: 11. In some embodiments, a codon-optimized mRNA molecule is at least 95% identical to SEQ ID NO: 11. In some embodiments, a codon-optimized mRNA molecule is at least 96% identical to SEQ ID NO: 11. In some embodiments, a codon-optimized mRNA molecule is at least 97% identical to SEQ ID NO: 11. In some embodiments, a codon-optimized mRNA molecule is at least 98% identical to SEQ ID NO: 11. In some embodiments, a codon-optimized mRNA molecule is at least 99% identical to SEQ ID NO: 11. In some embodiments, a codon-optimized mRNA molecule is identical to SEQ ID NO: 11.

In some embodiments, the mRNA molecule comprises a 5' untranslated region (UTR). In some embodiments, the mRNA molecule comprises a 3' untranslated region (UTR). In some embodiments, the 5' untranslated region (UTR) comprises SEQ ID NO: 12. In some embodiments, the 3' untranslated region (UTR) comprises SEQ ID NO: 13. In some embodiments, the 3' untranslated region (UTR) comprises SEQ ID NO: 14.

In some embodiments, an mRNA molecule further comprises a poly-A tail. In some embodiments, an mRNA molecule further comprises a poly-A tail of at least 70 residues in length. In some embodiments, an mRNA molecule further comprises a poly-A tail of at least 100 residues in length. In some embodiments, an mRNA molecule further comprises a poly-A tail of at least 120 residues in length. In some embodiments, an mRNA molecule further comprises a poly-A tail of at least 150 residues in length. In some embodiments, an mRNA molecule further comprises a poly-A tail of at least 200 residues in length. In some embodiments, an mRNA molecule further comprises a poly-A tail of at least 250 residues in length.

In some embodiments, an mRNA molecule comprises a 5' cap.

In some embodiments, an mRNA molecule comprises at least one nonstandard nucleobase. In some embodiments, the nonstandard nucleobase is chosen from one or more of 5-methyl-cytidine, pseudouridine, and 2-thio-uridine.

In some embodiments, an mRNA molecule is for use in inducing functional CFTR expression in a mammal or a mammalian cell.

In some embodiments, the functional CFTR protein expression induced by the codon-optimized mRNA molecule is at least 1.2-fold greater than the protein expression induced by a non-codon optimized mRNA molecule encoding a wild-type CFTR protein. In some embodiments, the functional CFTR protein expression induced by the codon-optimized mRNA molecule is at least 1.5-fold greater than the protein expression induced by a non-codon optimized mRNA molecule encoding a wild-type CFTR protein. In some embodiments, the functional CFTR protein expression induced by the codon-optimized mRNA molecule is at least 1.8-fold greater than the protein expression induced by a non-codon optimized mRNA molecule encoding a wild-type CFTR protein. In some embodiments, the functional CFTR protein expression induced by the codon-optimized mRNA molecule is at least 2-fold greater than the protein expression induced by a non-codon optimized mRNA molecule encoding a wild-type CFTR protein. In some embodiments, the functional CFTR protein expression induced by the codon-optimized mRNA molecule is at least 2.3-fold greater than the protein expression induced by a non-codon optimized mRNA molecule encoding a wild-type CFTR protein. In some embodiments, the functional CFTR protein expression induced by the codon-optimized mRNA molecule is at least 2.5-fold greater than the protein expression induced by a non-codon optimized mRNA molecule encoding a wild-type CFTR protein. In some embodiments, the functional CFTR protein expression induced by the codon-optimized mRNA molecule is at least 2.8-fold greater than the protein expression induced by a non-codon optimized mRNA molecule encoding a wild-type CFTR protein. In some embodiments, the functional CFTR protein expression induced by the codon-optimized mRNA molecule is at least 3.0-fold greater than the protein expression induced by a non-codon optimized mRNA molecule encoding a wild-type CFTR protein. In some embodiments, the functional CFTR protein expression induced by the codon-optimized mRNA molecule is at least 3.2-fold greater than the protein expression induced by a non-codon optimized mRNA molecule encoding a wild-type CFTR protein. In some embodiments, the functional CFTR protein expression induced by the codon-optimized mRNA molecule is at least 3.5-fold greater than the protein expression induced by a non-codon optimized mRNA molecule encoding a wild-type CFTR protein. In some embodiments, the functional CFTR protein expression induced by the codon-optimized mRNA molecule is at least 3.7-fold greater than the protein expression induced by a non-codon optimized mRNA molecule encoding a wild-type CFTR protein. In some embodiments, the functional CFTR protein expression induced by the codon-optimized mRNA molecule is at least 4.0-fold greater than the protein expression induced by a non-codon optimized mRNA molecule encoding a wild-type CFTR protein. In some embodiments, the functional CFTR protein expression induced by the codon-optimized mRNA molecule is at least 4.5-fold greater than the protein expression induced by a non-codon optimized mRNA molecule encoding a wild-type CFTR protein. In some embodiments, the functional CFTR protein expression induced by the codon-optimized mRNA molecule is at least 5.0-fold greater than the protein expression induced by a non-codon optimized mRNA molecule encoding a wild-type CFTR protein.

In one aspect, the present invention provides a polynucleotide comprising a sequence complementary to a codon-optimized mRNA molecule comprising a coding sequence encoding Cystic Fibrosis Transmembrane Conductance Regulator (CFTR) protein, wherein the coding sequence encodes the amino acid sequence of SEQ ID NO: 1 and the coding sequence is at least 85% identical to SEQ ID NO: 2 or SEQ ID NO: 3.

In some embodiments, a polynucleotide is a linear polynucleotide comprising deoxyribonucleotide residues. In some embodiments, a polynucleotide is a circular polynucleotide comprising deoxyribonucleotide residues.

In one aspect, the present invention provides a culture cell comprising a polynucleotide comprising a sequence complementary to a codon-optimized mRNA molecule comprising a coding sequence encoding Cystic Fibrosis Transmembrane Conductance Regulator (CFTR) protein, wherein the coding sequence encodes the amino acid sequence of SEQ ID NO: 1 and the coding sequence is at least 85% identical to SEQ ID NO: 2 or SEQ ID NO: 3.

In one aspect, the present invention provides a pharmaceutical composition for treating cystic fibrosis, comprising a codon optimized mRNA encoding a Cystic Fibrosis Transmembrane Conductance Regulator (CFTR) protein of SEQ ID NO: 1 and wherein the codon optimized CFTR mRNA comprises a polynucleotide sequence at least 85% identical to SEQ ID NO: 2 or SEQ ID NO: 3.

In some embodiments, a codon-optimized CFTR mRNA is at least 85% identical to SEQ ID NO: 2. In some embodiments, a codon-optimized CFTR mRNA is at least 90% identical to SEQ ID NO: 2. In some embodiments, a codon-optimized CFTR mRNA is at least 92% identical to SEQ ID NO: 2. In some embodiments, a codon-optimized CFTR mRNA is at least 95% identical to SEQ ID NO: 2. In some embodiments, a codon-optimized CFTR mRNA is at least 96% identical to SEQ ID NO: 2. In some embodiments, a codon-optimized CFTR mRNA is at least 97% identical to SEQ ID NO: 2. In some embodiments, a codon-optimized CFTR mRNA is at least 98% identical to SEQ ID NO: 2. In some embodiments, a codon-optimized CFTR mRNA is at least 99% identical to SEQ ID NO: 2. In some embodiments, a codon-optimized CFTR mRNA is identical to SEQ ID NO: 2.

In some embodiments, a codon-optimized CFTR mRNA is at least 85% identical to SEQ ID NO: 3. In some embodiments, a codon-optimized CFTR mRNA is at least 90% identical to SEQ ID NO: 3. In some embodiments, a codon-optimized CFTR mRNA is at least 92% identical to SEQ ID NO: 3. In some embodiments, a codon-optimized CFTR mRNA is at least 95% identical to SEQ ID NO: 3. In some embodiments, a codon-optimized CFTR mRNA is at least 96% identical to SEQ ID NO: 3. In some embodiments, a codon-optimized CFTR mRNA is at least 97% identical to SEQ ID NO: 3. In some embodiments, a codon-optimized CFTR mRNA is at least 98% identical to SEQ ID NO: 3. In some embodiments, a codon-optimized CFTR mRNA is at least 99% identical to SEQ ID NO: 3. In some embodiments, a codon-optimized CFTR mRNA is identical to SEQ ID NO: 3.

In some embodiments, a codon-optimized CFTR mRNA is at least 85% identical to SEQ ID NO: 4. In some embodiments, a codon-optimized CFTR mRNA is at least 90% identical to SEQ ID NO: 4. In some embodiments, a codon-optimized CFTR mRNA is at least 92% identical to SEQ ID NO: 4. In some embodiments, a codon-optimized CFTR mRNA is at least 95% identical to SEQ ID NO: 4. In some embodiments, a codon-optimized CFTR mRNA is at least 96% identical to SEQ ID NO: 4. In some embodiments, a codon-optimized CFTR mRNA is at least 97% identical to SEQ ID NO: 4. In some embodiments, a codon-optimized CFTR mRNA is at least 98% identical to SEQ ID NO: 4. In some embodiments, a codon-optimized CFTR mRNA is at least 99% identical to SEQ ID NO: 4. In some embodiments, a codon-optimized CFTR mRNA is identical to SEQ ID NO: 4.

In some embodiments, a codon-optimized CFTR mRNA is at least 85% identical to SEQ ID NO: 5. In some embodiments, a codon-optimized CFTR mRNA is at least 90% identical to SEQ ID NO: 5. In some embodiments, a codon-optimized CFTR mRNA is at least 92% identical to SEQ ID NO: 5. In some embodiments, a codon-optimized CFTR mRNA is at least 95% identical to SEQ ID NO: 5. In some embodiments, a codon-optimized CFTR mRNA is at least 96% identical to SEQ ID NO: 5. In some embodiments, a codon-optimized CFTR mRNA is at least 97% identical to SEQ ID NO: 5. In some embodiments, a codon-optimized CFTR mRNA is at least 98% identical to SEQ ID NO: 5. In some embodiments, a codon-optimized CFTR mRNA is at least 99% identical to SEQ ID NO: 5. In some embodiments, a codon-optimized CFTR mRNA is identical to SEQ ID NO: 5.

In some embodiments, a codon-optimized CFTR mRNA is at least 85% identical to SEQ ID NO: 6. In some embodiments, a codon-optimized CFTR mRNA is at least 90% identical to SEQ ID NO: 6. In some embodiments, a codon-optimized CFTR mRNA is at least 92% identical to SEQ ID NO: 6. In some embodiments, a codon-optimized CFTR mRNA is at least 95% identical to SEQ ID NO: 6. In some embodiments, a codon-optimized CFTR mRNA is at least 96% identical to SEQ ID NO: 6. In some embodiments, a codon-optimized CFTR mRNA is at least 97% identical to SEQ ID NO: 6. In some embodiments, a codon-optimized CFTR mRNA is at least 98% identical to SEQ ID NO: 6. In some embodiments, a codon-optimized CFTR mRNA is at least 99% identical to SEQ ID NO: 6. In some embodiments, a codon-optimized CFTR mRNA is identical to SEQ ID NO: 6.

In some embodiments, a codon-optimized CFTR mRNA is at least 85% identical to SEQ ID NO: 7. In some embodiments, a codon-optimized CFTR mRNA is at least 90% identical to SEQ ID NO: 7. In some embodiments, a codon-optimized CFTR mRNA is at least 92% identical to SEQ ID NO: 7. In some embodiments, a codon-optimized CFTR mRNA is at least 95% identical to SEQ ID NO: 7. In some embodiments, a codon-optimized CFTR mRNA is at least 96% identical to SEQ ID NO: 7. In some embodiments, a codon-optimized CFTR mRNA is at least 97% identical to SEQ ID NO: 27 In some embodiments, a codon-optimized CFTR mRNA is at least 98% identical to SEQ ID NO: 7. In some embodiments, a codon-optimized CFTR mRNA is at least 99% identical to SEQ ID NO: 7. In some embodiments, a codon-optimized CFTR mRNA is identical to SEQ ID NO: 7.

In some embodiments, a codon-optimized CFTR mRNA is at least 85% identical to SEQ ID NO: 8. In some embodiments, a codon-optimized CFTR mRNA is at least 90% identical to SEQ ID NO: 8. In some embodiments, a codon-optimized CFTR mRNA is at least 92% identical to SEQ ID NO: 8. In some embodiments, a codon-optimized CFTR mRNA is at least 95% identical to SEQ ID NO: 8. In some embodiments, a codon-optimized CFTR mRNA is at least 96% identical to SEQ ID NO: 8. In some embodiments, a codon-optimized CFTR mRNA is at least 97% identical to SEQ ID NO: 8. In some embodiments, a codon-optimized CFTR mRNA is at least 98% identical to SEQ ID NO: 2. In some embodiments, a codon-optimized CFTR mRNA is at least 99% identical to SEQ ID NO: 8. In some embodiments, a codon-optimized CFTR mRNA is identical to SEQ ID NO: 8.

In some embodiments, a codon-optimized CFTR mRNA is at least 85% identical to SEQ ID NO: 9. In some embodiments, a codon-optimized CFTR mRNA is at least 90% identical to SEQ ID NO: 9. In some embodiments, a codon-optimized CFTR mRNA is at least 92% identical to SEQ ID NO: 9. In some embodiments, a codon-optimized CFTR mRNA is at least 95% identical to SEQ ID NO: 9. In some embodiments, a codon-optimized CFTR mRNA is at least 96% identical to SEQ ID NO: 9. In some embodiments, a codon-optimized CFTR mRNA is at least 97% identical to SEQ ID NO: 9. In some embodiments, a codon-optimized CFTR mRNA is at least 98% identical to SEQ ID NO: 9. In some embodiments, a codon-optimized CFTR mRNA is at least 99% identical to SEQ ID NO: 9. In some embodiments, a codon-optimized CFTR mRNA is identical to SEQ ID NO: 9.

In some embodiments, a codon-optimized CFTR mRNA is at least 85% identical to SEQ ID NO: 10. In some embodiments, a codon-optimized CFTR mRNA is at least 90% identical to SEQ ID NO: 10. In some embodiments, a codon-optimized CFTR mRNA is at least 92% identical to SEQ ID NO: 10. In some embodiments, a codon-optimized CFTR mRNA is at least 95% identical to SEQ ID NO: 10. In some embodiments, a codon-optimized CFTR mRNA is at least 96% identical to SEQ ID NO: 10. In some embodiments, a codon-optimized CFTR mRNA is at least 97% identical to SEQ ID NO: 10. In some embodiments, a codon-optimized CFTR mRNA is at least 98% identical to SEQ ID NO: 10. In some embodiments, a codon-optimized CFTR mRNA is at least 99% identical to SEQ ID NO: 10. In some embodiments, a codon-optimized CFTR mRNA is identical to SEQ ID NO: 10.

In some embodiments, a codon-optimized CFTR mRNA is at least 85% identical to SEQ ID NO: 11. In some embodiments, a codon-optimized CFTR mRNA is at least 90% identical to SEQ ID NO: 11. In some embodiments, a codon-optimized CFTR mRNA is at least 92% identical to SEQ ID NO: 11. In some embodiments, a codon-optimized CFTR mRNA is at least 95% identical to SEQ ID NO: 11. In some embodiments, a codon-optimized CFTR mRNA is at least 96% identical to SEQ ID NO: 11. In some embodiments, a codon-optimized CFTR mRNA is at least 97% identical to SEQ ID NO: 11. In some embodiments, a codon-optimized CFTR mRNA is at least 98% identical to SEQ ID NO: 11. In some embodiments, a codon-optimized CFTR mRNA is at least 99% identical to SEQ ID NO: 11. In some embodiments, a codon-optimized CFTR mRNA is identical to SEQ ID NO: 11.

In some embodiments, the codon optimized CFTR mRNA is encapsulated within a nanoparticle. In some embodiments, the nanoparticle is a liposome.

In some embodiments, the liposome comprises one or more cationic lipids, one or more non-cationic lipids, and one or more PEG-modified lipids. In some embodiments, the liposome comprises one or more cholesterol-based lipids. In some embodiments, the liposome comprises one or more cationic lipids, one or more non-cationic lipids, one or more cholesterol-based lipids and one or more PEG-modified lipids. In some embodiments, the liposome comprises no more than three distinct lipid components. In some embodiments, one distinct lipid component is a sterol-based cationic lipid. In some embodiments, a sterol-based cationic lipid is imidazole cholesterol ester (ICE).

In some embodiments, one or more cationic lipids comprise GL-TES-SA-DME-E18-2. In some embodiments, one or more cationic lipids comprise TL1-01D-DMA. In some embodiments, one or more cationic lipids comprise SY-3-E14-DMAPr. In some embodiments, one or more cationic lipids comprise TL1-10D-DMA. In some embodiments, one or more cationic lipids comprise Guan-SS-Chol. In some embodiments, one or more cationic lipids comprise GL-TES-SA-DMP-E18-2. In some embodiments, one or more cationic lipids comprise HEP-E4-E10. In some embodiments, one or more cationic lipids comprise HEP-E3-E10. In some embodiments, one or more cationic lipids comprise TL1-04D-DMA.

In some embodiments, lipid nanoparticles comprise a cationic lipid that is GL-TES-SA-DME-E18-2. In some embodiments, lipid nanoparticles comprise a cationic lipid that is TL1-01D-DMA. In some embodiments, lipid nanoparticles comprise a cationic lipid that is SY-3-E14-DMAPr. In some embodiments, lipid nanoparticles comprise a cationic lipid that is TL1-10D-DMA. In some embodiments, lipid nanoparticles comprise a cationic lipid that is Guan-SS-Chol. In some embodiments, lipid nanoparticles comprise a cationic lipid that is GL-TES-SA-DMP-E18-2. In some embodiments, lipid nanoparticles comprise a cationic lipid that is HEP-E4-E10. In some embodiments, lipid nanoparticles comprise a cationic lipid that is HEP-E3-E10. In some embodiments, lipid nanoparticles comprise a cationic lipid that is TL1-04D-DMA.

In some embodiments, the liposome has a size of less than about 200 nm. In some embodiments, the liposome has a size of less than about 150 nm. In some embodiments, the liposome has a size of less than about 120 nm. In some embodiments, the liposome has a size of less than about 110 nm. In some embodiments, the liposome has a size of less than about 100 nm. In some embodiments, the liposome has a size of less than about 80 nm. In some embodiments, the liposome has a size of less than about 60 nm. In some embodiments, the liposome has a size of less than about 50 nm. In some embodiments, the liposome has a size of less than about 40 nm. In some embodiments, the liposome has a size of less than about 30 nm.

In some embodiments, the functional CFTR protein expression induced by the codon-optimized mRNA is at least 1.2-fold greater than the protein expression induced by a non-codon optimized mRNA molecule encoding a wild-type CFTR protein. In some embodiments, the functional CFTR protein expression induced by the codon-optimized mRNA is at least 1.5-fold greater than the protein expression induced by a non-codon optimized mRNA molecule encoding a wild-type CFTR protein. In some embodiments, the functional CFTR protein expression induced by the codon-optimized mRNA is at least 1.8-fold greater than the protein expression induced by a non-codon optimized mRNA molecule encoding a wild-type CFTR protein. In some embodiments, the functional CFTR protein expression induced by the codon-optimized mRNA is at least 2-fold greater than the protein expression induced by a non-codon optimized mRNA molecule encoding a wild-type CFTR protein. In some embodiments, the functional CFTR protein expression induced by the codon-optimized mRNA is at least 2.3-fold greater than the protein expression induced by a non-codon optimized mRNA molecule encoding a wild-type CFTR protein. In some embodiments, the functional CFTR protein expression induced by the codon-optimized mRNA is at least 2.5-fold greater than the protein expression induced by a non-codon optimized mRNA molecule encoding a wild-type CFTR protein. In some embodiments, the functional CFTR protein expression induced by the codon-optimized mRNA is at least 2.8-fold greater than the protein expression induced by a non-codon optimized mRNA molecule encoding a wild-type CFTR protein. In some embodiments, the functional CFTR protein expression induced by the codon-optimized mRNA is at least 3-fold greater than the protein expression induced by a non-codon optimized mRNA molecule encoding a wild-type CFTR protein. In some embodiments, the functional CFTR protein expression induced by the codon-optimized mRNA is at least 3.2-fold greater than the protein expression induced by a non-codon optimized mRNA molecule encoding a wild-type CFTR protein. In some embodiments, the functional CFTR protein expression induced by the codon-optimized mRNA is at least 3.5-fold greater than the protein expression induced by a non-codon optimized mRNA molecule encoding a wild-type CFTR protein. In some embodiments, the functional CFTR protein expression induced by the codon-optimized mRNA is at least 3.8-fold greater than the protein expression induced by a non-codon optimized mRNA molecule encoding a wild-type CFTR protein. In some embodiments, the functional CFTR protein expression induced by the codon-optimized mRNA is at least 4-fold greater than the protein expression induced by a non-codon optimized mRNA molecule encoding a wild-type CFTR protein. In some embodiments, the functional CFTR protein expression induced by the codon-optimized mRNA is at least 5-fold greater than the protein expression induced by a non-codon optimized mRNA molecule encoding a wild-type CFTR protein.

In some embodiments, the CFTR protein expressed by the codon-optimized mRNA molecule is at least 1.2-fold more potent than the CFTR protein expressed by a non-codon optimized mRNA molecule encoding a wild-type CFTR protein. In some embodiments, the CFTR protein expressed by the codon-optimized mRNA molecule is at least 1.5-fold more potent than the CFTR protein expressed by a non-codon optimized mRNA molecule encoding a wild-type CFTR protein. In some embodiments, the CFTR protein expressed by the codon-optimized mRNA molecule is at least 1.8-fold more potent than the CFTR protein expressed by a non-codon optimized mRNA molecule encoding a wild-type CFTR protein. In some embodiments, the CFTR protein expressed by the codon-optimized mRNA molecule is at least 2.0-fold more potent than the CFTR protein expressed by a non-codon optimized mRNA molecule encoding a wild-type CFTR protein. In some embodiments, the CFTR protein expressed by the codon-optimized mRNA molecule is at least 2.2-fold more potent than the CFTR protein expressed by a non-codon optimized mRNA molecule encoding a wild-type CFTR protein. In some embodiments, the CFTR protein expressed by the codon-optimized mRNA molecule is at least 2.5-fold more potent than the CFTR protein expressed by a non-codon optimized mRNA molecule encoding a wild-type CFTR protein. In some embodiments, the CFTR protein expressed by the codon-optimized mRNA molecule is at least 2.8-fold more potent than the CFTR protein expressed by a non-codon optimized mRNA molecule encoding a wild-type CFTR protein. In some embodiments, the CFTR protein expressed by the codon-optimized mRNA molecule is at least 3.0-fold more potent than the CFTR protein expressed by a non-codon optimized mRNA molecule encoding a wild-type CFTR protein. In some embodiments, the CFTR protein expressed by the codon-optimized mRNA molecule is at least 3.2-fold more potent than the CFTR protein expressed by a non-codon optimized mRNA molecule encoding a wild-type CFTR protein. In some embodiments, the CFTR protein expressed by the codon-optimized mRNA molecule is at least 3.5-fold more potent than the CFTR protein expressed by a non-codon optimized mRNA molecule encoding a wild-type CFTR protein. In some embodiments, the CFTR protein expressed by the codon-optimized mRNA molecule is at least 4-fold more potent than the CFTR protein expressed by a non-codon optimized mRNA molecule encoding a wild-type CFTR protein. In some embodiments, the CFTR protein expressed by the codon-optimized mRNA molecule is at least 5-fold more potent than the CFTR protein expressed by a non-codon optimized mRNA molecule encoding a wild-type CFTR protein.

In some embodiments, the pharmaceutical composition further comprises a CFTR potentiator. In some embodiments, the pharmaceutical composition further comprises a CFTR corrector. In some embodiments, the pharmaceutical composition further comprises a CFTR activator. In some embodiments, the pharmaceutical composition further comprises a CFTR potentiator, corrector and/or activator. Suitable CFTR potentiators, correctors and/or activators include ivacaftor (trade name Kalydeco®), lumacaftor (trade name Orkambi®), tezacaftor, vX-659, VX-445, VX-152, VX-440, VX-371, VX-561, GLPG1837, GLPG2222, GLPG2737, GLPG2451, GLPG1837, PTI-428, PTI-801, PTI-808, and eluforsen. In some embodiments, the pharmaceutical composition further comprises ivacaftor. In some embodiments, the pharmaceutical composition further comprises lumacaftor. In some embodiments, the pharmaceutical composition further comprises tezacaftor. In some embodiments, the pharmaceutical composition further comprises ivacaftor, lumacaftor, tezacaftor, or a combination. In some embodiments, the pharmaceutical composition further comprises VX-659. In some embodiments, the pharmaceutical composition further comprises VX-445. In some embodiments, the pharmaceutical composition further comprises VX-152. In some embodiments, the pharmaceutical composition further comprises VX-440. In some embodiments, the pharmaceutical composition further comprises VX-371. In some embodiments, the pharmaceutical composition further comprises VX-561. In some embodiments, the pharmaceutical composition further comprises GLPG1837. In some embodiments, the pharmaceutical composition further comprises GLPG2222. In some embodiments, the pharmaceutical composition further comprises GLPG2737. In some embodiments, the pharmaceutical composition further comprises GLPG2451. In some embodiments, the pharmaceutical composition further comprises GLPG1837. In some embodiments, the pharmaceutical composition further comprises PTI-428. In some embodiments, the pharmaceutical composition further comprises PTI-801. In some embodiments, the pharmaceutical composition further comprises PTI-808. In some embodiments, the pharmaceutical composition further comprises eluforsen. In some embodiments, the pharmaceutical composition further comprises any combination of CFTR potentiators, correctors, and/or activators.

In one aspect, the invention provides a method of inducing CFTR expression in epithelial cells in a lung of a mammal comprising a step of contacting the epithelial cells in the lung of the mammal with a pharmaceutical composition of the present invention.

In one aspect, the invention provides a method treating cystic fibrosis comprising administering to a subject in need of treatment a pharmaceutical composition of the present invention.

In some embodiments, the codon optimized CFTR mRNA is administered via pulmonary delivery. In some embodiments, the codon optimized CFTR mRNA is administered via intravenous delivery. In some embodiments, the codon optimized CFTR mRNA is administered via oral, rectal, vaginal, transmucosal, or intestinal administration; parenteral delivery, including intradermal, transdermal (topical), intramuscular, subcutaneous, intramedullary injections, as well as intrathecal, direct intraventricular, intravenous, intraperitoneal, and/or intranasal administration.

In some embodiments, the pulmonary delivery is nebulization. In some embodiments, the codon optimized CFTR mRNA is administered via aerosolization.

In some embodiments, treating the subject is achieved at a lower therapeutically effective dose in comparison to treating the subject with a non-codon optimized mRNA encoding a wild type CFTR.

In some embodiments, treating the subject in need results in shorter nebulization times to administer a therapeutically effective dose in comparison to treating with a non-codon optimized mRNA encoding a wild type CFTR.

BRIEF DESCRIPTION OF THE DRAWING

The drawings are for illustration purposes only not for limitation.

As illustrated in FIG. 1A, the process receives an amino acid sequence of interest and a first codon usage table which reflects the frequency of each codon in a given organism (e.g., a mammal or human). The process then removes codons from the first codon usage table if they are associated with a codon usage frequency which is less than a threshold frequency (e.g., 10%). The codon usage frequencies of the codons not removed in the first step are normalized to generate a normalized codon usage table. The process uses the normalized codon usage table to generate a list of optimized nucleotide sequences. Each of the optimized nucleotide sequences encode the amino acid sequence of interest. As illustrated in FIG. 1B, the list of optimized nucleotide sequences is further processed by applying a motif screen filter, guanine-cytosine (GC) content analysis filter, and codon adaptation index (CAI) analysis filter, in that order, to generate an updated list of optimized nucleotide sequences.

DEFINITIONS

Figure 1A:
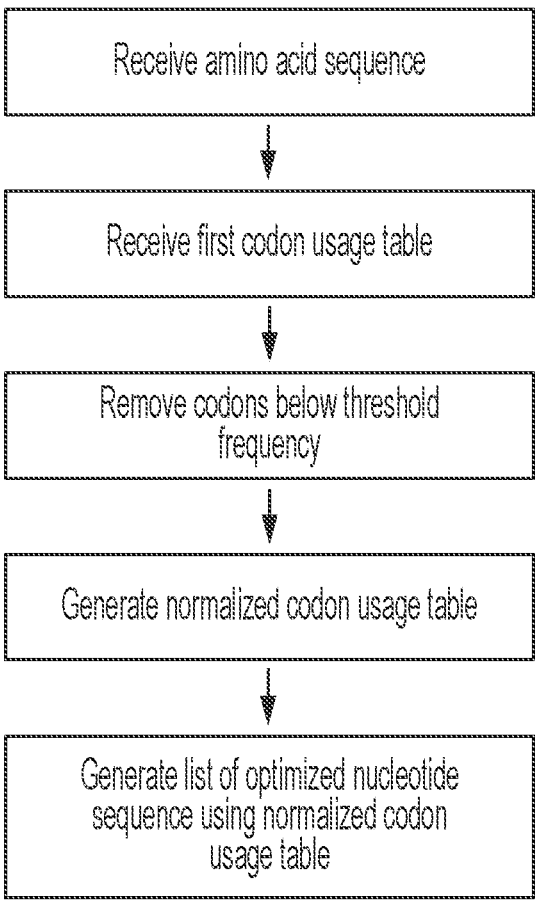
FIG. 1A and FIG. 1B illustrate a process for generating optimized nucleotide sequences in accordance with the invention.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

As used herein, the term "batch" refers to a quantity or amount of mRNA synthesized at one time, e.g., produced according to a single manufacturing order during the same cycle of manufacture. A batch may refer to an amount of mRNA synthesized in one reaction that occurs via a single aliquot of enzyme and/or a single aliquot of DNA template for continuous synthesis under one set of conditions. In some embodiments, a batch would include the mRNA produced from a reaction in which not all reagents and/or components are supplemented and/or replenished as the reaction progresses. The term "not in a single batch" would not mean mRNA synthesized at different times that are combined to achieve the desired amount.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery). In some embodiments, delivery is pulmonary delivery, e.g., comprising nebulization.

Encapsulation: As used herein, the term "encapsulation," or grammatical equivalent, refers to the process of confining an mRNA molecule within a nanoparticle.

Engineered or mutant. As used herein, the terms "engineered" or "mutant", or grammatical equivalents refer to a nucleotide or protein sequence comprising one or more modifications compared to its naturally-occurring sequence, including but not limited to deletions, insertions of heterologous nucleic acids or amino acids, inversions, substitutions, or combinations thereof.

Expression: As used herein, "expression" of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and grammatical equivalents, are used interchangeably.

Functional: As used herein, a "functional" biological molecule is a biological molecule in a form in which it exhibits a property and/or activity by which it is characterized.

Half-life: As used herein, the term "half-life" is the time required for a quantity such as nucleic acid or protein concentration or activity to fall to half of its value as measured at the beginning of a time period.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

messenger RNA (mRNA): As used herein, the term "messenger RNA (mRNA)" refers to a polynucleotide that encodes at least one polypeptide. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery. In some embodiments, the nucleotides T and U are used interchangeably in sequence descriptions.

Patient. As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Stable: As used herein, the term "stable" protein or its grammatical equivalents refer to protein that retains its physical stability and/or biological activity. In one embodiment, protein stability is determined based on the percentage of monomer protein in the solution, at a low percentage of degraded (e.g., fragmented) and/or aggregated protein. In one embodiment, a stable engineered protein retains or exhibits an enhanced half-life as compared to a wild-type protein. In one embodiment, a stable engineered protein is less prone to ubiquitination that leads to proteolysis as compared to a wild-type protein.

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

DETAILED DESCRIPTION

The present invention provides, among other things, improved methods and pharmaceutical compositions for treating cystic fibrosis using messenger RNA (mRNA) encoding an engineered or mutant Cystic Fibrosis Transmembrane Conductance Regulator (CFTR) protein. In some embodiments, the mRNA is a codon-optimized mRNA. In particular embodiments, the engineered or mutant CFTR proteins achieve higher activity or stability than the wildtype CFTR protein. mRNAs disclosed herein encoding engineered or mutant CFTR proteins are particularly useful for treating cystic fibrosis by mRNA therapeutics.

Cystic Fibrosis

The present invention may be used to treat a subject who is suffering from or susceptible to cystic fibrosis. Cystic fibrosis is a genetic disorder characterized by mutations in the gene for Cystic Fibrosis Transmembrane Conductance Regulator (CFTR). The CFTR protein functions as a channel across the membrane of cells that produce mucus, sweat, saliva, tears, and digestive enzymes. The channel transports negatively charged particles called chloride ions into and out of cells. The transport of chloride ions helps control the movement of water in tissues, which is necessary for the production of thin, freely flowing mucus. Mucus is a slippery substance that lubricates and protects the lining of the airways, digestive system, reproductive system, and other organs and tissues.

Respiratory symptoms of cystic fibrosis include: a persistent cough that produces thick mucus (sputum), wheezing, breathlessness, exercise intolerance, repeated lung infections and inflamed nasal passages or a stuffy nose. Digestive symptoms of cystic fibrosis include: foul-smelling, greasy stools, poor weight gain and growth, intestinal blockage, particularly in newborns (meconium ileus), and severe constipation.

Codon Optimized mRNA Encoding CFTR

In some embodiments, the present invention provides methods and compositions for delivering codon optimized mRNA encoding CFTR to a subject for the treatment of cystic fibrosis. A suitable codon optimized CFTR mRNA encodes any full length, fragment or portion of a CFTR protein which can be substituted for naturally-occurring CFTR protein activity and/or reduce the intensity, severity, and/or frequency of one or more symptoms associated with cystic fibrosis.

According to an increasing amount of research, mRNAs contain numerous layers of information that overlap the amino acid code. Traditionally, codon optimization has been used to remove rare codons which were thought to be rate-limiting for protein expression. While fast growing bacteria and yeast both exhibit strong codon bias in highly expressed genes, higher eukaryotes exhibit much less codon bias, making it more difficult to discern codons that may be rate-limiting. In addition, it has been found that codon bias per se does not necessarily yield high expression but requires other features.

For example, rare codons have been implicated in slowing translation and forming pause sites, which may be required for correct protein folding. Therefore, variations in codon usage may provide a mechanism to fine-tune the temporal pattern of elongation and thus increase the time available for a protein to take on its correct confirmation. Codon optimization can interfere with this fine-tuning mechanism, resulting in less efficient protein translation or an increased amount of incorrectly folded proteins. Similarly, codon optimization may disrupt the normal patterns of cognate and wobble tRNA usage, thereby affecting protein structure and function because wobble-dependent slowing of elongation may likewise have been selected as a mechanism for achieving correct protein folding.

Various methods of performing codon optimization are known in the art, however, each has significant drawbacks and limitations from a computational and/or therapeutic point of view. In particular, known methods of codon optimization often involve, for each amino acid, replacing every codon with the codon having the highest usage for that amino acid, such that the "optimized" sequence contains only one codon encoding each amino acid (so may be referred to as a one-to-one sequence).

Despite these obstacles, the inventors have arrived at improved codon-optimized CFTR sequences that enhances expression of the CFTR protein at least two-fold over the coding sequence of the wild type gene. It is expected that the observed improvement in expression of the codon-optimized CFTR coding sequence will result in an improved, more cost-effective mRNA replacement therapy for patients suffering from cystic fibrosis, because it does not require the use of modified nucleotides for the preparation of the mRNA and allows treatment with a reduced dose and/or at extended dosing intervals.

The genetic code has 64 possible codons. Each codon comprises a sequence of three nucleotides. The usage frequency for each codon in the protein-coding regions of the genome can be calculated by determining the number of instances that a specific codon appears within the protein-coding regions of the genome, and subsequently dividing the obtained value by the total number of codons that encode the same amino acid within protein-coding regions of the genome.

A codon usage table contains experimentally derived data regarding how often, for the particular biological source from which the table has been generated, each codon is used to encode a certain amino acid. This information is expressed, for each codon, as a percentage (0 to 100%), or fraction (0 to 1), of how often that codon is used to encode a certain amino acid relative to the total number of times a codon encodes that amino acid.

Codon usage tables are stored in publically available databases, such as the Codon Usage Database (Nakamura et al. (2000) *Nucleic Acids Research* 28(1), 292; available online at https://www.kazusa.or.jp/codon/), and the High-performance Integrated Virtual Environment-Codon Usage Tables (HIVE-CUTs) database (Athey et al., (2017), BMC Bioinformatics 18(1), 391; available online at http://hive.biochemistry.gwu.edu/review/codon).

During the first step of codon optimization, codons are removed from a first codon usage table which reflects the frequency of each codon in a given organism (e.g., a mammal or human) if they are associated with a codon usage frequency which is less than a threshold frequency (e.g., 10%). The codon usage frequencies of the codons not removed in the first step are normalized to generate a normalized codon usage table. An optimized nucleotide sequence encoding an amino acid sequence of interest is generated by selecting a codon for each amino acid in the amino acid sequence based on the usage frequency of the one or more codons associated with a given amino acid in the normalized codon usage table. The probability of selecting a certain codon for a given amino acid is equal to the usage frequency associated with the codon associated with this amino acid in the normalized codon usage table.

The codon-optimized sequences of the invention are generated by a computer-implemented method for generating an optimized nucleotide sequence. The method comprises: (i) receiving an amino acid sequence, wherein the amino acid sequence encodes a peptide, polypeptide, or protein; (ii) receiving a first codon usage table, wherein the first codon usage table comprises a list of amino acids, wherein each amino acid in the table is associated with at least one codon and each codon is associated with a usage frequency; (iii) removing from the codon usage table any codons associated with a usage frequency which is less than a threshold frequency; (iv) generating a normalized codon usage table by normalizing the usage frequencies of the codons not removed in step (iii); and (v) generating an optimized nucleotide sequence encoding the amino acid sequence by selecting a codon for each amino acid in the amino acid sequence based on the usage frequency of the one or more codons associated with the amino acid in the normalized codon usage table. The threshold frequency can be in the range of 5%-30%, in particular 5%, 10%, 15%, 20%, 25%, or 30%. In the context of the present invention, the threshold frequency is typically 10%.

The step of generating a normalized codon usage table comprises: (a) distributing the usage frequency of each codon associated with a first amino acid and removed in step (iii) to the remaining codons associated with the first amino acid; and (b) repeating step (a) for each amino acid to produce a normalized codon usage table. In some embodiments, the usage frequency of the removed codons is distributed equally amongst the remaining codons. In some embodiments, the usage frequency of the removed codons is distributed amongst the remaining codons proportionally based on the usage frequency of each remaining codon. "Distributed" in this context may be defined as taking the combined magnitude of the usage frequencies of removed codons associated with a certain amino acid and apportioning some of this combined frequency to each of the remaining codons encoding the certain amino acid.

The step of selecting a codon for each amino acid comprises: (a) identifying, in the normalized codon usage table, the one or more codons associated with a first amino acid of the amino acid sequence; (b) selecting a codon associated with the first amino acid, wherein the probability of selecting a certain codon is equal to the usage frequency associated with the codon associated with the first amino acid in the normalized codon usage table; and (c) repeating steps (a) and (b) until a codon has been selected for each amino acid in the amino acid sequence.

The step of generating an optimized nucleotide sequence by selecting a codon for each amino acid in the amino acid sequence (step (v) in the above method) is performed n times to generate a list of optimized nucleotide sequences.

Motif Screen

A motif screen filter is applied to the list of optimized nucleotide sequences. Optimized nucleotide sequences encoding any known negative cis-regulatory elements and negative repeat elements are removed from the list to generate an updated list.

For each optimized nucleotide sequence in the list, it is also determined whether it contains a termination signal. Any nucleotide sequence that contains one or more termination signals is removed from the list generating an updated list. In some embodiments, the termination signal has the following nucleotide sequence: $5'\text{-}X_1ATCTX_2TX_{3\text{-}3}'$, wherein $X_1$, $X_2$ and $X_3$ are independently selected from A, C, T or G. In some embodiments, the termination signal has one of the following nucleotide sequences: TATCTGTT; and/or TTTTTT; and/or AAGCTT; and/or GAAGAGC; and/or TCTAGA. In some embodiments, the termination signal has the following nucleotide sequence: $5'\text{-}X_1AUCUX_2UX_{3\text{-}3}'$, wherein $X_1$, $X_2$ and $X_3$ are independently selected from A, C, U or G. In some embodiments, the termination signal has one of the following nucleotide sequences: UAUCUGUU; and/or UUUUUU; and/or AAGCUU; and/or GAAGAGC; and/or UCUAGA.

Guanine-Cytosine (GC) Content

The method further comprises determining a guanine-cytosine (GC) content of each of the optimized nucleotide sequences in the updated list of optimized nucleotide sequences. The GC content of a sequence is the percentage of bases in the nucleotide sequence that are guanine or cytosine. The list of optimized nucleotide sequences is further updated by removing any nucleotide sequence from the list, if its GC content falls outside a predetermined GC content range.

Determining a GC content of each of the optimized nucleotide sequences comprises, for each nucleotide sequence: determining a GC content of one or more additional portions of the nucleotide sequence, wherein the additional portions are non-overlapping with each other and with the first portion, and wherein updating the list of optimized sequences comprises: removing the nucleotide sequence if the GC content of any portion falls outside the predetermined GC content range, optionally wherein determining the GC content of the nucleotide sequence is halted when the GC content of any portion is determined to be outside the predetermined GC content range. In some embodiments, the first portion and/or the one or more additional portions of the nucleotide sequence comprise a predetermined number of nucleotides, optionally wherein the predetermined number of nucleotides is in the range of: 5 to 300 nucleotides, or 10 to 200 nucleotides, or 15 to 100 nucleotides, or 20 to 50 nucleotides. In the context of the present invention, the predetermined number of nucleotides is typically 30 nucleotides. The predetermined GC content range can be 15%-75%, or 40%-60%, or, 30%-70%. In the context of the present invention, the predetermined GC content range is typically 30%-70%.

A suitable GC content filter in the context of the invention may first analyze the first 30 nucleotides of the optimized nucleotide sequence, i.e., nucleotides 1 to 30 of the optimized nucleotide sequence. Analysis may comprise determining the number of nucleotides in the portion with are either G or C, and determining the GC content of the portion may comprise dividing the number of G or C nucleotides in the portion by the total number of nucleotides in the portion. The result of this analysis will provide a value describing the proportion of nucleotides in the portion that are G or C, and may be a percentage, for example 50%, or a decimal, for example 0.5. If the GC content of the first portion falls outside a predetermined GC content range, the optimized nucleotide sequence may be removed from the list of optimized nucleotide sequences.

If the GC content of the first portion falls inside the predetermined GC content range, the GC content filter may then analyze a second portion of the optimized nucleotide sequence. In this example, this may be the second 30 nucleotides, i.e., nucleotides 31 to 60, of the optimized nucleotide sequence. The portion analysis may be repeated for each portion until either: a portion is found having a GC content falling outside the predetermined GC content range, in which case the optimized nucleotide sequence may be removed from the list, or the whole optimized nucleotide sequence has been analyzed and no such portion has been found, in which case the GC content filter retains the optimized nucleotide sequence in the list and may move on to the next optimized nucleotide sequence in the list.

Codon Adaptation Index (CAI)

The method further comprises determining a codon adaptation index of each of the optimized nucleotide sequences in the most recently updated list of optimized nucleotide sequences. The codon adaptation index of a sequence is a measure of codon usage bias and can be a value between 0 and 1. The most recently updated list of optimized nucleotide sequences is further updated by removing any nucleotide sequence if its codon adaptation index is less than or equal to a predetermined codon adaptation index threshold. The codon adaptation index threshold can 0.7, or 0.75, or 0.8, or 0.85, or 0.9. The inventors have found that optimized nucleotide sequences with a codon adaptation index equal to or greater than 0.8 deliver very high protein yield. Therefore in the context of the invention, the codon adaptation index threshold is typically 0.8.

A codon adaptation index may be calculated, for each optimized nucleotide sequence, in any way that would be apparent to a person skilled in the art, for example as described in "*The codon adaptation index—a measure of directional synonymous codon usage bias, and its potential applications*" (Sharp and Li, 1987. *Nucleic Acids Research* 15(3), p. 1281-1295); available online at https://www.ncbi.nlm.nih.gov/pmc/articles/PMC340524/.

Implementing a codon adaptation index calculation may include a method according to, or similar to, the following. For each amino acid in a sequence, a weight of each codon in a sequence may be represented by a parameter termed relative adaptiveness ($w_i$). Relative adaptiveness may be computed from a reference sequence set, as the ratio between the observed frequency of the codon $f_i$ and the frequency of the most frequent synonymous codon $f_j$ for that amino acid. The codon adaptation index of a sequence may then be calculated as the geometric mean of the weight associated to each codon over the length of the sequence (measured in codons). The reference sequence set used to calculate codon adaptation index may be the same reference sequence set from which a codon usage table used with methods of the invention is derived.

In some embodiments, a suitable codon optimized mRNA sequence is an mRNA sequence encoding a human CFTR (hCFTR) protein of SEQ ID NO:1.

TABLE 1

| Exemplary Codon-Optimized Human CFTR |
| --- |
| Human CFTR Protein Sequence | MQRSPLEKASVVSKLFFSWTRPILRKGYRQ<br>RLELSDIYQIPSVDSADNLSEKLEREWDRE<br>LASKKNPKLINALRRCFFWRFMFYGIFLYL<br>GEVTKAVQPLLLGRIIASYDPDNKEERSIA<br>IYLGIGLCLLFIVRTLLLHPAIFGLHHIGM<br>QMRIAMFSLIYKKTLKLSSRVLDKISIGQL<br>VSLLSNNLNKFDEGLALAHFVWIAPLQVAL<br>LMGLIWELLQASAFCGLGFLIVLALFQAGL<br>GRMMMKYRDQRAGKISERLVITSEMIENIQ<br>SVKAYCWEEAMEKMIENLRQTELKLTRKAA<br>YVRYFNSSAFFFSGFFVVFLSVLPYALIKG<br>IILRKIFTTISFCIVLRMAVTRQFPWAVQT<br>WYDSLGAINKIQDFLQKQEYKTLEYNLTTT<br>EVVMENVTAFWEEGFGELFEKAKQNNNNRK<br>TSNGDDSLFFSNFSLLGTPVLKDINFKIER<br>GQLLAVAGSTGAGKTSLLMVIMGELEPSEG<br>KIKHSGRISFCSQFSWIMPGTIKENIIFGV<br>SYDEYRYRSVIKACQLEEDISKFAEKDNIV<br>LGEGGITLSGGQRARISLARAVYKDADLYL<br>LDSPFGYLDVLTEKEIFESCVCKLMANKTR<br>ILVTSKMEHLKKADKILILHEGSSYFYGTF<br>SELQNLQPDFSSKLMGCDSFDQFSAERRNS<br>ILTETLHRFSLEGDAPVSWTETKKQSFKQT<br>GEFGEKRKNSILNPINSIRKFSIVQKTPLQ<br>MNGIEEDSDEPLERRLSLVPDSEQGEAILP<br>RISVISTGPTLQARRRQSVLNLMTHSVNQG<br>QNIHRKTTASTRKVSLAPQANLTELDIYSR<br>RLSQETGLEISEEINEEDLKECFFDDMESI<br>PAVTTWNTYLRYITVHKSLIFVLIWCLVIF<br>LAEVAASLVVLWLLGNTPLQDKGNSTHSRN<br>NSYAVIITSTSSYYVFYIYVGVADTLLAMG<br>FFRGLPLVHTLITVSKILHHKMLHSVLQAP<br>MSTLNTLKAGGILNRFSKDIAILDDLLPLT<br>IFDFIQLLLIVIGAIAVVAVLQPYIFVATV<br>PVIVAFIMLRAYFLQTSQQLKQLESEGRSP<br>IFTHLVTSLKGLWTLRAFGRQPYFETLFHK<br>ALNLHTANWFLYLSTLRWFQMRIEMIFVIF<br>FIAVTFISILTTGEGEGRVGIILTLAMNIM<br>STLQWAVNSSIDVDSLMRSVSRVFKFIDMP<br>TEGKPTKSTKPYKNGQLSKVMIIENSHVKK<br>DDIWPSGGQMTVKDLTAKYTEGGNAILENI<br>SFSISPGQRVGLLGRTGSGKSTLLSAFLRL<br>LNTEGEIQIDGVSWDSITLQQWRKAFGVIP<br>QKVFIFSGTFRKNLDPYEQWSDQEIWKVAD<br>EVGLRSVIEQFPGKLDFVLVDGGCVLSHGH<br>KQLMCLARSVLSKAKILLLDEPSAHLDPVT<br>YQIIRRTLKQAFADCTVILCEHRIEAMLEC<br>QQFLVIEENKVRQYDSIQKLLNERSLFRQA<br>ISPSDRVKLFPHRNSSKCKSKPQIAALKEE<br>TEEEVQDTRL<br>(SEQ ID NO: 1) |

In some embodiments, a suitable mRNA may be a codon-optimized sequence, as shown in SEQ ID NO: 2-11.

In some embodiments, a suitable mRNA sequence may be an mRNA sequence a homolog or an analog of human CFTR protein. For example, a homolog or an analog of human CFTR protein may be a modified human CFTR protein containing one or more amino acid substitutions, deletions, and/or insertions as compared to a wild-type or naturally-occurring human CFTR protein while retaining substantial CFTR protein activity. In some embodiments, an mRNA suitable for the present invention encodes an amino acid sequence at least 70%, 75%, 80%, 85%, 90%, 91%, 92%, 93%, 94%, 95%, 96%, 97%, 98%, 99% or more homologous to SEQ ID NO: 1. In some embodiments, an mRNA suitable for the present invention encodes a protein substantially identical to human CFTR protein. In some embodiments, an mRNA suitable for the present invention encodes an amino acid sequence at least 70%, 75%, 80%, 85%, 90%, 91%, 92%, 93%, 94%, 95%, 96%, 97%, 98%, 99% or more identical to SEQ ID NO: 1. Typically, an mRNA according to the present invention encodes a CFTR protein with an amino acid sequence that is identical to SEQ ID NO: 1.

In some embodiments, an mRNA suitable for the present invention encodes a fragment or a portion of human CFTR protein. In some embodiments, an mRNA suitable for the present invention encodes a fragment or a portion of human CFTR protein, wherein the fragment or portion of the protein still maintains CFTR activity similar to that of the wild-type protein.

In some embodiments, a suitable mRNA encodes a fusion protein comprising a full length, fragment or portion of a CFTR protein fused to another protein (e.g., an N or C terminal fusion). In some embodiments, the protein fused to the mRNA encoding a full length, fragment or portion of a CFTR protein encodes a signal or a cellular targeting sequence.

In some embodiments, an mRNA suitable for the present invention comprises a nucleotide sequence at least 80%, 85%, 90%, 91%, 92%, 93%, 94%, 95%, 96%, 97%, 98%, 99% or more identical to SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, or SEQ ID NO: 11.

Synthesis of mRNA mRNAs according to the present invention may be synthesized according to any of a variety of known methods. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application.

Exemplary Codon-Optimized Human Cystic Fibrosis Transmembrane Conductance Regulator (CFTR) mRNAs

```
Construct design:
X-SEQ ID NO: 1-Y
5' and 3' UTR Sequences:
X (5' UTR Sequence) =
                              (SEQ ID NO: 12)
GGACAGAUCGCCUGGAGACGCCAUCCACGCUGUUU

UGACCUCCAUAGAAGACACCGGGACCGAUCCAGCC

UCCGCGGCCGGGAACGGUGCAUUGGAACGCGGAUU

CCCCGUGCCAAGAGUGACUCACCGUCCUUGACACG

Y (3' UTR Sequence) =
                              (SEQ ID NO: 13)
CGGGUGGCAUCCCUGUGACCCCUCCCCAGUGCCUC

UCCUGGCCCUGGAAGUUGCCACUCCAGUGCCCACC

AGCCUUGUCCUAAUAAAAUUAAGUUGCAUCAAGCU
OR (SEQ ID NO: 14)
GGGUGGCAUCCCUGUGACCCCUCCCCAGUGCCUCU

CCUGGCCCUGGAAGUUGCCACUCCAGUGCCCACCA

GCCUUGUCCUAAUAAAAUUAAGUUGCAUCAAAGCU
```

An exemplary codon-optimized human CFTR mRNA sequence includes any one of SEQ ID NO: 2 to SEQ ID NO: 11 as described in the detailed description section.

In some embodiments, an activity of CFTR proteins is evaluated by an Ussing chamber assay. In some embodiments, duration of activity of CFTR proteins is evaluated by time-course Ussing assays. In some embodiments, protein expression and stability are evaluated by pulse-chase methods. In some embodiments, protein expression and stability are evaluated by surface biotinylation.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Synthesis of mRNA Using SP6 RNA Polymerase

In some embodiments; CFTR mRNA is produced using SP6 RNA Polymerase. SP6 RNA Polymerase is a DNA-dependent RNA polymerase with high sequence specificity for SP6 promoter sequences. The SP6 polymerase catalyzes the 5'—>3' in vitro synthesis of RNA on either single-stranded DNA or double-stranded DNA downstream from its promoter; it incorporates native ribonucleotides and/or modified ribonucleotides and/or labeled ribonucleotides into the polymerized transcript. Examples of such labeled ribonucleotides include biotin-, fluorescein-, digoxigenin-, aminoallyl-, and isotope-labeled nucleotides.

The sequence for bacteriophage SP6 RNA polymerase was initially described (GenBank. Y00105.1) as having the following amino acid sequence:

```
                              (SEQ ID NO: 17)
MQDLHAIQLQLEEEMFNGGIRRFEADQQRQIAAGS

ESDTAWNRRLLSELIAPMAEGIQAYKEEYEGKKGR

APRALAFLQCVENEVAAYITMKVVMDMLNTDATLQ

AIAMSVAERIEDQVRFSKLEGHAAKYFEKVKKSLK

ASRTKSYRHAHNVAVVAEKSVAEKDADFDRWEAWP

KETQLQIGTTLLEILEGSVFYNGEPVFMRAMRTYG

GKTIYYLQTSESVGQWISAFKEHVAQLSPAYAPCV

IPPRPWRTPFNGGFHTEKVASRIRLVKGNREHVRK

LTQKQMPKVYKAINALQNTQWQINKDVLAVIEEVI

RLDLGYGVPSFKPLIDKENKPANPVPVEFQHLRGR

ELKEMLSPEQWQQFINWKGECARLYTAETKRGSKS

AAVVRMVGQARKYSAFESIYFVYAMDSRSRVYVQS

STLSPQSNDLGKALLRFTEGRPVNGVEALKWFCIN

GANLWGWDKKTFDVRVSNVLDEEFQDMCRDIAADP

LTFTQWAKADAPYEFLAWCFEYAQYLDLVDEGRAD

EFRTHLPVHQDGSCSGIQHYSAMLRDEVGAKAVNL

KPSDAPQDIYGAVAQVVIKKNALYMDADDATTFTS

GSVTLSGTELRAMASAWDSIGITRSLTKKPVMTLP

YGSTRLTCRESVIDYIVDLEEKEAQKAVAEGRTAN

KVHPFEDDRQDYLTPGAAYNYMTALIWPSISEVVK
```

-continued

APIVAMKMIRQLARFAAKRNEGLMYTLPTGFILEQ

KIMATEMLRVRTCLMGDIKMSLQVETDIVDEAAMM

GAAAPNFVHGHDASHLILTVCELVDKGVTSIAVIH

DSFGTHADNTLTLRVALKGQMVAMYIDGNALQKLL

EEHEVRWMVDTGIEVPEQGEFDLNEIMDSEYVFA.

An SP6 RNA polymerase suitable for the present invention can be any enzyme having substantially the same polymerase activity as bacteriophage SP6 RNA polymerase. Thus, in some embodiments, an SP6 RNA polymerase suitable for the present invention may be modified from SEQ ID NO: 17. For example, a suitable SP6 RNA polymerase may contain one or more amino acid substitutions, deletions, or additions. In some embodiments, a suitable SP6 RNA polymerase has an amino acid sequence about 99%, 98%, 97%, 96%, 95%, 94%, 93%, 92%, 91%, 90%, 89%, 88%, 87%, 86%, 85%, 84%, 83%, 82%, 81%, 80%, 75%, 70%, 65%, or 60% identical or homologous to SEQ ID NO: 17. In some embodiments, a suitable SP6 RNA polymerase may be a truncated protein (from N-terminus, C-terminus, or internally) but retain the polymerase activity. In some embodiments, a suitable SP6 RNA polymerase is a fusion protein.

An SP6 RNA polymerase suitable for the invention may be a commercially-available product, e.g., from Aldevron, Ambion, New England Biolabs (NEB), Promega, and Roche. The SP6 may be ordered and/or custom designed from a commercial source or a non-commercial source according to the amino acid sequence of SEQ ID NO: 17 or a variant of SEQ ID NO: 17 as described herein. The SP6 may be a standard-fidelity polymerase or may be a high-fidelity/high-efficiency/high-capacity which has been modified to promote RNA polymerase activities, e.g., mutations in the SP6 RNA polymerase gene or post-translational modifications of the SP6 RNA polymerase itself. Examples of such modified SP6 include SP6 RNA Polymerase-Plus™ from Ambion, HiScribe SP6 from NEB, and RiboMAX™ and Riboprobe® Systems from Promega.

In some embodiments, a suitable SP6 RNA polymerase is a fusion protein. For example, an SP6 RNA polymerase may include one or more tags to promote isolation, purification, or solubility of the enzyme. A suitable tag may be located at the N-terminus, C-terminus, and/or internally. Non-limiting examples of a suitable tag include Calmodulin-binding protein (CBP); *Fasciola hepatica* 8-kDa antigen (Fh8); FLAG tag peptide; glutathione-S-transferase (GST); Histidine tag (e.g., hexahistidine tag (His6)); maltose-binding protein (MBP); N-utilization substance (NusA); small ubiquitin related modifier (SUMO) fusion tag; Streptavidin binding peptide (STREP); Tandem affinity purification (TAP); and thioredoxin (TrxA). Other tags may be used in the present invention. These and other fusion tags have been described, e.g., Costa et al. Frontiers in Microbiology 5 (2014): 63 and in PCT/US16/57044, the contents of which are incorporated herein by reference in their entireties. In certain embodiments, a His tag is located at SP6's N-terminus.

DNA Template

Typically, a CFTR DNA template is either entirely double-stranded or mostly single-stranded with a double-stranded SP6 promoter sequence.

Linearized plasmid DNA (linearized via one or more restriction enzymes), linearized genomic DNA fragments (via restriction enzyme and/or physical means), PCR products, and/or synthetic DNA oligonucleotides can be used as templates for in vitro transcription with SP6, provided that they contain a double-stranded SP6 promoter upstream (and in the correct orientation) of the DNA sequence to be transcribed.

In some embodiments, the linearized DNA template has a blunt-end.

In some embodiments, the DNA sequence to be transcribed may be optimized to facilitate more efficient transcription and/or translation. For example, the DNA sequence may be optimized regarding cis-regulatory elements (e.g., TATA box, termination signals, and protein binding sites), artificial recombination sites, chi sites, CpG dinucleotide content, negative CpG islands, GC content, polymerase slippage sites, and/or other elements relevant to transcription; the DNA sequence may be optimized regarding cryptic splice sites, mRNA secondary structure, stable free energy of mRNA, repetitive sequences, RNA instability motif, and/or other elements relevant to mRNA processing and stability; the DNA sequence may be optimized regarding codon usage bias, codon adaptability, internal chi sites, ribosomal binding sites (e.g., IRES), premature polyA sites, Shine-Dalgarno (SD) sequences, and/or other elements relevant to translation; and/or the DNA sequence may be optimized regarding codon context, codon-anticodon interaction, translational pause sites, and/or other elements relevant to protein folding. Optimization methods known in the art may be used in the present invention, e.g., GeneOptimizer by ThermoFisher and OptimumGene™, which are described in US 20110081708, the contents of which are incorporated herein by reference in its entirety.

In some embodiments, the DNA template includes a 5' and/or 3' untranslated region. In some embodiments, a 5' untranslated region includes one or more elements that affect an mRNA's stability or translation, for example, an iron responsive element. In some embodiments, a 5' untranslated region may be between about 50 and 500 nucleotides in length.

In some embodiments, a 3' untranslated region includes one or more of a polyadenylation signal, a binding site for proteins that affect an mRNA's stability of location in a cell, or one or more binding sites for miRNAs. In some embodiments, a 3' untranslated region may be between 50 and 500 nucleotides in length or longer.

Exemplary 3' and/or 5' UTR sequences can be derived from mRNA molecules which are stable (e.g., globin, actin, GAPDH, tubulin, histone, or citric acid cycle enzymes) to increase the stability of the sense mRNA molecule. For example, a 5' UTR sequence may include a partial sequence of a CMV immediate-early 1 (IE1) gene, or a fragment thereof to improve the nuclease resistance and/or improve the half-life of the polynucleotide. Also contemplated is the inclusion of a sequence encoding human growth hormone (hGH), or a fragment thereof to the 3' end or untranslated region of the polynucleotide (e.g., mRNA) to further stabilize the polynucleotide. Generally, these modifications improve the stability and/or pharmacokinetic properties (e.g., half-life) of the polynucleotide relative to their unmodified counterparts, and include, for example modifications made to improve such polynucleotides' resistance to in vivo nuclease digestion.

Large-Scale mRNA Synthesis

The present invention relates to large-scale production of codon optimized CFTR mRNA. In some embodiments, a method according to the invention synthesizes mRNA at least 100 mg, 150 mg, 200 mg, 300 mg, 400 mg, 500 mg, 600 mg, 700 mg, 800 mg, 900 mg, 1 g, 5 g, 10 g, 25 g, 50 g, 75 g, 100 g, 250 g, 500 g, 750 g, 1 kg, 5 kg, 10 kg, 50 kg, 100 kg, 1000 kg, or more at a single batch. As used herein, the term "batch" refers to a quantity or amount of mRNA synthesized at one time, e.g., produced according to a single manufacturing setting. A batch may refer to an amount of mRNA synthesized in one reaction that occurs via a single aliquot of enzyme and/or a single aliquot of DNA template for continuous synthesis under one set of conditions. mRNA synthesized at a single batch would not include mRNA synthesized at different times that are combined to achieve the desired amount. Generally, a reaction mixture includes SP6 RNA polymerase, a linear DNA template, and an RNA polymerase reaction buffer (which may include ribonucleotides or may require addition of ribonucleotides).

According to the present invention, 1-100 mg of SP6 polymerase is typically used per gram (g) of mRNA produced. In some embodiments, about 1-90 mg, 1-80 mg, 1-60 mg, 1-50 mg, 1-40 mg, 10-100 mg, 10-80 mg, 10-60 mg, 10-50 mg of SP6 polymerase is used per gram of mRNA produced. In some embodiments, about 5-20 mg of SP6 polymerase is used to produce about 1 gram of mRNA. In some embodiments, about 0.5 to 2 grams of SP6 polymerase is used to produce about 100 grams of mRNA. In some embodiments, about 5 to 20 grams of SP6 polymerase is used to about 1 kilogram of mRNA. In some embodiments, at least 5 mg of SP6 polymerase is used to produce at least 1 gram of mRNA. In some embodiments, at least 500 mg of SP6 polymerase is used to produce at least 100 grams of mRNA. In some embodiments, at least 5 grams of SP6 polymerase is used to produce at least 1 kilogram of mRNA. In some embodiments, about 10 mg, 20 mg, 30 mg, 40 mg, 50 mg, 60 mg, 70 mg, 80 mg, 90 mg, or 100 mg of plasmid DNA is used per gram of mRNA produced. In some embodiments, about 10-30 mg of plasmid DNA is used to produce about 1 gram of mRNA. In some embodiments, about 1 to 3 grams of plasmid DNA is used to produce about 100 grams of mRNA. In some embodiments, about 10 to 30 grams of plasmid DNA is used to about 1 kilogram of mRNA. In some embodiments, at least 10 mg of plasmid DNA is used to produce at least 1 gram of mRNA. In some embodiments, at least 1 gram of plasmid DNA is used to produce at least 100 grams of mRNA. In some embodiments, at least 10 grams of plasmid DNA is used to produce at least 1 kilogram of mRNA.

In some embodiments, the concentration of the SP6 RNA polymerase in the reaction mixture may be from about 1 to 100 nM, 1 to 90 nM, 1 to 80 nM, 1 to 70 nM, 1 to 60 nM, 1 to 50 nM, 1 to 40 nM, 1 to 30 nM, 1 to 20 nM, or about 1 to 10 nM. In certain embodiments, the concentration of the SP6 RNA polymerase is from about 10 to 50 nM, 20 to 50 nM, or 30 to 50 nM. A concentration of 100 to 10000 Units/ml of the SP6 RNA polymerase may be used, as examples, concentrations of 100 to 9000 Units/ml, 100 to 8000 Units/ml, 100 to 7000 Units/ml, 100 to 6000 Units/ml, 100 to 5000 Units/ml, 100 to 1000 Units/ml, 200 to 2000 Units/ml, 500 to 1000 Units/ml, 500 to 2000 Units/ml, 500 to 3000 Units/ml, 500 to 4000 Units/ml, 500 to 5000 Units/ml, 500 to 6000 Units/ml, 1000 to 7500 Units/ml, and 2500 to 5000 Units/ml may be used.

The concentration of each ribonucleotide (e.g., ATP, UTP, GTP, and CTP) in a reaction mixture is between about 0.1 mM and about 10 mM, e.g., between about 1 mM and about 10 mM, between about 2 mM and about 10 mM, between about 3 mM and about 10 mM, between about 1 mM and about 8 mM, between about 1 mM and about 6 mM, between about 3 mM and about 10 mM, between about 3 mM and about 8 mM, between about 3 mM and about 6 mM, between about 4 mM and about 5 mM. In some embodiments, each ribonucleotide is at about 5 mM in a reaction mixture. In some embodiments, the total concentration of rNTPs (for example, ATP, GTP, CTP and UTPs combined) used in the reaction range between 1 mM and 40 mM. In some embodiments, the total concentration of rNTPs (for example, ATP, GTP, CTP and UTPs combined) used in the reaction range between 1 mM and 30 mM, or between 1 mM and 28 mM, or between 1 mM to 25 mM, or between 1 mM and 20 mM. In some embodiments, the total rNTPs concentration is less than 30 mM. In some embodiments, the total rNTPs concentration is less than 25 mM. In some embodiments, the total rNTPs concentration is less than 20 mM. In some embodiments, the total rNTPs concentration is less than 15 mM. In some embodiments, the total rNTPs concentration is less than 10 mM.

The RNA polymerase reaction buffer typically includes a salt/buffering agent, e.g., Tris, HEPES, ammonium sulfate, sodium bicarbonate, sodium citrate, sodium acetate, potassium phosphate sodium phosphate, sodium chloride, and magnesium chloride.

The pH of the reaction mixture may be between about 6 to 8.5, from 6.5 to 8.0, from 7.0 to 7.5, and in some embodiments, the pH is 7.5.

Linear or linearized DNA template (e.g., as described above and in an amount/concentration sufficient to provide a desired amount of RNA), the RNA polymerase reaction buffer, and SP6 RNA polymerase are combined to form the reaction mixture. The reaction mixture is incubated at between about 37° C. and about 42° C. for thirty minutes to six hours, e.g., about sixty to about ninety minutes.

In some embodiments, about 5 mM NTPs, about 0.05 mg/mL SP6 polymerase, and about 0.1 mg/ml DNA template in a suitable RNA polymerase reaction buffer (final reaction mixture pH of about 7.5) is incubated at about 37° C. to about 42° C. for sixty to ninety minutes.

In some embodiments, a reaction mixture contains linearized double stranded DNA template with an SP6 polymerase-specific promoter, SP6 RNA polymerase, RNase inhibitor, pyrophosphatase, 29 mM NTPs, 10 mM DTT and a reaction buffer (when at 10× is 800 mM HEPES, 20 mM spermidine, 250 mM MgCl$_2$, pH 7.7) and quantity sufficient (QS) to a desired reaction volume with RNase-free water; this reaction mixture is then incubated at 37° C. for 60 minutes. The polymerase reaction is then quenched by addition of DNase I and a DNase I buffer (when at 10× is 100 mM Tris-HCl, 5 mM MgCl$_2$ and 25 mM CaCl$_2$, pH 7.6) to facilitate digestion of the double-stranded DNA template in preparation for purification. This embodiment has been shown to be sufficient to produce 100 grams of mRNA.

In some embodiments, a reaction mixture includes NTPs at a concentration ranging from 1-10 mM, DNA template at a concentration ranging from 0.01-0.5 mg/ml, and SP6 RNA polymerase at a concentration ranging from 0.01-0.1 mg/ml, e.g., the reaction mixture comprises NTPs at a concentration of 5 mM, the DNA template at a concentration of 0.1 mg/ml, and the SP6 RNA polymerase at a concentration of 0.05 mg/ml.

Nucleotides

Various naturally-occurring or modified nucleosides may be used to product mRNA according to the present invention. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, the mRNA comprises one or more nonstandard nucleotide residues. The nonstandard nucleotide residues may include, e.g., 5-methyl-cytidine ("5mC"), pseudouridine ("yU"), and/or 2-thio-uridine ("2sU"). See, e.g., U.S. Pat. No. 8,278,036 or WO2011012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US20120195936 and international publication WO2011012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Some embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In some embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

Post-Synthesis Processing

Typically, a 5' cap and/or a 3' tail may be added after the synthesis. The presence of the cap is important in providing resistance to nucleases found in most eukaryotic cells. The presence of a "tail" serves to protect the mRNA from exonuclease degradation.

A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G. Additional cap structures are described in published US Application No. US 2016/0032356 and U.S. Provisional Application 62/464,327, filed Feb. 27, 2017, which are incorporated herein by reference.

Typically, a tail structure includes a poly(A) and/or poly (C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, at least 950 adenosine or cytosine nucleotides, or at least 1 kb adenosine or cytosine nucleotides, respectively. In some embodiments, a poly A or poly C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly (A) and poly (C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

As described herein, the addition of the 5' cap and/or the 3' tail facilitates the detection of abortive transcripts generated during in vitro synthesis because without capping and/or tailing, the size of those prematurely aborted mRNA transcripts can be too small to be detected. Thus, in some embodiments, the 5' cap and/or the 3' tail are added to the synthesized mRNA before the mRNA is tested for purity (e.g., the level of abortive transcripts present in the mRNA). In some embodiments, the 5' cap and/or the 3' tail are added to the synthesized mRNA before the mRNA is purified as described herein. In other embodiments, the 5' cap and/or the 3' tail are added to the synthesized mRNA after the mRNA is purified as described herein.

mRNA synthesized according to the present invention may be used without further purification. In particular, mRNA synthesized according to the present invention may be used without a step of removing shortmers. In some embodiments, mRNA synthesized according to the present invention may be further purified. Various methods may be used to purify mRNA synthesized according to the present invention. For example, purification of mRNA can be performed using centrifugation, filtration and/or chromatographic methods. In some embodiments, the synthesized mRNA is purified by ethanol precipitation or filtration or chromatography, or gel purification or any other suitable means. In some embodiments, the mRNA is purified by HPLC. In some embodiments, the mRNA is extracted in a standard phenol: chloroform: isoamyl alcohol solution, well known to one of skill in the art. In some embodiments, the mRNA is purified using Tangential Flow Filtration. Suitable purification methods include those described in US 2016/0040154, US 2015/0376220, PCT application PCT/US18/19954 entitled "METHODS FOR PURIFICATION OF MESSENGER RNA" filed on Feb. 27, 2018, and PCT application PCT/US18/19978 entitled "METHODS FOR PURIFICATION OF MESSENGER RNA" filed on Feb. 27, 2018, all of which are incorporated by reference herein and may be used to practice the present invention.

In some embodiments, the mRNA is purified before capping and tailing. In some embodiments, the mRNA is purified after capping and tailing. In some embodiments, the mRNA is purified both before and after capping and tailing.

In some embodiments, the mRNA is purified either before or after or both before and after capping and tailing, by centrifugation.

In some embodiments, the mRNA is purified either before or after or both before and after capping and tailing, by filtration.

In some embodiments, the mRNA is purified either before or after or both before and after capping and tailing, by Tangential Flow Filtration (TFF).

In some embodiments, the mRNA is purified either before or after or both before and after capping and tailing by chromatography.

Characterization of mRNA

Full-length or abortive transcripts of mRNA may be detected and quantified using any methods available in the art. In some embodiments, the synthesized mRNA molecules are detected using blotting, capillary electrophoresis, chromatography, fluorescence, gel electrophoresis, HPLC, silver stain, spectroscopy, ultraviolet (UV), or UPLC, or a combination thereof. Other detection methods known in the art are included in the present invention. In some embodiments, the synthesized mRNA molecules are detected using UV absorption spectroscopy with separation by capillary electrophoresis. In some embodiments, mRNA is first denatured by a Glyoxal dye before gel electrophoresis ("Glyoxal gel electrophoresis"). In some embodiments, synthesized mRNA is characterized before capping or tailing. In some embodiments, synthesized mRNA is characterized after capping and tailing.

In some embodiments, mRNA generated by the method disclosed herein comprises less than 10%, less than 9%, less than 8%, less than 7%, less than 6%, less than 5%, less than 4%, less than 3%, less than 2%, less than 1%, less than 0.5%, less than 0.1% impurities other than full length mRNA. The impurities include IVT contaminants, e.g., proteins, enzymes, free nucleotides and/or shortmers.

In some embodiments, mRNA produced according to the invention is substantially free of shortmers or abortive transcripts. In particular, mRNA produced according to the invention contains undetectable level of shortmers or abortive transcripts by capillary electrophoresis or Glyoxal electrophoresis. As used herein, the term "shortmers" or "abortive transcripts" refers to any transcripts that are less than full-length. In some embodiments, "shortmers" or "abortive transcripts" are less than 100 nucleotides in length, less than 90, less than 80, less than 70, less than 60, less than 50, less than 40, less than 30, less than 20, or less than 10 nucleotides in length. In some embodiments, shortmers are detected or quantified after adding a 5'-cap, and/or a 3'-poly A tail.

mRNA Solution

In some embodiments, mRNA may be provided in a solution to be mixed with a lipid solution such that the mRNA may be encapsulated in lipid nanoparticles. A suitable mRNA solution may be any aqueous solution containing mRNA to be encapsulated at various concentrations. For example, a suitable mRNA solution may contain an mRNA at a concentration of or greater than about 0.01 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml. In some embodiments, a suitable mRNA solution may contain an mRNA at a concentration ranging from about 0.01-1.0 mg/ml, 0.01-0.9 mg/ml, 0.01-0.8 mg/ml, 0.01-0.7 mg/ml, 0.01-0.6 mg/ml, 0.01-0.5 mg/ml, 0.01-0.4 mg/ml, 0.01-0.3 mg/ml, 0.01-0.2 mg/ml, 0.01-0.1 mg/ml, 0.05-1.0 mg/ml, 0.05-0.9 mg/ml, 0.05-0.8 mg/ml, 0.05-0.7 mg/ml, 0.05-0.6 mg/ml, 0.05-0.5 mg/ml, 0.05-0.4 mg/ml, 0.05-0.3 mg/ml, 0.05-0.2 mg/ml, 0.05-0.1 mg/ml, 0.1-1.0 mg/ml, 0.2-0.9 mg/ml, 0.3-0.8 mg/ml, 0.4-0.7 mg/ml, or 0.5-0.6 mg/ml. In some embodiments, a suitable mRNA solution may contain an mRNA at a concentration up to about 5.0 mg/ml, 4.0 mg/ml, 3.0 mg/ml, 2.0 mg/ml, 1.0 mg/ml, 0.09 mg/ml, 0.08 mg/ml, 0.07 mg/ml, 0.06 mg/ml, or 0.05 mg/ml.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate. In some embodiments, suitable concentration of the buffering agent may range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM. In some embodiments, suitable concentration of the buffering agent is or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM.

Exemplary salts can include sodium chloride, magnesium chloride, and potassium chloride. In some embodiments, suitable concentration of salts in an mRNA solution may range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM. Salt concentration in a suitable mRNA solution is or greater than about 1 mM, 5 mM, 10 mM, 20 mM, 30 mM, 40 mM, 50 mM, 60 mM, 70 mM, 80 mM, 90 mM, or 100 mM.

In some embodiments, a suitable mRNA solution may have a pH ranging from about 3.5-6.5, 3.5-6.0, 3.5-5.5., 3.5-5.0, 3.5-4.5, 4.0-5.5, 4.0-5.0, 4.0-4.9, 4.0-4.8, 4.0-4.7, 4.0-4.6, or 4.0-4.5. In some embodiments, a suitable mRNA solution may have a pH of or no greater than about 3.5, 4.0, 4.1, 4.2, 4.3, 4.4, 4.5, 4.6, 4.7, 4.8, 4.9, 5.0, 5.2, 5.4, 5.6, 5.8, 6.0, 6.1, 6.3, and 6.5.

Various methods may be used to prepare an mRNA solution suitable for the present invention. In some embodiments, mRNA may be directly dissolved in a buffer solution described herein. In some embodiments, an mRNA solution may be generated by mixing an mRNA stock solution with a buffer solution prior to mixing with a lipid solution for encapsulation. In some embodiments, an mRNA solution may be generated by mixing an mRNA stock solution with a buffer solution immediately before mixing with a lipid solution for encapsulation. In some embodiments, a suitable mRNA stock solution may contain mRNA in water at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, an mRNA stock solution is mixed with a buffer solution using a pump. Exemplary pumps include but are not limited to gear pumps, peristaltic pumps and centrifugal pumps.

Typically, the buffer solution is mixed at a rate greater than that of the mRNA stock solution. For example, the buffer solution may be mixed at a rate at least 1×, 2×, 3×, 4×, 5×, 6×, 7×, 8×, 9×, 10×, 15×, or 20× greater than the rate of the mRNA stock solution. In some embodiments, a buffer solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffer solution is mixed at a flow rate of or greater than about 60 ml/minute, 100 ml/minute, 140 ml/minute, 180 ml/minute, 220 ml/minute, 260 ml/minute, 300 ml/minute, 340 ml/minute, 380 ml/minute, 420 ml/minute, 480 ml/minute, 540 ml/minute, 600 ml/minute, 1200 ml/minute, 2400 ml/minute, 3600 ml/minute, 4800 ml/minute, or 6000 ml/minute.

In some embodiments, an mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 ml/minute, about 360-480 ml/minute, or about 480-600 ml/minute). In some embodiments, an mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 60 ml/minute, 80 ml/minute, 100 ml/minute, 200 ml/minute, 300 ml/minute, 400 ml/minute, 500 ml/minute, or 600 ml/minute.

Delivery Vehicles

According to the present invention, mRNA encoding a CFTR protein (e.g., a full length, fragment, or portion of a CFTR protein) as described herein may be delivered as naked RNA (unpackaged) or via delivery vehicles. As used herein, the terms "delivery vehicle," "transfer vehicle," "nanoparticle" or grammatical equivalent, are used interchangeably.

Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

In some embodiments, a delivery vehicle comprising CFTR mRNA is administered by pulmonary delivery, e.g., comprising nebulization. In these embodiments, the delivery vehicle may be in an aerosolized composition which can be inhaled. In some embodiments, the mRNA is expressed in the tissue in which the delivery vehicle was administered, e.g., nasal cavity, trachea, bronchi, bronchioles, and/or other pulmonary system-related cell or tissue. Additional teaching of pulmonary delivery and nebulization are described in the related international application PCT/US17/61100 filed Nov. 10, 2017 by Applicant entitled "NOVEL ICE-BASED LIPID NANOPARTICLE FORMULATION FOR DELIVERY OF MRNA", and the U. S. Provisional Application U.S. Ser. No. 62/507,061, each of which is incorporated by reference in its entirety.

In some embodiments, mRNAs encoding a CFTR protein may be delivered via a single delivery vehicle. In some embodiments, mRNAs encoding a CFTR protein may be delivered via one or more delivery vehicles each of a different composition. According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly(D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95).

A delivery vehicle comprising CFTR mRNA may be administered and dosed in accordance with current medical practice, taking into account the clinical condition of the subject, the site and method of administration (e.g., local and systemic, including oral, pulmonary, and via injection), the scheduling of administration, the subject's age, sex, body weight, and other factors relevant to clinicians of ordinary skill in the art. The "effective amount" for the purposes herein may be determined by such relevant considerations as are known to those of ordinary skill in experimental clinical research, pharmacological, clinical and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein production.

In some embodiments, a CFTR mRNA is administered in combination with one or more CFTR potentiators and/or correctors. Suitable CFTR potentiators and/or correctors include ivacaftor (trade name Kalydeco®), lumacaftor (trade name Orkambi®) or the combination of ivacaftor and lumacaftor. In some embodiments, a CFTR mRNA is administered in combination with one or more other CF treatment such as hormone replacement therapies, thyroid hormone replacement therapy, non-steroidal inflammatory drugs, and prescription dronabinol (Marinol®) during treatment.

In some embodiments, the human subject receives concomitant CFTR modulator therapy. In some embodiments, the concomitant CFTR modulator therapy comprises ivacaftor. In some embodiments, the concomitant CFTR modulator therapy comprises lumacaftor. In some embodiments, the concomitant CFTR modulator therapy comprises tezacaftor. In some embodiments, the concomitant CFTR modulator therapy is selected from ivacaftor, lumacaftor, tezacaftor, or a combination. In some embodiments, the concomitant CFTR modulator therapy comprises VX-659. In some embodiments, the concomitant CFTR modulator therapy comprises VX-445. In some embodiments, the concomitant CFTR modulator therapy comprises VX-152. In some embodiments, the concomitant CFTR modulator therapy comprises VX-440. In some embodiments, the concomitant CFTR modulator therapy comprises VX-371. In some embodiments, the concomitant CFTR modulator therapy comprises VX-561. In some embodiments, the concomitant CFTR modulator therapy comprises GLPG1837. In some embodiments, the concomitant CFTR modulator therapy comprises GLPG2222. In some embodiments, the concomitant CFTR modulator therapy comprises GLPG2737. In some embodiments, the concomitant CFTR modulator therapy comprises GLPG2451. In some embodiments, the concomitant CFTR modulator therapy comprises GLPG1837. In some embodiments, the concomitant CFTR modulator therapy comprises PTI-428. In some embodiments, the concomitant CFTR modulator therapy comprises PTI-801. In some embodiments, the concomitant CFTR modulator therapy comprises PTI-808. In some embodiments, the concomitant CFTR modulator therapy comprises eluforsen.

In some embodiments, the human subject is not eligible for treatment with one or more of ivacaftor, lumacaftor, tezacaftor, VX-659, VX-445, VX-152, VX-440, VX-371, VX-561, VX-659 or combinations thereof. In some embodiments, the human subject is not eligible for treatment with one or more of ivacaftor, lumacaftor, tezacaftor, VX-659, VX-445, VX-152, VX-440, VX-371, VX-561, VX-659, GLPG1837, GLPG2222, GLPG2737, GLPG2451, GLPG1837, PTI-428, PTI-801, PTI-808, eluforsen, or combinations thereof.

In some embodiments, delivery vehicles are formulated such that they are suitable for extended-release of the mRNA contained therein. Such extended-release compositions may be conveniently administered to a subject at extended dosing intervals.

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, a liposomal delivery vehicle typically serves to transport a desired mRNA to a target cell or tissue. In some embodiments, a nanoparticle delivery vehicle is a liposome. In some embodiments, a liposome comprises one or more cationic lipids, one or more non-cationic lipids, one or more cholesterol-based lipids and one or more PEG-modified lipids. In some embodiments, a liposome comprises no more than three distinct lipid components. In some embodiments, one distinct lipid component is a sterol-based cationic lipid.

Cationic Lipids

As used herein, the phrase "cationic lipids" refers to any of a number of lipid species that have a net positive charge at a selected pH, such as physiological pH.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein Li and L2 are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z,12Z)-octadeca-9,12-dien-1-yl) tetracosa-15,18-dien-1-amine ("HGT5000"), having a compound structure of:

(HGT-5000)

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001"), having a compound structure of:

(HGT-5001)

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

(HGT-5002)

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

and pharmaceutically acceptable salts thereof. In certain embodiments, the compositions and methods of the present invention include a cationic lipid having a compound structure of:

and pharmaceutically acceptable salts thereof. In certain embodiments, the compositions and methods of the present invention include a cationic lipid having a compound structure of:

and pharmaceutically acceptable salts thereof. In certain embodiments, the compositions and methods of the present invention include a cationic lipid having a compound structure of:

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each RB is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

(Target 23)

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound structure:

or a pharmaceutically acceptable salt thereof. In some embodiments, the compositions and methods of the present invention include a cationic lipid having the compound structure:

or a pharmaceutically acceptable salt thereof. In some embodiments, the compositions and methods of the present invention include a cationic lipid having the compound structure:

or a pharmaceutically acceptable salt thereof.

Other suitable cationic lipids for use in the compositions and methods of the present invention include cationic lipids as described in U.S. Provisional Patent Application Ser. No. 62/758,179, which is incorporated herein by reference. In some embodiments, the compositions and methods of the present invention include a cationic lipid of the following formula:

or a pharmaceutically acceptable salt thereof, wherein each $R^1$ and $R^2$ is independently H or $C_1$-$C_6$ aliphatic; each m is independently an integer having a value of 1 to 4; each A is independently a covalent bond or arylene; each $L^1$ is independently an ester, thioester, disulfide, or anhydride group; each $L^2$ is independently $C_2$-$C_{10}$ aliphatic; each $X^1$ is inde- pendently H or OH; and each $R^3$ is independently $C_6$-$C_{20}$ aliphatic. In some embodiments, the compositions and methods of the present invention include a cationic lipid of the following formula:

(Compound 1)

or a pharmaceutically acceptable salt thereof. In some embodiments, the compositions and methods of the present invention include a cationic lipid of the following formula:

(Compound 2)

or a pharmaceutically acceptable salt thereof. In some embodiments, the compositions and methods of the present invention include a cationic lipid of the following formula:

(Compound 3)

or a pharmaceutically acceptable salt thereof.

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

15 and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

and pharmaceutically acceptable salts thereof. In some embodiments, the compositions and methods of the present invention include a cationic lipid having the compound structure:

65 and pharmaceutically acceptable salts thereof. In some embodiments, the compositions and methods of the present invention include a cationic lipid having the compound structure:

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

or a pharmaceutically acceptable salt thereof, wherein one of $L^1$ or $L^2$ is —O(C=O)—, —(C=O)O—, —C(=O)—, —O—, —S(O)$_x$, —S—S—, —C(=O)S—, —SC(=O)—, —NR$^a$C(=O)—, —C(=O)NR$^a$—, NR$^a$C(=O)NR$^a$—, —OC(=O)NR$^a$—, or —NR$^a$C(=O)O—; and the other of $L^1$ or $L^2$ is —O(C=O)—, —(C=O)O—, —C(=O)—, —O—, —S(O) x, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, OR$^5$, CN, —C(=O)OR$^4$, —OC(=O)R$^4$ or —NR$^5$C(=O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

and pharmaceutically acceptable salts thereof. In some embodiments, the compositions and methods of the present invention include a cationic lipid having the compound structure:

40 and pharmaceutically acceptable salts thereof. In some embodiments, the compositions and methods of the present invention include a cationic lipid having the compound structure:

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

and pharmaceutically acceptable salts thereof. For any one of these four formulas, $R_4$ is independently selected from —$(CH_2)_nQ$ and —$(CH_2)_nCHQR$; Q is selected from the group consisting of —OR, —OH, —$O(CH_2)_nN(R)_2$, —OC(O)R, —$CX_3$, —CN, —N(R)C(O)R, —N(H)C(O)R, —$N(R)S(O)_2R$, —$N(H)S(O)_2R$, —$N(R)C(O)N(R)_2$, —$N(H)C(O)N(R)_2$, —N(H)C(O)N(H)(R), —N(R)C(S)N(R)_2$, —$N(H)C(S)N(R)_2$, —N(H)C(S)N(H)(R), and a heterocycle; and n is 1, 2, or 3. In certain embodiments, the compositions and methods of the present invention include a cationic lipid having a compound structure of:

and pharmaceutically acceptable salts thereof. In certain embodiments, the compositions and methods of the present invention include a cationic lipid having a compound structure of:

and pharmaceutically acceptable salts thereof. In certain embodiments, the compositions and methods of the present invention include a cationic lipid having a compound structure of:

and pharmaceutically acceptable salts thereof. In certain embodiments, the compositions and methods of the present invention include a cationic lipid having a compound structure of:

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

and pharmaceutically acceptable salts thereof. In certain embodiments, the compositions and methods of the present invention include a cationic lipid having a compound structure of:

and pharmaceutically acceptable salts thereof. In certain embodiments, the compositions and methods of the present invention include a cationic lipid having a compound structure of:

and pharmaceutically acceptable salts thereof. In certain embodiments, the compositions and methods of the present invention include a cationic lipid having a compound structure of:

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

(HGT4001)

and pharmaceutically acceptable salts thereof. In certain embodiments, the compositions and methods of the present invention include a cationic lipid, "HGT4002" (also referred to herein as "Guan-SS-Chol"), having a compound structure of:

(HGT4002)

and pharmaceutically acceptable salts thereof. In certain embodiments, the compositions and methods of the present invention include a cationic lipid, "HGT4003", having a compound structure of:

(HGT4003)

and pharmaceutically acceptable salts thereof. In certain embodiments, the compositions and methods of the present invention include a cationic lipid, "HGT4004", having a compound structure of:

(HGT4004)

and pharmaceutically acceptable salts thereof. In certain embodiments, the compositions and methods of the present invention include a cationic lipid "HGT4005", having a compound structure of:

(HGT4005)

and pharmaceutically acceptable salts thereof.

Other suitable cationic lipids for use in the compositions and methods of the present invention include cleavable cationic lipids as described in U.S. Provisional Application No. 62/672,194, filed May 16, 2018, and incorporated herein by reference. In certain embodiments, the compositions and methods of the present invention include a cationic lipid that is any of general formulas or any of structures (1a)-(21a) and (1b)-(21b) and (22)-(237) described in U.S. Provisional Application No. 62/672,194. In certain embodiments, the compositions and methods of the present invention include a cationic lipid that has a structure according to Formula (I'), $$B\text{—}L^{4B}\text{—}L^{4A}\text{—}O$$ (I')

wherein:

$R^x$ is independently —H, -$L^1$-$R^1$, or -$L^{5A}$-$L^{5B}$-B';

each of $L^1$, $L^2$, and $L^3$ is independently a covalent bond, —C(O)—, —C(O)O—, —C(O)S—, or —C(O)NR$^L$—;

each $L^{4A}$ and $L^{5A}$ is independently —C(O)—, —C(O)O—, or —C(O)NR$^L$—;

each $L^{4B}$ and $L^{5B}$ is independently $C_1$-$C_{20}$ alkylene; $C_2$-$C_{20}$ alkenylene; or $C_2$-$C_{20}$ alkynylene;

each B and B' is NR$^4$R$^5$ or a 5- to 10-membered nitrogen-containing heteroaryl;

each $R^1$, $R^2$, and $R^3$ is independently $C_6$-$C_{30}$ alkyl, $C_6$-$C_{30}$ alkenyl, or $C_6$-$C_{30}$ alkynyl;

each $R^4$ and $R^5$ is independently hydrogen, $C_1$-$C_{10}$ alkyl; $C_2$-$C_{10}$ alkenyl; or $C_2$-$C_{10}$ alkynyl; and each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of 62/672,194, having a compound structure of:

herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy) dimethyl-1-(cis,cis-9',1-2'-octadecadienoxy)propane ("CpLinDMA"); N,N-dimethyl-3,4-dioleyloxybenzylamine ("DMOBA"); 1,2-N,N'-dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoyl-carbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy] octyl)oxy)-N, N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy] octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-oc-

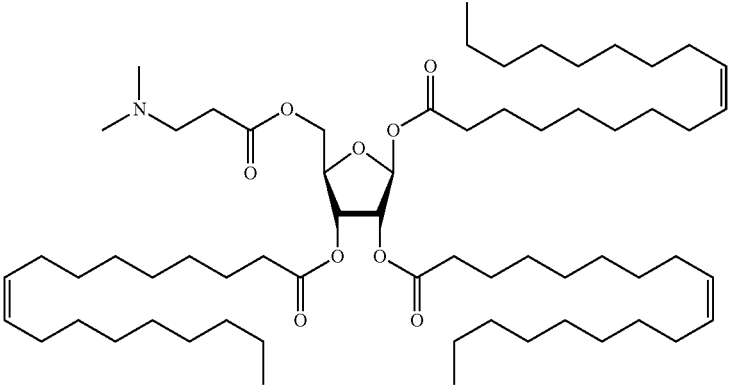

("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated tadeca-9,12-dien-1-yl)-1,3-dioxolan-4-yl)-N,N-dimethyl-ethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety. In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)—N,N-dimethyl-2,2-di((9Z, 12Z)-octadeca-9,12-dienyl)tetrahydro-3aH-cyclopenta[d][1,3]dioxol-5-amine ("ALNY-100") and/or 4,7,13-tris(3-oxo-3-(undecylamino)propyl)-N1,N16-diundecyl-4,7,10,13-tetraazahexadecane-1,16-diamide ("NC98-5").

In some embodiments, one or more cationic lipids suitable for the compositions and methods of the present invention include a cationic lipid that is TL1-04D-DMA, having a compound structure of:

("TL1-04D-DMA")

In some embodiments, one or more cationic lipids suitable for the compositions and methods of the present invention include a cationic lipid that is GL-TES-SA-DME-E18-2, having a compound structure of:

(GL-TES-SA-DME-E18-2")

In some embodiments, one or more cationic lipids suitable for the compositions and methods of the present invention include a cationic lipid that is SY-3-E14-DMAPr, having a compound structure of:

("SY-3-E14-DMAPr")

In some embodiments, one or more cationic lipids suitable for the compositions and methods of the present invention include a cationic lipid that is TL1-01D-DMA, having a compound structure of:

("TL1-01D-DMA")

In some embodiments, one or more cationic lipids suitable for the compositions and methods of the present invention include a cationic lipid that is TL1-10D-DMA, having a compound structure of:

("TL1-10D-DMA")

In some embodiments, one or more cationic lipids suitable for the compositions and methods of the present invention include a cationic lipid that is GL-TES-SA-DMP-E18-2, having a compound structure of:

("GL-TES-SA-DMP-E18-2")

In some embodiments, one or more cationic lipids suitable for the compositions and methods of the present invention include a cationic lipid that is HEP-E4-E10, having a compound structure of:

("HEP-E4-E10")

In some embodiments, one or more cationic lipids suitable for the compositions and methods of the present invention include a cationic lipid that is HEP-E3-E10, having a compound structure of:

("HEP-E3-E10")

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle.

Non-Cationic/Helper Lipids

In some embodiments, provided liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected H, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), phosphatidylserine, sphingolipids, cerebrosides, gangliosides, 16-O-monomethyl PE, 16-O-dimethyl PE, 18-1-trans PE, 1-stearoyl-2-oleoyl-phosphatidyethanolamine (SOPE), or a mixture thereof.

In some embodiments, such non-cationic lipids may be used alone, but are preferably used in combination with other lipids, for example, cationic lipids. In some embodiments, the non-cationic lipid may comprise a molar ratio of about 5% to about 90%, or about 10% to about 70% of the total lipid present in a liposome. In some embodiments, a non-cationic lipid is a neutral lipid, i.e., a lipid that does not carry a net charge in the conditions under which the composition is formulated and/or administered. In some embodiments, the percentage of non-cationic lipid in a liposome may be greater than 5%, greater than 10%, greater than 20%, greater than 30%, or greater than 40%.

Cholesterol-Based Lipids

In some embodiments, provided liposomes comprise one or more cholesterol-based lipids. For example, suitable cholesterol-based cationic lipids include, for example, DC-Choi (N,N-dimethyl-N-ethylcarboxamidocholesterol),1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or ICE. In some embodiments, the cholesterol-based lipid may comprise a molar ration of about 2% to about 30%, or about 5% to about 20% of the total lipid present in a liposome. In some embodiments, the percentage of cholesterol-based lipid in the lipid nanoparticle may be greater than 5%, greater than 10%, greater than 20%, greater than 30%, or greater than 40%.

PEG-Modified Lipids

The use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle). Contemplated PEG-modified lipids include, but are not limited to, a polyethylene glycol chain of up to S kDa in length covalently attached to a lipid with alkyl chain(s) of $C_6$-$C_{20}$ length. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., C14 or C18). The PEG-modified phospholipid and derivatized lipids of the present invention may comprise a molar ratio from about 0% to about 20%, about 0.5% to about 20%, about 1% to about 15%, about 4% to about 10%, or about 2% of the total lipid present in the liposomal transfer vehicle.

According to various embodiments, the selection of cationic lipids, non-cationic lipids and/or PEG-modified lipids which comprise the lipid nanoparticle, as well as the relative molar ratio of such lipids to each other, is based upon the characteristics of the selected lipid(s), the nature of the intended target cells, the characteristics of the MCNA to be delivered. Additional considerations include, for example, the saturation of the alkyl chain, as well as the size, charge, pH, pKa, fusogenicity and toxicity of the selected lipid(s). Thus the molar ratios may be adjusted accordingly.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

Liposomes Suitable for Use with the Present Invention

A suitable liposome for the present invention may include one or more of any of the cationic lipids, non-cationic lipids, cholesterol lipids, PEG-modified lipids and/or polymers described herein at various ratios. As non-limiting examples, a suitable liposome formulation may include a combination selected from cKK-E12, DOPE, cholesterol and DMG-PEG2K; $C_{12}$-200, DOPE, cholesterol and DMG-PEG2K; HGT4003, DOPE, cholesterol and DMG-PEG2K; ICE, DOPE, cholesterol and DMG-PEG2K; or ICE, DOPE, and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, $C_{12}$-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:

1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s) to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5.

In particular embodiments, a liposome for use with this invention comprises a lipid component consisting of a cationic lipid, a non-cationic lipid (e.g., DOPE or DEPE), a PEG-modified lipid (e.g., DMG-PEG2K), and optionally cholesterol. Cationic lipids particularly suitable for inclusion in such a liposome include GL-TES-SA-DME-E18-2, TL1-01D-DMA, SY-3-E14-DMAPr, TL1-10D-DMA, HGT4002 (also referred to herein as Guan-SS-Chol), GL-TES-SA-DMP-E18-2, HEP-E4-E10, HEP-E3-E10, and TL1-04D-DMA.

These cationic lipids have been found to be particularly suitable for use in liposomes that are administered through pulmonary delivery via nebulization. Amongst these, HEP-E4-E10, HEP-E3-E10, GL-TES-SA-DME-E18-2, GL-TES-SA-DMP-E18-2, TL1-01D-DMA and TL1-04D-DMA performed particularly well.

Exemplary liposomes include one of GL-TES-SA-DME-E18-2, TL1-01D-DMA, SY-3-E14-DMAPr, TL1-10D-DMA, GL-TES-SA-DMP-E18-2, HEP-E4-E10, HEP-E3-E10 and TL1-04D-DMA as a cationic lipid component, DOPE as a non-cationic lipid component, cholesterol as a helper lipid component, and DMG-PEG2K as a PEG-modified lipid component. In some embodiments, the molar ratio of the cationic lipid to non-cationic lipid to cholesterol to PEG-modified lipid may be between about 30-60:25-35:20-30:1-15, respectively. In some embodiments, the molar ratio of cationic lipid to non-cationic lipid to cholesterol to PEG-modified lipid is approximately 40:30:20:10, respectively. In some embodiments, the molar ratio of cationic lipid to non-cationic lipid to cholesterol to PEG-modified lipid is approximately 40:30:25:5, respectively. In some embodiments, the molar ratio of cationic lipid to non-cationic lipid to cholesterol to PEG-modified lipid is approximately 40:32:25:3, respectively. In some embodiments, the molar ratio of cationic lipid to non-cationic lipid to cholesterol to PEG-modified lipid is approximately 50:25:20:5.

In some embodiments, the lipid component of a liposome particularly suitable for pulmonary delivery consists of HGT4002 (also referred to herein as Guan-SS-Chol), DOPE and DMG-PEG2K. In some embodiments, the molar ratio of cationic lipid to non-cationic lipid to PEG-modified lipid is approximately 60:35:5.

Ratio of Distinct Lipid Components

In embodiments where a lipid nanoparticle comprises three and no more than three distinct components of lipids, the ratio of total lipid content (i.e., the ratio of lipid component (1):lipid component (2):lipid component (3)) can be represented as x:y:z, wherein $$(y+z)=100-x.$$

In some embodiments, each of "x," "y," and "z" represents molar percentages of the three distinct components of lipids, and the ratio is a molar ratio.

In some embodiments, each of "x," "y," and "z" represents weight percentages of the three distinct components of lipids, and the ratio is a weight ratio.

In some embodiments, lipid component (1), represented by variable "x," is a sterol-based cationic lipid.

In some embodiments, lipid component (2), represented by variable "y," is a helper lipid.

In some embodiments, lipid component (3), represented by variable "z" is a

PEG lipid.

In some embodiments, variable "x," representing the molar percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the molar percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the molar percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%; at least about 50% but less than about 65%; or at least about 50% but less than about 60%.

In some embodiments, variable "x," representing the weight percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the weight percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the weight percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%; at least about 50% but less than about 65%; or at least about 50% but less than about 60%.

In some embodiments, variable "z," representing the molar percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z,"

representing the molar percentage of lipid component (3) (e.g., a PEG lipid) is about 1%, 2%, 3%, 4%, 5%, 6%, 7%, 8%, 9%, 10%. In embodiments, variable "z," representing the molar percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

In some embodiments, variable "z," representing the weight percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the weight percentage of lipid component (3) (e.g., a PEG lipid) is about 1%, 2%, 3%, 4%, 5%, 6%, 7%, 8%, 9%, 10%. In embodiments, variable "z," representing the weight percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

For compositions having three and only three distinct lipid components, variables "x," "y," and "z" may be in any combination so long as the total of the three variables sums to 100% of the total lipid content.

Formation of Liposomes Encapsulating mRNA

The liposomal transfer vehicles for use in the compositions of the invention can be prepared by various techniques which are presently known in the art. The liposomes for use in provided compositions can be prepared by various techniques which are presently known in the art. For example, multilamellar vesicles (MLV) may be prepared according to conventional techniques, such as by depositing a selected lipid on the inside wall of a suitable container or vessel by dissolving the lipid in an appropriate solvent, and then evaporating the solvent to leave a thin film on the inside of the vessel or by spray drying. An aqueous phase may then be added to the vessel with a vortexing motion which results in the formation of MLVs. Unilamellar vesicles (ULV) can then be formed by homogenization, sonication or extrusion of the multilamellar vesicles. In addition, unilamellar vesicles can be formed by detergent removal techniques.

In certain embodiments, provided compositions comprise a liposome wherein the mRNA is associated on both the surface of the liposome and encapsulated within the same liposome. For example, during preparation of the compositions of the present invention, cationic liposomes may associate with the mRNA through electrostatic interactions. For example, during preparation of the compositions of the present invention, cationic liposomes may associate with the mRNA through electrostatic interactions.

In some embodiments, the compositions and methods of the invention comprise mRNA encapsulated in a liposome. In some embodiments, the one or more mRNA species may be encapsulated in the same liposome. In some embodiments, the one or more mRNA species may be encapsulated in different liposomes. In some embodiments, the mRNA is encapsulated in one or more liposomes, which differ in their lipid composition, molar ratio of lipid components, size, charge (zeta potential), targeting ligands and/or combinations thereof. In some embodiments, the one or more liposome may have a different composition of sterol-based cationic lipids, neutral lipid, PEG-modified lipid and/or combinations thereof. In some embodiments the one or more liposomes may have a different molar ratio of cholesterol-based cationic lipid, neutral lipid, and PEG-modified lipid used to create the liposome.

The process of incorporation of a desired mRNA into a liposome is often referred to as "loading". Exemplary methods are described in Lasic, et al., FEBS Lett., 312: 255-258, 1992, which is incorporated herein by reference. The liposome-incorporated nucleic acids may be completely or partially located in the interior space of the liposome, within the bilayer membrane of the liposome, or associated with the exterior surface of the liposome membrane. The incorporation of a nucleic acid into liposomes is also referred to herein as "encapsulation" wherein the nucleic acid is entirely contained within the interior space of the liposome. The purpose of incorporating an mRNA into a transfer vehicle, such as a liposome, is often to protect the nucleic acid from an environment which may contain enzymes or chemicals that degrade nucleic acids and/or systems or receptors that cause the rapid excretion of the nucleic acids. Accordingly, in some embodiments, a suitable delivery vehicle is capable of enhancing the stability of the mRNA contained therein and/or facilitate the delivery of mRNA to the target cell or tissue.

Suitable liposomes in accordance with the present invention may be made in various sizes. In some embodiments, provided liposomes may be made smaller than previously known mRNA encapsulating liposomes. In some embodiments, decreased size of liposomes is associated with more efficient delivery of mRNA. Selection of an appropriate liposome size may take into consideration the site of the target cell or tissue and to some extent the application for which the liposome is being made.

In some embodiments, an appropriate size of liposome is selected to facilitate systemic distribution of antibody encoded by the mRNA. In some embodiments, it may be desirable to limit transfection of the mRNA to certain cells or tissues. For example, to target hepatocytes a liposome may be sized such that its dimensions are smaller than the fenestrations of the endothelial layer lining hepatic sinusoids in the liver; in such cases the liposome could readily penetrate such endothelial fenestrations to reach the target hepatocytes.

Alternatively or additionally, a liposome may be sized such that the dimensions of the liposome are of a sufficient diameter to limit or expressly avoid distribution into certain cells or tissues.

A variety of alternative methods known in the art are available for sizing of a population of liposomes. One such sizing method is described in U.S. Pat. No. 4,737,323, incorporated herein by reference. Sonicating a liposome suspension either by bath or probe sonication produces a progressive size reduction down to small ULV less than about 0.05 microns in diameter. Homogenization is another method that relies on shearing energy to fragment large liposomes into smaller ones. In a typical homogenization procedure, MLV are recirculated through a standard emulsion homogenizer until selected liposome sizes, typically between about 0.1 and 0.5 microns, are observed. The size of the liposomes may be determined by quasi-electric light scattering (QELS) as described in Bloomfield, Ann. Rev. Biophys. Bioeng., 10:421-150 (1981), incorporated herein by reference. Average liposome diameter may be reduced by sonication of formed liposomes. Intermittent sonication cycles may be alternated with QELS assessment to guide efficient liposome synthesis.

Therapeutic Use of Compositions

In one aspect, the present invention, among other things, provide a method of inducing CFTR expression in vivo by administration of codon optimized nucleic acids encoding a wild-type CFTR protein, or by administration of a CFTR protein. In some embodiments, a composition comprises nucleic acids encapsulated or complexed with a delivery vehicle. In some embodiments, the delivery vehicle is selected from the group consisting of liposomes, lipid nanoparticles, solid-lipid nanoparticles, polymers, viruses, sol-gels, and nanogels. In some embodiments, codon optimized nucleic acids encoding a wild-type CFTR protein are packaged in a viral particle.

Gene Therapy

In some embodiments, a pharmaceutical composition comprising codon optimized nucleic acids encoding a wild-type CFTR protein is used to treat subjects in need thereof. In some embodiments, a pharmaceutical composition comprising a rAAV vector described herein is used to treat subjects in need thereof. The pharmaceutical composition containing a rAAV vector or particle of the invention contains a pharmaceutically acceptable excipient, diluent or carrier. Examples of suitable pharmaceutical carriers are well known in the art and include phosphate buffered saline solutions, water, emulsions, such as oil/water emulsions, various types of wetting agents, sterile solutions and the like. The pharmaceutical composition can be in a lyophilized form. Such carriers can be formulated by conventional methods and are administered to the subject at a therapeutically effective amount.

The rAAV vector is administered to a subject in need thereof via a suitable route. In some embodiments, the rAAV vector is administered by intravenous, intraperitoneal, subcutaneous, or intradermal routes. In one embodiment, the rAAV vector is administered intravenously. In embodiments, the intradermal administration comprises administration by use of a "gene gun" or biolistic particle delivery system. In some embodiments, the rAAV vector is administered via a non-viral lipid nanoparticle. For example, a composition comprising the rAAV vector may comprise one or more diluents, buffers, liposomes, a lipid, a lipid complex. In some embodiments, the rAAV vector is comprised within a microsphere or a nanoparticle, such as a lipid nanoparticle or an inorganic nanoparticle.

In some embodiments, a rAAV is pseudotyped. A pseudotyped rAAV is an infectious virus comprising any combination of an AAV capsid protein and a rAAV genome. Pseudotyped rAAV are useful to alter the tissue or cell specificity of rAAV, and may be employed alone or in conjunction with non-pseudotyped rAAV to transfer one or more genes to a cell, e.g., a mammalian cell. For example, pseudotyped rAAV may be employed subsequent to administration with non-pseudotyped rAAV in a mammal which has developed an immune response to the non-pseudotyped rAAV. Capsid proteins from any AAV serotype may be employed with a rAAV genome which is derived or obtainable from a wild-type AAV genome of a different serotype or which is a chimeric genome, i.e., formed from AAV DNA from two or more different serotypes, e.g., a chimeric genome having 2 ITRs, each ITR from a different serotype or chimeric ITRs. The use of chimeric genomes such as those comprising ITRs from two AAV serotypes or chimeric ITRs can result in directional recombination which may further enhance the production of transcriptionally active intermolecular concatamers. Thus, the 5' and 3' ITRs within a rAAV vector of the invention may be homologous, i.e., from the same serotype, heterologous, i.e., from different serotypes, or chimeric, i.e., an ITR which has ITR sequences from more than one AAV serotype.

In some embodiments, the rAAV vector is an AAV1, AAV2, AAV3, AAV4, AAV5, AAV6, AAV7, AAV8, AAV9, AAV10, or AAV11 vector. In some embodiments, the rAAV vector is AAV1. In some embodiments, the rAAV vector is AAV2. In some embodiments, the rAAV vector is AAV3. In some embodiments, the rAAV vector is AAV4. In some embodiments, the rAAV vector is AAV5. In some embodiments, the rAAV vector is AAV6. In some embodiments, the rAAV vector is AAV7. In some embodiments, the rAAV vector is AAV8. In some embodiments, the rAAV vector is AAV9. In some embodiments, the rAAV vector is AAV10. In some embodiments, the rAAV vector is AAV11. In some embodiments, the rAAV vector is sequence optimized. In some embodiments, the rAAV capsid is modified. For example, in some embodiments, the rAAV8 capsid is modified.

For oral administrations, the pharmaceutical preparations are in the form of, for example, tablets or capsules prepared by known methods with pharmaceutically acceptable excipients such as binders (for example pregelatinized maize starch, polyvinylpyrrolidone, or methyl cellulose); fillers (for example lactose, microcrystalline cellulose or calcium hydrogen phosphate); additives (for example magnesium stearate, talc, silica); disintegrants (for example potato starch); and/or lubricants (for example sodium lauryl sulphate). The tablets can be coated using known methods. Liquid preparations for oral administration have the form, for example, of solutions, syrups or suspensions, or can be in the form of a dry product that can be dissolved in water or another liquid prior to use. Said preparations are prepared by known methods with pharmaceutically acceptable additives such as suspending agents (for example sorbitol, cellulose derivatives, edible hydrogenated fats); emulsifying agents (for example lecithin or acacia); non-aqueous liquids (for example almond oil, oily esters, ethyl alcohol or fractionated vegetable oils); and/or preservatives (for example methyl or propylhydroxybenzoates, sorbic acid or ascorbic acid). The preparations can also contain, in appropriate cases, buffering salts, colouring agents, flavouring agents and/or sweeteners.

Preparations for oral administration are formulated in a known manner, in order to provide a controlled release of the active compound.

EXAMPLES

While certain compounds, compositions and methods of the present invention have been described with specificity in accordance with certain embodiments, the following examples serve only to illustrate the compounds of the invention and are not intended to limit the same.

Example 1. Generating Optimized Nucleotide Sequences

This example illustrates a process that results in optimized nucleotide sequences in accordance with the invention that are optimized to yield full-length transcripts during in vitro synthesis and result in high levels of expression of the encoded protein.

Figure 1B:
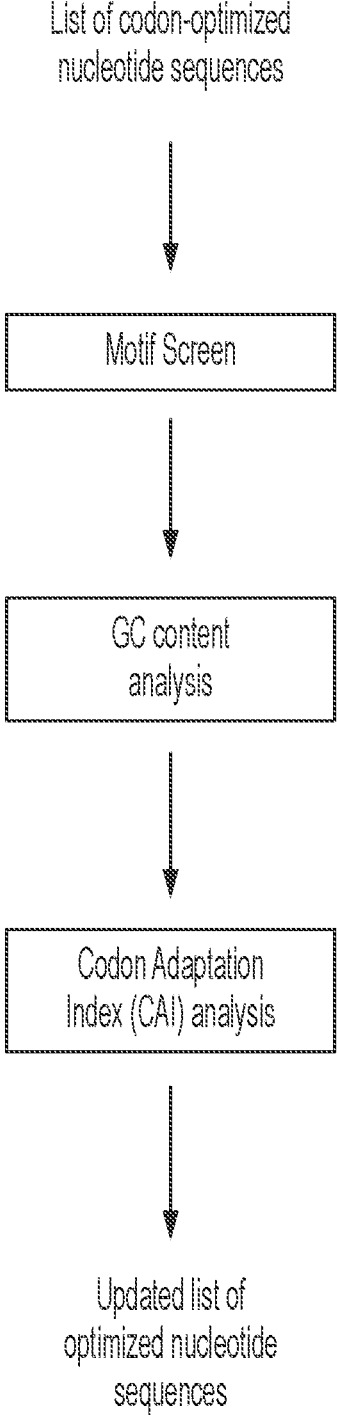

The process combines the codon optimization method of FIG. 1A with a sequence of filtering steps illustrated in FIG. 1B to generate a list of optimized nucleotide sequences. Specifically, as illustrated FIG. 1A, the process receives an amino acid sequence of interest and a first codon usage table which reflects the frequency of each codon in a given organism (namely human codon usage preferences in the context of the present example). The process then removes codons from the first codon usage table if they are associated with a codon usage frequency which is less than a threshold frequency (10%). The codon usage frequencies of the codons not removed in the first step are normalized to generate a normalized codon usage table.

Normalizing the codon usage table involves re-distributing the usage frequency value for each removed codon; the usage frequency for a certain removed codon is added to the usage frequencies of the other codons with which the removed codon shares an amino acid. In this example, the re-distribution is proportional to the magnitude of the usage frequencies of the codons not removed from the table. The process uses the normalized codon usage table to generate a list of optimized nucleotide sequences. Each of the optimized nucleotide sequences encode the amino acid sequence of interest.

As illustrated in FIG. 1B, the list of optimized nucleotide sequences is further processed by applying a motif screen filter, guanine-cytosine (GC) content analysis filter, and codon adaptation index (CAI) analysis filter, in that order, to generate an updated list of optimized nucleotide sequences.

As illustrated in following examples, this process results in optimized nucleotide sequences encoding the amino acid sequence of interest. The nucleotide sequences yield full-length transcripts during in vitro synthesis and result in high levels of expression of the encoded protein.

Example 2. Codon Optimization of the CFTR mRNA Sequence to Increase CAI Leads to Higher Protein Expression This example demonstrates that codon-optimized protein coding sequences with a codon adaptation index (CAI) of about 0.8 or higher outperform codon-optimized protein coding sequences with a CAI below 0.8.

Codon optimization was performed on the human cystic fibrosis transmembrane conductance regulator (hCFTR) as explain in Example 1. hCFTR is encoded by a sequence of 4440 nucleotides.

Mutations in the gene encoding the hCFTR protein cause cystic fibrosis (CF), the most common genetic disease in the Caucasian population. It is characterized by abnormal transport of chloride and sodium ions across the epithelium, leading to thick, viscous secretions that affect most critically the lungs, and also the pancreas, liver, and intestine. mRNA encoding a codon-optimized hCFTR coding sequence is being developed as a novel therapeutic to treat CF.

Codon optimization was performed on the native hCFTR amino acid sequence according to a method of the present invention as illustrated in Example 1. Three sequences designated hCFTR #1 (SEQ ID NO: 16), hCFTR #2 (SEQ ID NO: 2) and hCFTR #3 (SEQ ID NO: 3) were selected for further analysis. As a reference, a nucleotide sequence with a hCFTR coding sequence codon-optimized with a different algorithm was provided (SEQ ID NO: 15). This reference nucleotide sequence (SEQ ID NO: 15) had previously been validated experimentally both in vitro and in vivo. The reference nucleotide sequence had been found to provide superior protein yield relative to other earlier tested codon-optimized nucleotide sequences encoding the hCFTR protein. When compared to the reference nucleotide sequence, the CAI and GC content % of the codon-optimized hCFTR #2 and hCFTR #3 sequences were significantly increased. Furthermore, their codon frequency distribution (CFD) % was 0%, compared to 6% for the reference nucleotide sequence, indicating that rare codon clusters detrimental for translation efficiency were successfully removed. Additional filtering to remove negative regulatory motifs resulted in a significant reduction in the number of negative cis-regulatory (CIS) elements in hCFTR #2 and hCFTR #3 (cf. Table 2).

TABLE 2

| Nucleotide Sequence | SEQ ID NO: | CAI | GC content % | CFD % | Negative CIS elements | Negative repeat elements |
|---|---|---|---|---|---|---|
| hCFTR Reference | 15 | 0.70 | 49.52 | 6% | 7 | 0 |
| hCFTR #1 | 16 | 0.70 | 49.59 | 6% | 7 | 0 |
| hCFTR #2 | 2 | 0.89 | 53.78 | 0% | 4 | 0 |
| hCFTR #3 | 3 | 0.89 | 53.97 | 0% | 3 | 0 |

In order to test the protein yield from each of the codon-optimized sequences, 4 nucleic acid vectors were prepared each comprising an expression cassette that contained one of the 4 nucleotide sequences encoding the hCFTR protein flanked by identical 3' and 5' untranslated sequences (3' and 5' UTRs) and preceded by an RNA polymerase promoter. These nucleic acid vectors served as templates for in vitro transcription reactions to provide 4 batches of mRNA containing the 4 codon-optimized nucleotide sequences (reference and hCFTR #1 through #3). Capping and tailing was performed separately.

Figure 2A:
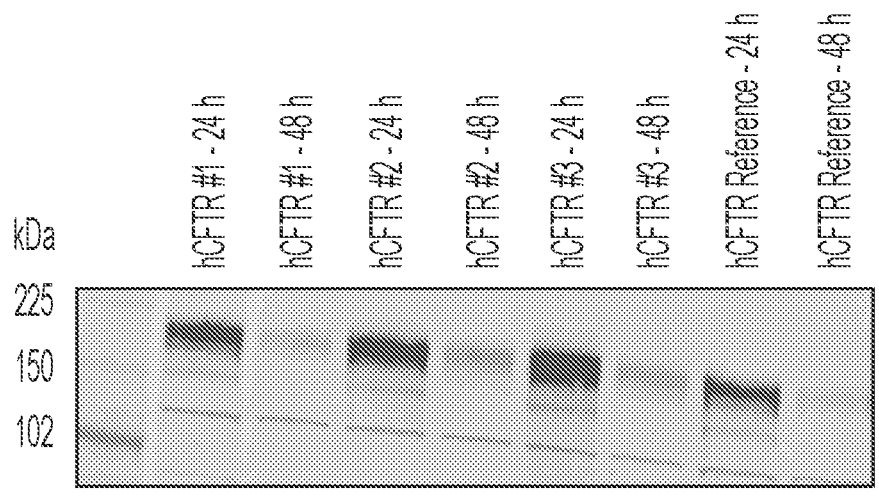
FIG. 2A illustrates an example western blot used to determine the protein expression yield of the CFTR protein encoded by optimized nucleotide sequences generated according to a method of the invention in a time course experiment, after the optimized nucleotide sequences were transfected into human cells.
Figure 2B:
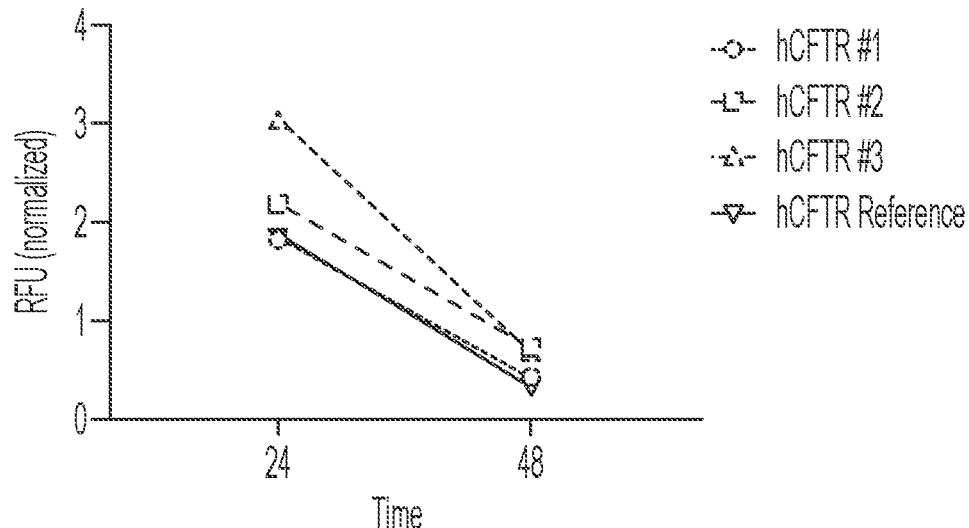
FIG. 2B illustrates an example line plot depicting the quantification of the western blot data depicted in FIG. 2A.

Each of the capped and tailed mRNAs were separately transfected into a cell line (HEK293). Cell lysates were collected 24 and 48 hours after transfection. Protein samples were extracted and processed for SDS-PAGE. Expression levels of the encoded hCFTR protein were assessed by Western Blot. Protein bands were developed and quantified using a LI-COR system. The protein yields were expressed as relative fluorescence units (RFU). The results of this experiment are summarized in FIG. 2A. Codon optimized nucleotide sequences hCFTR #2 and hCFTR #3, which both had a CAI of 0.89, produced significantly higher yields of the encoded hCFTR protein compared to the reference nucleotide sequence and hCFTR #1, which both had a CAI of 0.7. This effect was more pronounced at the 24 hour time point (see FIG. 2B), presumably due to the relatively rapid degradation of the mRNA in HEK293cells post transfection.

The data in this example demonstrate that codon optimization of a therapeutically relevant nucleotide sequence (hCFTR) to achieve a CAI of about 0.8 or higher results in greater protein yield, in particular when also combined with optimization of its CFD and its GC content and with the removal of any negative CIS elements from the nucleic acid sequence. The data in this example also confirm that codon optimization of the hCFTR mRNA according to the methods of the present invention results in very high hCFTR protein yield in human cells in comparison to nucleotide sequences codon-optimized with a different algorithm.

Example 3. Codon Optimization of the CFTR Nucleotide Sequence Leads to Increased Functional Activity in Cell This example illustrates that codon optimization of the hCFTR nucleotide sequence according to a method of the present invention does not impact hCFTR functional activity in human cells.

The administration of hCFTR mRNA is intended to result in its uptake by airway epithelial cells in CF patients, followed by internalization into the cytoplasm of the target cells. Once cellular uptake is achieved, hCFTR mRNA is translated into normal hCFTR protein, which is then processed through the cell's endogenous secretory pathway resulting in the localization of the hCFTR protein in the apical cell membrane. Through this approach, hCFTR mRNA administration produces functional hCFTR protein in the airway epithelium, thereby correcting the deficiency in functional CFTR in the lungs of the CF patients. Codon optimization of the hCFTR mRNA nucleotide sequence can increase expression of the functional hCFTR protein, which is thought to lead to a higher amount of functional hCFTR protein in the target airway epithelial cells of CF patients.

It has been reported that codon optimization can come at the cost of reduced functional activity of the encoded protein and an associated loss in efficacy as the process may remove information encoded in the nucleotide sequence that is important for controlling translation of the protein and ensuring proper folding of the nascent polypeptide chain (Mauro & Chappell, Trends Mol Med. 2014; 20(11):604-13). To test the functional activity of hCFTR protein expressed from the codon-optimized sequences generated using the codon optimization method as illustrated in Example 1, hCFTR mRNAs produced in Example 2 were tested in an Ussing chamber assay. This assay uses an epithelial voltage clamp to assess the functional activity of protein expressed from the hCFTR mRNA by monitoring the chloride transport function of epithelial cells that were transfected with said mRNA. Specifically, the functional activity of the hCFTR protein expressed from mRNAs with a control hCFTR coding sequence (SEQ ID NO: 15) or the coding sequence of hCFTR #1 (SEQ ID NO: 16), hCFTR #2 (SEQ ID NO: 2) or hCFTR #3 (SEQ ID NO: 3) was measured in Fischer rat thyroid (FRT) epithelial cells. FRT epithelial cells are commonly used as a model to study human airway epithelial cell function. FRT epithelial cells were grown in monolayers on Snapwell™ filter inserts and transfected with the 4 hCFTR mRNAs. The 4 hCFTR mRNAs were produced as described in Example 2. The control mRNA had previously been validated in this assay and was used as a reference standard.

Figure 3A:
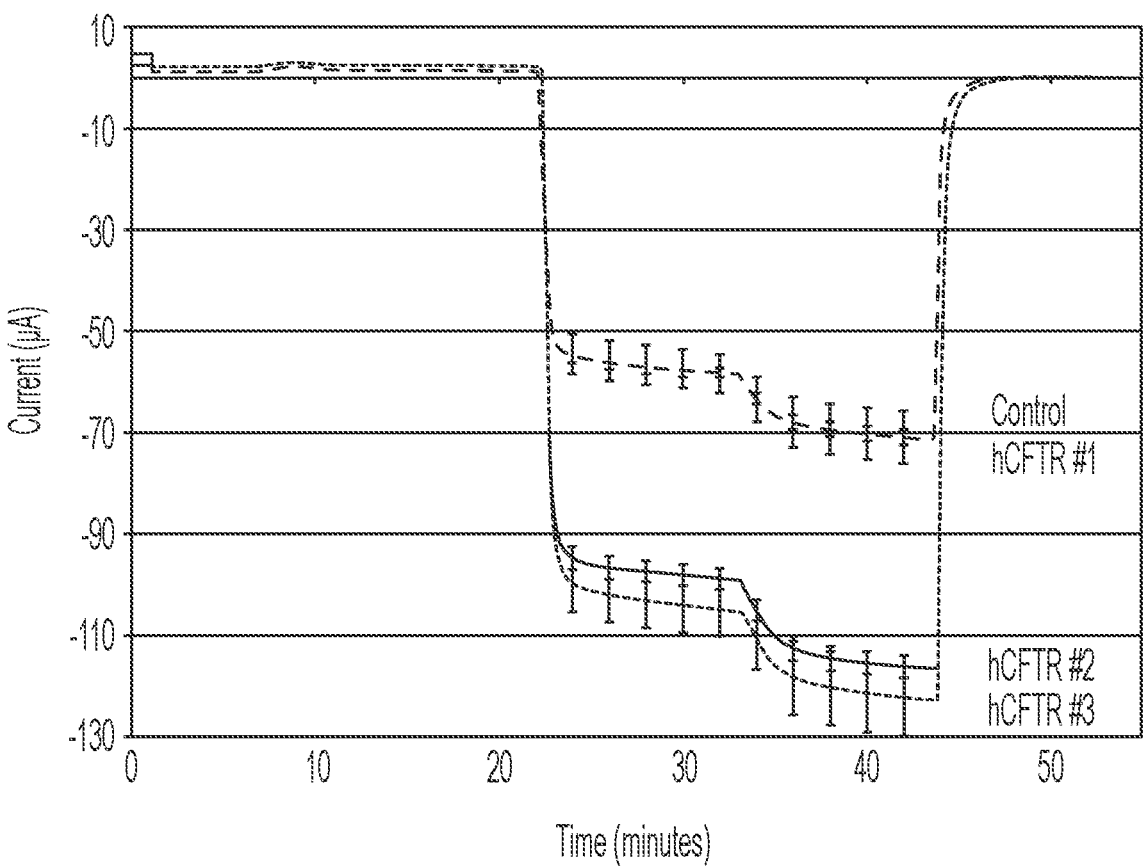
FIG. 3A illustrates an example plot of data obtained from a bioassay for testing mRNAs comprising an optimized nucleotide sequence encoding hCFTR. It depicts the short circuit current ($I_{SC}$) output within an Ussing epithelial voltage clamp apparatus for each tested mRNA.
Figure 3B:
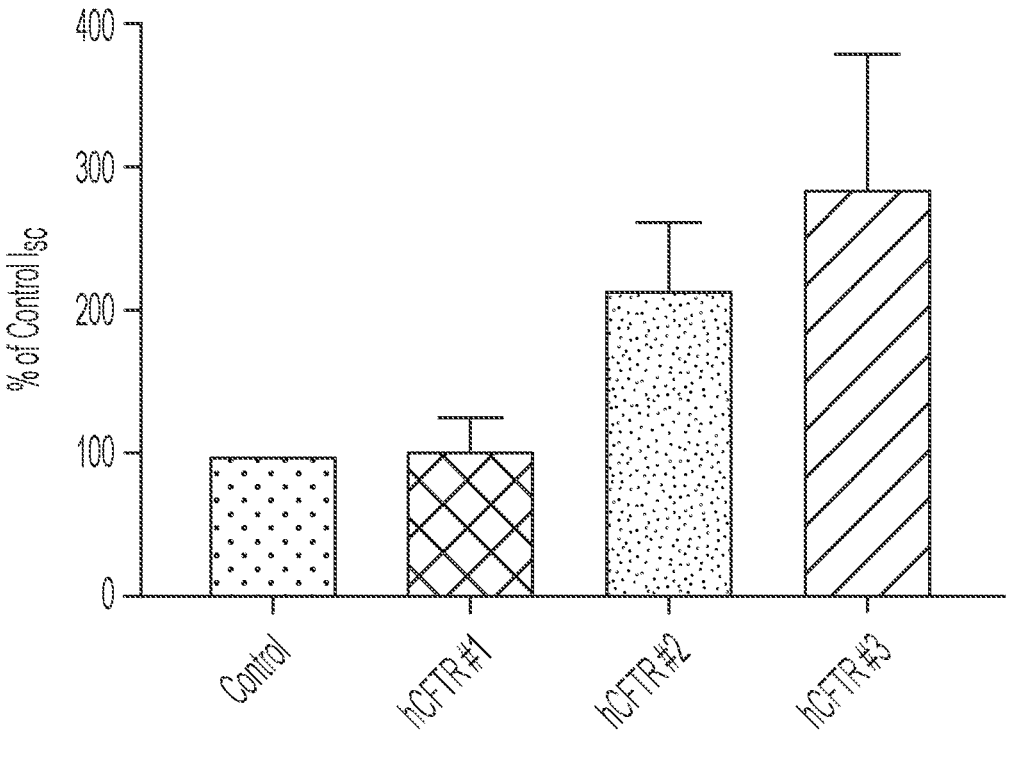
FIG. 3B illustrates an example bar plot illustrating the change in hCFTR activity as depicted in FIG. 3A, expressed as a percentage of the activity of a reference mRNA encoding hCFTR.

Correctly translated and localized hCFTR protein produced from a hCFTR mRNA increases the short circuit current ($I_{SC}$) output within an Ussing epithelial voltage clamp apparatus when CFTR agonists (forskolin and VX-770 [Kalydeco®]) are applied. The application of CFTR antagonist CFTRinh-172 drives hCFTR into a blocked state. The $I_{SC}$ current polarity convention in this assay records apical-to-basolateral sodium current and basolateral-to-apical chloride current as negative values, and so if transfection with a test hCFTR mRNA generates a high negative value, it can be concluded that the encoded hCFTR protein is functional (FIG. 3A). Moreover, by transfecting equal amounts of mRNA, it can be assessed whether an mRNA produces a higher yield of hCFTR protein since protein yield and activity are correlated. Transfection of FRT epithelial cells with an mRNA having the hCFTR #1 coding sequence resulted in activity comparable to that achieved by transfection with the mRNA having the control hCFTR coding sequence (FIG. 3B). mRNAs encoding a nucleotide sequence encoding hCFTR generated by a method of the present invention resulted in significantly increased activity. Consistent with the higher protein yields observed in Example 2, hCFTR protein produced from mRNA encoding hCFTR #2 resulted in more than 2-fold higher activity relative to the control mRNA, and hCFTR protein produced from an mRNA encoding hCFTR #3 resulted in 3-fold higher activity relative to the control mRNA. This confirms that the higher protein yield resulting from hCFTR #2 and hCFTR #3 observed in Example 2 directly correlates with higher functional activity, demonstrating that codon optimization in accordance with a method of the present invention does not negatively impact the functional activity of the encoded protein.

In summary, codon optimization according to a method of the present invention results in higher expression of the encoded protein in human cells, and the expressed protein provides full functional activity in a model system that is a highly relevant model for human therapy.

Example 4. Evaluating Codon Optimized Wild-Type CFTR Constructs Against Activated CFTR Construct In this example, expression and activity of the codon optimized wild-type CFTR construct was compared with a non-codon optimized wild-type CFTR construct and activated CFTR mutant constructs.

The present inventors have developed mRNAs encoding engineered or mutant CFTR proteins that show increased activity and/or stability. In particular, an engineered CFTR protein may contain one or more modifications that mimic phosphorylated residue in the R domain (R Domain Phosphomimetic mutation). These mutations lead to activation and opening of the CFTR chloride channel. Another strategy used to engineer activation mutants of CFTR is to mutate residues involved in ATP gating (e.g. E1371Q). CFTR proteins undergo ubiquitination at lysine residues. Amino acid mutations at lysine residues that result in a substitution of the lysine to another amino acid residue results in enhanced stability and protein expression of the CFTR protein (e.g. K14R). Example 3 showed that codon optimized wild-type CFTR constructs of the present invention have higher activity than the reference CFTR mRNA construct. To further evaluate the expression and activity of the codon optimized CFTR construct of the present invention, activated CFTR constructs and non-codon optimized CFTR construct listed in Table 3 were used in this experiment for comparison.

TABLE 3

| Various CFTR Wild-Type and Mutant Constructs | |
| --- | --- |
| Engineered CFTR | Mutations |
| WT | Wild-type |
| CO WT | Codon optimized wild-type |
| E1371Q/K14R | K14R, E1371Q |
| 13E | S422E, S660E, S670E, S686E, T690E, S700E, S712E, S753E, T787E, T788E, T790E, S795E, S813E |

TABLE 3-continued

| Various CFTR Wild-Type and Mutant Constructs | |
| --- | --- |
| Engineered CFTR | Mutations |
| 13E/K14R | K14R, S422E, S660E, S670E, S686E, T690E, S700E, S712E, S753E, T787E, T788E, T790E, S795E, S813E |
| 15E | S422E, S660E, S670E, S686E, T690E, S700E, S712E, S737E, S753E, S768E, T787E, T788E, T790E, S795E, S813E |
| 15E/K14R | K14R, S422E, S660E, S670E, S686E, T690E, S700E, S712E, S737E, S753E, S768E, T787E, T788E, T790E, S795E, S813E |

Figure 4A:
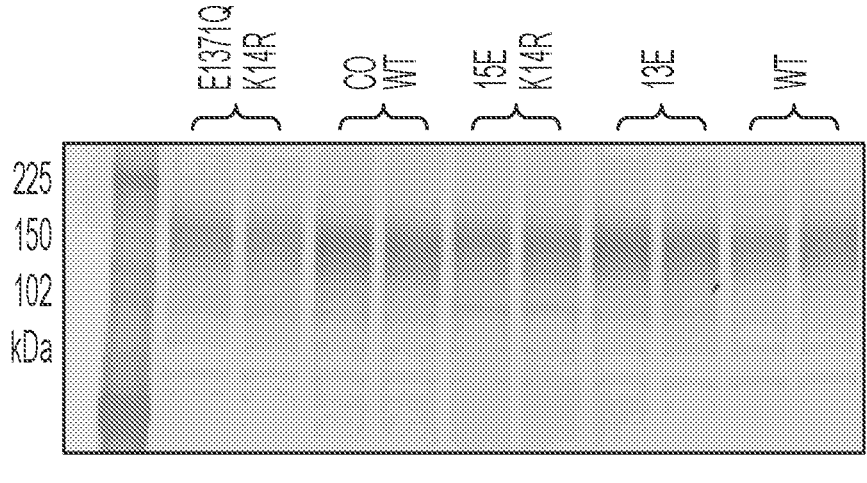
FIG. 4A is an exemplary gel that depicts the banding patterns of various CFTR sequences.
Figure 4B:
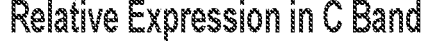
FIG. 4B is a bar graph that depicts the relative expression of various CFTR sequences in the C band.
Figure 4B:
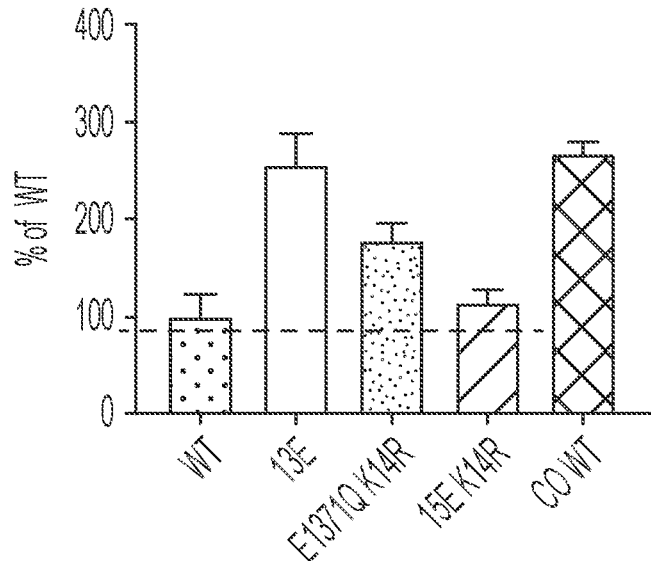
Figure 4C:
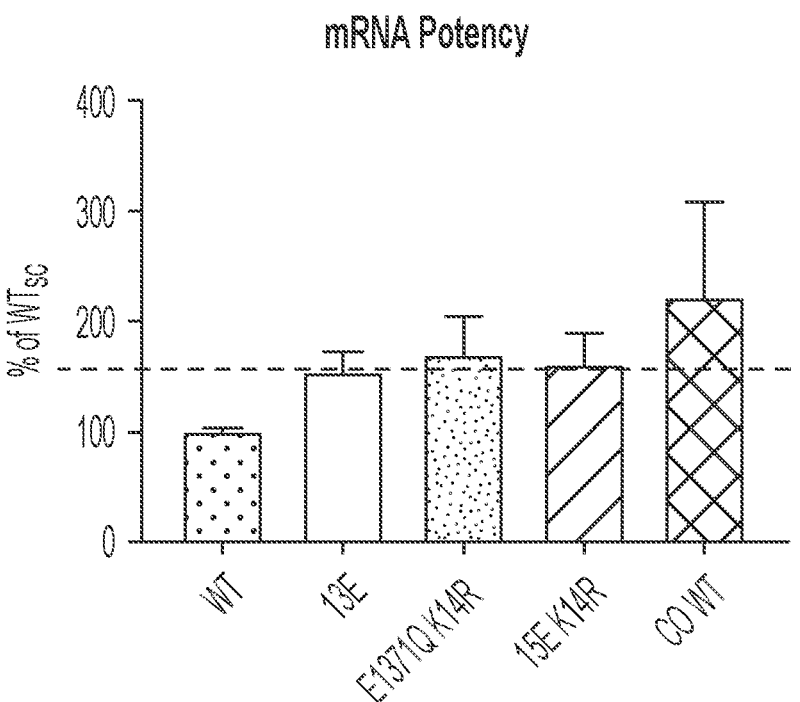
FIG. 4C is a bar graph that depicts CFTR mRNA potency of various CFTR sequences.

First, studies were also performed to assess in vitro translation of codon-optimized wild-type CFTR and the CFTR mutants. The data from these studies showed that codon optimized WT sequence, 13E and E1371Q K14R variants showed increased expression in the C band of HEK293 lysates (FIGS. 4A, and 4B). The "C band" refers to mature complex glycosylated form of CFTR. Additionally, codon optimized WT CFTR showed higher potency than the non-codon optimized WT CFTR (FIG. 4C).

Figure 5A:
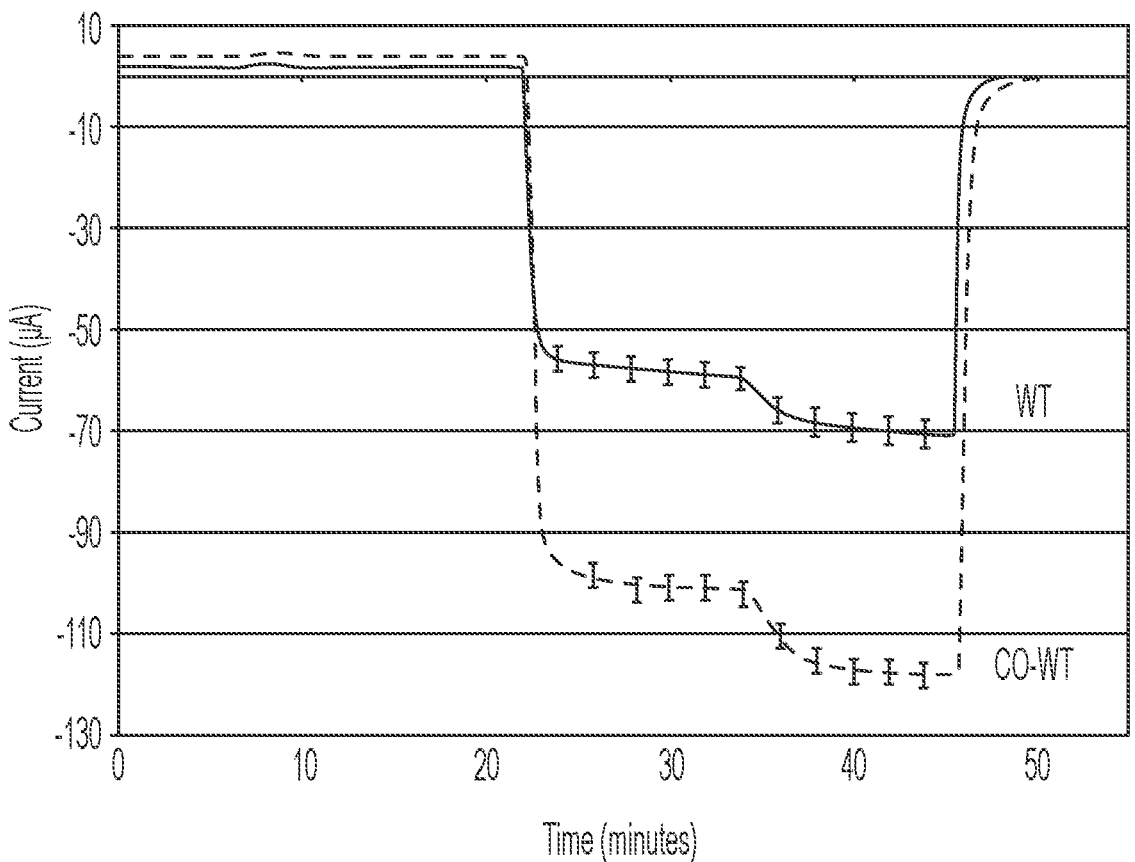
FIGS. 5A and 5B are exemplary graphs that show short-circuit conductivity measured by Ussing chamber of various codon-optimized and non-codon optimized CFTR constructs.
Figure 5B:
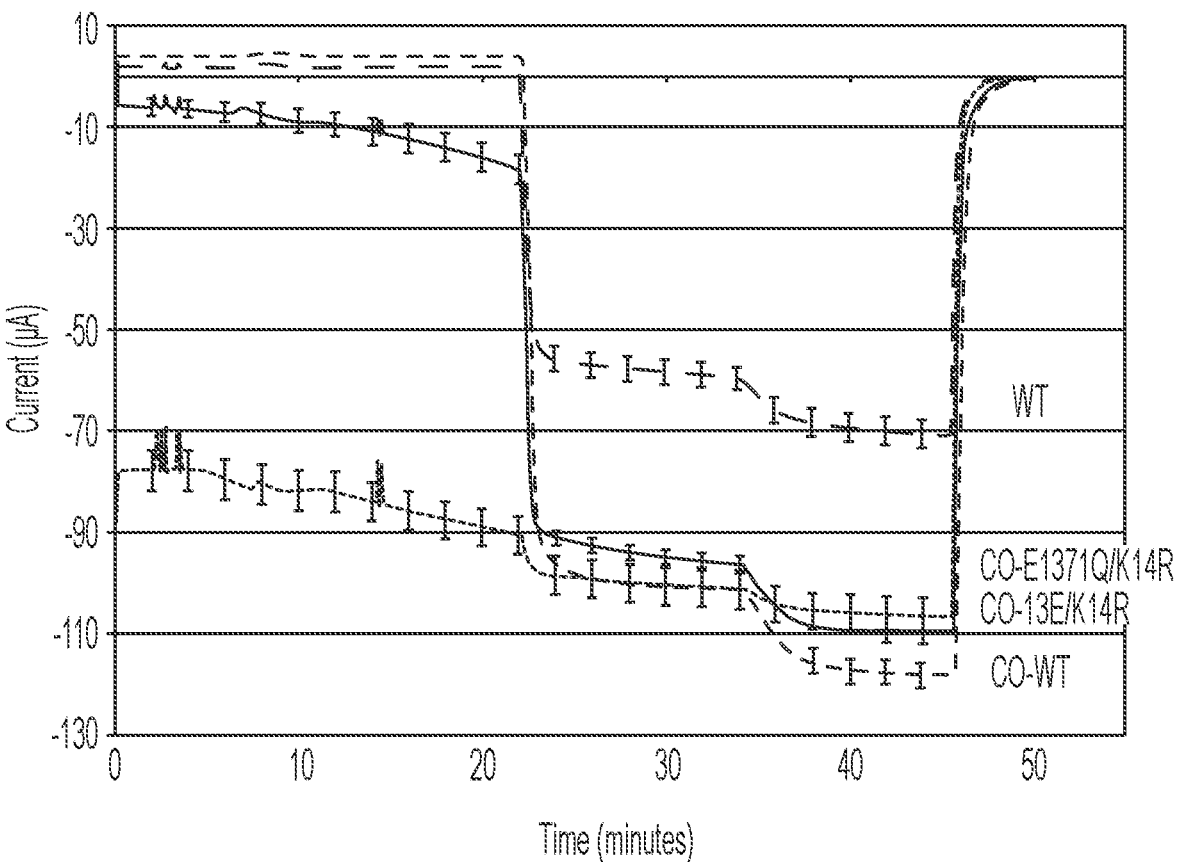

Next, codon-optimized CFTR sequences (both WT and mutants) were assessed against the non-codon optimized WT CFTR in Ussing Chamber assay. The data from these assays showed that codon-optimized WT CFTR showed increased activity in Ussing Chamber assays compared to non-codon optimized CFTR (FIG. 5A). Notably, CO WT showed comparable activity to codon-optimized activated CFTR mutant constructs (FIG. 5B). It was surprising to see that the activity of the wild-type CFTR protein could be enhanced significantly without introducing an amino acid mutation.

Figure 5C:
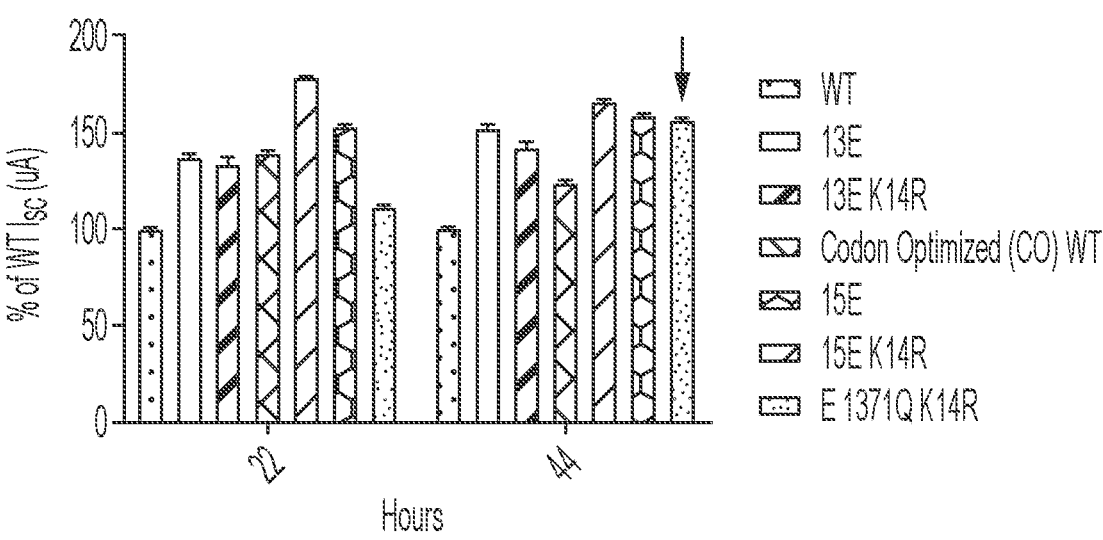
FIG. 5C is an exemplary bar graph representation of maximum activation current for various CFTR constructs in Ussing chamber assay at 22 and 44 hours.

Duration of activity of various CFTR constructs listed in Table 3 were tested using a time-course Ussing chamber assay. Activity of the CFTR proteins were measured at 22 and 44 hours. Short-circuit current ($I_{SC}$), the movement of ions as measured in the Us sing chamber from active transport, was plotted for each CFTR protein at 22 and 44 hours. FIG. 5C shows that the codon optimized WT CFTR had high remaining activity at 44 hours, significantly more than the non-codon optimized counterpart.

Figure 6:
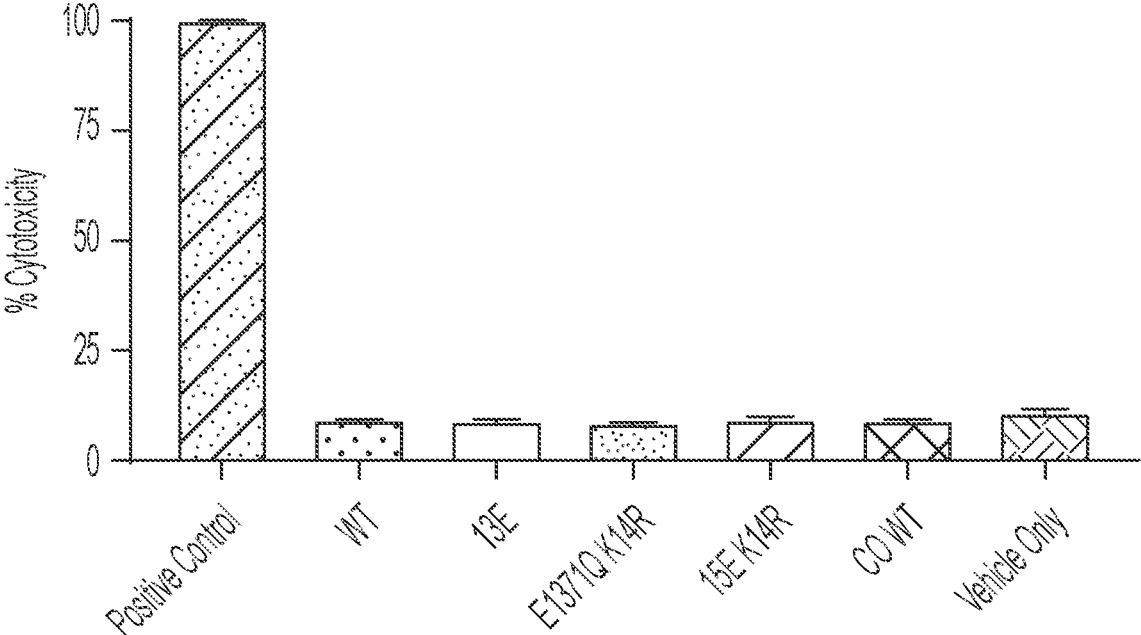
FIG. 6 is an exemplary bar graph that depicts the results of an assay to assess cytotoxicity of various CFTR mRNA sequences.

In vitro tolerability of the mutant CFTR mRNAs was also assessed in HEK293 cells using a commercially available cytotoxicity assay. The data from these studies showed that none of the CFTR variants, including the codon-optimized WT CFTR, demonstrated increased cytotoxicity when compared to the vehicle control in HEK293 cells (FIG. 6).

Overall, these data show that the CFTR mRNAs that were codon-optimized according to the present invention show significantly higher activity, which are particularly useful for treating cystic fibrosis by mRNA therapeutics.

Example 5. Synthesis of Lipids for Use in
Pulmonary Delivery

Synthesis of cationic lipids of the present invention are
described in this example.
1. GL-TES-SA-DME-E18-2

20

Synthetic Scheme

Linoleic acid oxalyl
chloride

2

1

3 oxalyl
chloride

3-Cl

4a

-continued

Compound I

Synthetic Protocol

Synthesis of (9Z,12Z)-Octadeca-9,12-dienoyl chloride (2)

To a solution of Linolenic acid (1.0 g, 3.6 mmol) in 10 mL dichloromethane at 0° C., was added N, N-dimethylformamide (0.1 mL) and oxalyl chloride (1.2 mL, 14.3 mmol). The reaction mixture was warmed to room temperature and stirred for 3 h. The solvent was removed to the under reduced pressure, and the crude was used in next step without further purification.

Synthesis of 2-((1,3-Bis(((9Z,12Z)-octadeca-9,12-dienoyl)oxy)-2-((((9Z,12Z)-octadeca-9,12-dienoyl)oxy)methyl)propan-2-yl)amino)ethane-1-sulfonic acid (3)

To a solution of (9Z,12Z)-octadeca-9,12-dienoyl chloride 2 (1.1 g, 3.6 mmol) in anhydrous N,N-dimethylacetamide (5.0 mL) and N-methyl morpholine (3.0 mL), was added 2-((1,3-dihydroxy-2-(hydroxymethyl)propan-2-yl)amino) ethane-1-sulfonic acid (1, TES) (200 mg, 0.87 mmol). The reaction mixture was heated to 55° C. for 3 h. MS analysis showed the formation of desired product. The reaction mixture was cooled to room temperature, diluted with water (100 mL) and extracted with dichloromethane (2×100 mL). The combined organic layer was washed with saturated brine (100 mL) and dried over anhydrous sodium sulfate. The solvent was removed under vacuum, and the residue was purified by column chromatography (40 g SiO$_2$: 0 to 10% methanol in dichloromethane gradient) to obtain 2-((1, 3-bis(((9Z,12Z)-octadeca-9,12-dienoyl)oxy)-2-((((9Z,12Z)-octadeca-9,12-dienoyl)oxy)methyl)propan-2-yl)amino)eth-ane-1-sulfonic acid as colorless solid (562 mg, 47% yield).

Synthesis of 2-((2-(Chlorosulfonyl)ethyl)amino)-2-4
((9Z,12Z)-octadeca-9,12-dienoyl)oxy)methyl)pro-
pane-1,3-diyl (9Z,9'Z,12Z,12' Z)-bis(octadeca-9,12-
dienoate) (3-Cl)

To a solution of 2-((1,3-bis(((9Z,12Z)-octadeca-9,12-di-
enoyl)oxy)-2-((((9Z,12Z)-octadeca-9,12-dienoyl)oxy)
methyl)propan-2-yl)amino)ethane-1-sulfonic acid 3 (210
mg, 0.82 mmol) in anhydrous dichloromethane (5.0 mL) at
0° C. was added N, N-dimethylformamide (0.05 mL) and
oxalyl chloride (0.08 mL, 2.1 mmol). The reaction mixture
was warmed to room temperature and stirred for 3 h. The
solvent was removed to the dryness under reduced pressure
to give 2-((2-(chlorosulfonyl)ethyl)amino)-2-((((9Z,12Z)-
octadeca-9,12-dienoyl)oxy)methyl)propane-1,3-diyl    (9Z,
9'Z,12Z,12'Z)-bis(octadeca-9,12-dienoate), which was used
in next step without further purification.

Synthesis of 2-((2-(N-(2-(dimethylamino)ethyl)sul-
famoyl)ethyl)amino)-2-((((9Z,12Z)-octadeca-9,12-
dienoyl)oxy)methyl)propane-1,3-diyl (9Z,9'Z,12Z,
12'Z)-bis(octadeca-9,12-dienoate) (Compound I)

(Compound I)

To a solution of 2-((2-(chlorosulfonyl)ethyl)amino)-2-((((9Z,12Z)-octadeca-9,12-dienoyl)oxy)methyl)propane-1,3-diyl (9Z,9'Z,12Z,12'Z)-bis(octadeca-9,12-dienoate) 3-Cl (210 mg, 0.82 mmol) in anhydrous dichloromethane (5.0 mL) at 0° C. was added $N^1,N^1$-dimethylethane-1,2-diamine (182 mg, 2.1 mmol). The reaction mixture was warmed to room temperature and stirred for 3 h. The reaction was quenched by addition of water, and the mixture was extracted with dichloromethane (2×100 mL). The combined organic layer was washed with saturated brine (100 mL) and dried over anhydrous sodium sulfate. The solvent was removed, and the crude was purified by column chromatography (40 g $SiO_2$: 0 to 15% methanol in dichloromethane gradient) to obtain 2-((2-(N-(2-(dimethylamino)ethyl)sulfamoyl)ethyl)amino)-2-((((9Z,12Z)-octadeca-9,12-dienoyl)oxy)methyl)propane-1,3-diyl (9Z,9'Z,12Z,12'Z)-bis(octadeca-9,12-dienoate) as yellow oil (139 mg, 62% yield).

1H NMR (300 MHz, Chloroform-d) δ 5.26-5.44 (m, 12H), 4.09 (s, 6H), 3.06-3.18 (m, 6H), 2.75 (t, 6H), 2.47 (t, 2H), 2.32 (t, 6H), 2.24 (s, 6H), 2.00-2.10 (m, 12H), 1.52-1.65 (m, 4H), 1.20-1.40 (m, 44H), 0.88 (t, 9H).

APCI-MS analysis: Calculated C64H115N3O8S, [M+H]=1186.7, observed=1186.8.

2. GL-TES-SA-DMP-E18-2

-continued

3

(Compound II)

Synthetic Pathway

Linoleic acid

2

-continued

3

3-Cl

US 12,605,399 B2

111
-continued

Compound II

R⁵ =

Synthetic Protocol

Compound II was prepared following the above representative procedure in similar yields to those obtained for Compound I.

Linoleic acid is treated with a chlorinating reagent such as oxalyl chloride to provide the acyl chloride compound 2. Reaction of compound 2 with a nucleophilic compound, such as the buffer compound 1, affords compound 3. Compound 3 is treated with a chlorinating agent such as oxalyl chloride to provide the electrophilic compound 3-Cl. Reaction of 3-Cl with a nucleophile such as compound 4b then affords compound II.

The reaction conditions used were as follows:

| SM | Product | Reaction Conditions | Scale | Yield |
|---|---|---|---|---|
| Linoleic acid | 2 | Oxalyl chloride, DMF DCM | 1.0 g of linoleic acid | — |
| 1 & 2 | 3 | Dimethylacetamide + N-Methylmorpholine | 200 mg of 1 | 562 mg 47% yield |
| 3 | 3-Cl | Oxalyl chloride, DMF DCM | 200 mg of 3 | — |
| 3-Cl & 4b | Compound II | DCM | 200 mg of 3-Cl | 105 mg (49% over 2 steps) |

1H NMR (300 MHz, Chloroform-d) δ 5.24-5.42 (m, 12H), 4.08 (s, 6H), 3.17 (t, 2H), 3.06 (bs, 4H), 2.75 (t, 6H), 2.43 (t, 2H), 2.31 (t, 6H), 2.23 (s, 6H), 1.98-2.08 (m, 12H), 1.70 (quint, 2H), 1.52-1.63 (m, 4H), 1.17-1.45 (m, 44H), 0.87 (t, 9H).

APCI-MS analysis: Calculated C65H117N3O8S, [M+H]=1100.7, observed=1100.8.

3. TL1-01D-DMA

112
Synthetic Scheme

A1

A2-1

EDCl DMAP
DCM, rt, 24 h

A3-1

A3-1

A4-1
Pyridine, DMAP CH₂Cl₂, RT 24 hours

Compound (1)

Synthetic Protocol

Synthesis of (trioctyl 2-hydroxypropane-1,2,3-tricarboxylate)

To a solution of citric acid A1 (2.1 g, 11.0 mmol) and 1-octanol A2-1 (9.4 g, 72.6 mmol) in dichloromethane (40 mL), DMAP (1.34 g, 11.0 mmol) and EDCI (14.3 g, 72.6 mmol) were added, and the resulting mixture was stirred at room temperature 24 h. The reaction mixture was evaporated under vacuum. The residue was dissolved in dichloromethane (200 mL) and washed with brine (100 mL×3). After dried over anhydrous Na₂SO₄, the solvent was evaporated, and the crude was purified by column chromatography (220 g SiO₂: 0 to 20% ethyl acetate in hexane gradient) to obtain (trioctyl 2-hydroxypropane-1,2,3-tricarboxylate) as colorless oil (5.2 g, 90%).

Synthesis of (trioctyl 2-((3-(dimethylamino)propanoyl)oxy)propane-1,2,3-tricarboxylate)

To a solution of trioctyl 2-hydroxypropane-1,2,3-tricarboxylate A3-1 (0.528 g, 1.0 mmol), DMAP (122 mg, 1.0 mmol) and pyridine (316 mg, 4.0 mmol) in 10 mL dichloromethane, 3-(dimethylamino)propanoyl chloride A4-1 (271 mg, 2.0 mmol) was added at 0° C., and then the resulting mixture was stirred at room temperature for 24 h. The reaction mixture was evaporated under vacuum. The residue was dissolved in dichloromethane (100 mL) and washed with brine (80 mL×3). After dried over anhydrous Na₂SO₄, the solvent was evaporated, and the crude was purified by column chromatography (80 g SiO₂: 0 to 10% methanol in dichloromethane gradient) to obtain trioctyl 2-((3-(dimethylamino)propanoyl)oxy)propane-1,2,3-tricarboxylate as colorless oil (210 mg, 33%).

Alternatively, to a suspension of 3-(dimethylamino)propanoic acid (8.02 g, 68.5 mmol) in 150 mL dichloromethane, was added EDCI (13.1 g, 68.5 mmol) and DMAP (2.09 g, 17.1 mmol) at 0° C., and the resulting mixture was stirred at this temperature for 5 min. A solution of trioctyl 2-hydroxypropane-1,2,3-tricarboxylate A3-1 (9.05 g, 17.1 mmol) in 10 mL dichloromethane was added, and then the resulting mixture was stirred at room temperature for 48 h. The reaction mixture was diluted with dichloromethane, washed with saturated sodium bicarbonate and brine. After dried over sodium sulfate, the organic layer was evaporated under vacuum. The residue was purified by column chromatography (220 g SiO₂: 0 to 10% methanol in dichloromethane gradient) to obtain trioctyl 2-((3-(dimethylamino)propanoyl)oxy)propane-1,2,3-tricarboxylate as colorless oil (4.2 g, 38%).

¹H NMR (300 MHz, CDCl₃) δ 4.56 (s, br., 6H), 4.24 (t, 2H), 4.12 (s, 2H), 2.55 (t, 2H), 2.28-2.17 (m, 14H), 1.63-1.48 (m, 8H), 1.25 (s, br., 32H), 0.86 (t, 12H).

APCI-MS analysis: Calculated C35H65NO8, [M+H] =627.9, Observed=628.5.

4. TL1-04D-DMA

TD1-04D-DMA can be made in a similar manner as TD-01D-DMA, which is described above.

5. SY-3-E14-DMAPr

Synthetic Scheme $R^A = R^B = C_{12}H_{25}$

117

Synthesis of 3-(Dimethylamino)propyl
4-hydroxy-3,5-dimethoxybenzoate (6)

118

To a suspension of syringic acid 5 (7.5 g, 0.04 moles) in 100 mL dichloromethane at 0° C. was added oxalyl chloride (12.8 mL, 0.15 mole) followed by dimethylformamide (5 drops), and the resulting mixture was stirred for 2 h at this temperature. The reaction mixture was evaporated to dryness, and the residue was dissolved in 100 mL dichloromethane. After cooling to 0° C., 3-(dimethylamino)propan-1-ol 2 (4.5 mL, 40 mmol) was added slowly, and the reaction mixture was stirred at room temperature overnight. The precipitate was filtered to give 3-(dimethylamino)propyl 4-hydroxy-3,5-dimethoxybenzoate 6 as white solid (6.2 g, 58%).

6. TL1-10D-DMA

TD1-04D-DMA can be made in a similar manner as TD-01D-DMA, which is described above.

7. HEP-E3-E10

Synthetic Scheme

Scheme 1

E3-E10
[2]

HEP
[1]

EDC, DMAP
DIPEA, DCE, DMF
rt, overnight

[3]

HF, pyridine
rt, overnight

HEP-E3-E10
[4]

Synthetic Protocol

Synthesis of [3]

As set out in Scheme 1: To a solution containing HEP [1] (0.100 g, 0.494 mmol, 1.0 eq), E3-E10 [2] (0.668 g, 1.038 mmol, 2.1 eq), 1 ml of dimethylformamide, 3 ml of dichloroethane, diisopropylethylamine (0.344 µL, 1.98 mmol, 4.0 eq), and N,N-Dimethylaminopyridine (0.024 g, 0.198 mmol, 0.4 eq) was added 1-Ethyl-3-(3-dimethylaminopropyl)carbodiimide (0.285 g, 1.48 mmol, 3.0 eq) and allowed to react at room temperature overnight (18 hr). Afterwards, the reaction mixture was concentrated using a rotavapor and purified using a Buchi Combi-flash system on 12 g, 40 m-sized silica gel columns using hexanes/ethyl acetate as the mobile phase, yielding a colorless oil (70% yield).

Synthesis of HEP-E3-E10 [4]

As set out in Scheme 1: To a 20 ml Polypropylene scintillation vial equipped with a PTFE stir-bar was added [3] (0.500 g, 0.344 mmol, 1.0 eq) along with 4 ml of dry tetrahydrofuran. The vial was cooled to 0-5° C. on an ice bath and HF/pyridine (1.76 ml, 67.86 mmol, 197.3 eq) was added dropwise. After addition, the reaction vial was allowed to warm to room temperature and stirred overnight (18 hr). Afterwards, the reaction mixture was neutralized with saturated sodium bicarbonate at 0° C. Ethyl acetate was used for extraction (3×). The organic layers were combined, washed with saturated sodium chloride (4×), dried with sodium sulfate, filtered, and rotovaped to yield an off-yellow oil. This oil was further purified using a Buchi Combi-flash system on 12 g, 40 m-sized silica gel columns using dichloromethane/methanol (3% methanol) as the mobile phase, yielding a colorless oil (60% yield).

1H NMR (400 MHz, CDCl$_3$) 4.16 (m, 4H), 3.60 (m, 4H), 2.97 (m, 3H), 2.78 (d, 3H), 2.58 (m, 9H), 2.37 (m, 12H), 2.15 (m, 2H), 1.78 (m, 4H), 1.44 (m, 7H), 1.36 (m, 9H), 1.26 (br, 45H), 1.05 (d, 6H), 0.87 (t, 12H).

Expected M/Z=998.59, Observed=998.0.

8. HEP-E4-E10

Synthetic Scheme

Scheme 2

E4-E10
[11]

HEP
[1]

EDC, DMAP
DIPEA, DCE, DMF
rt, overnight

-continued

[12]

HF, pyridine
rt, overnight

HEP-E3-E10
[13]

Synthetic Protocol

Synthesis of [12]

As set out in Scheme 2: To a solution of HEP [1] (0.100 g, 0.494 mmol, 1.0 eq), E4-E10 [11] (0.683 g, 1.038 mmol, 2.1 eq), 1 ml of dimethylformamide, 3 ml of dichloroethane, diisopropylethylamine (0.344 μL, 1.98 mmol, 4.0 eq), and N,N-Dimethylaminopyridine (0.024 g, 0.198 mmol, 0.4 eq) was added 1-Ethyl-3-(3-dimethylaminopropyl)carbodiimide (0.285 g, 1.48 mmol, 3.0 eq) and allowed to react at room temperature overnight (18 hr). Afterwards, the reaction mixture was concentrated using a rotavapor and purified using a Buchi Combi-flash system on 12 g, 40 m-sized silica gel columns using hexanes/ethyl acetate as the mobile phase, yielding a colorless oil (63.3% yield).

Synthesis of HEP-E4-E10 [13]

As set out in Scheme 2: To a 20 ml Polypropylene scintillation vial equipped with a PTFE stir-bar was added [12] (0.450 g, 0.303 mmol, 1.0 eq) along with 4 ml of dry tetrahydrofuran. The vial was cooled to 0-5° C. on an ice bath and HF/pyridine (1.55 ml, 59.920 mmol, 197.3 eq) was added dropwise. After addition, the reaction vial was allowed to warm to room temperature and stirred overnight (18 hr). Afterwards, the reaction mixture was neutralized with saturated sodium bicarbonate at 0° C. Ethyl acetate was used for extraction (3×). The organic layers were combined, washed with saturated sodium chloride (4×), dried with sodium sulfate, filtered, and rotovaped to yield an off-yellow oil. This oil was further purified using a Buchi Combi-flash system on 12 g, 40 m-sized silica gel columns using dichloromethane/methanol (3%) as the mobile phase, yielding a colorless oil (48.4% yield).

1H NMR (400 MHz, CDCl$_3$) 4.16 (t, 4H), 3.62 (br, 4H), 2.96 (q, 3H), 2.76 (d, 4H), 2.56 (m, 8H), 2.40 (m, 4H), 2.32 (t, 4H), 2.13 (t, 2H), 1.61 (m, 4H), 1.46 (m, 8H), 1.37 (m, 8H), 1.28 (br, 44H), 1.03 (d, 6H), 0.87 (t, 12H), 13C NMR (400 MHz, CDCl$_3$) 173.65 (2C), 69.65 (2C), 68.04 (2C), 62.84 (2C), 61.82 (2C), 61.44 (2C), 60.89 (2C), 55.57 (4C), 51.55 (2C), 35.35 (4C), 34.20 (2C), 32.09 (7C), 30.00 (5C), 29.77 (6C), 29.47 (6C), 26.93 (2C), 25.84 (5C), 22.84 (9C), 17.77 (2C), 14.30 (7C).

Expected M/Z=1025.64, Observed=1025.8.

9. Guan-SS-Chol

Guan-SS-Chol can be made according to methods described in International Publication No. WO 2018/ 089801, which is hereby incorporated by reference in its entirety. Guan-SS-Chol and Formula (V) (HGT4002) are used interchangeably.

Example 6. Evaluating Cationic Lipids for Pulmonary Delivery

In this example, various cationic lipids were tested for in vivo efficacy when mRNA encapsulated in lipid nanopar- ticles (mRNA-LNP) were administered to mice by pulmo- nary delivery. The cationic lipids were tested for both potency, as determined by levels of protein production, and tolerability, as determined by side effects associated with clearance and metabolism.

Figure 7:
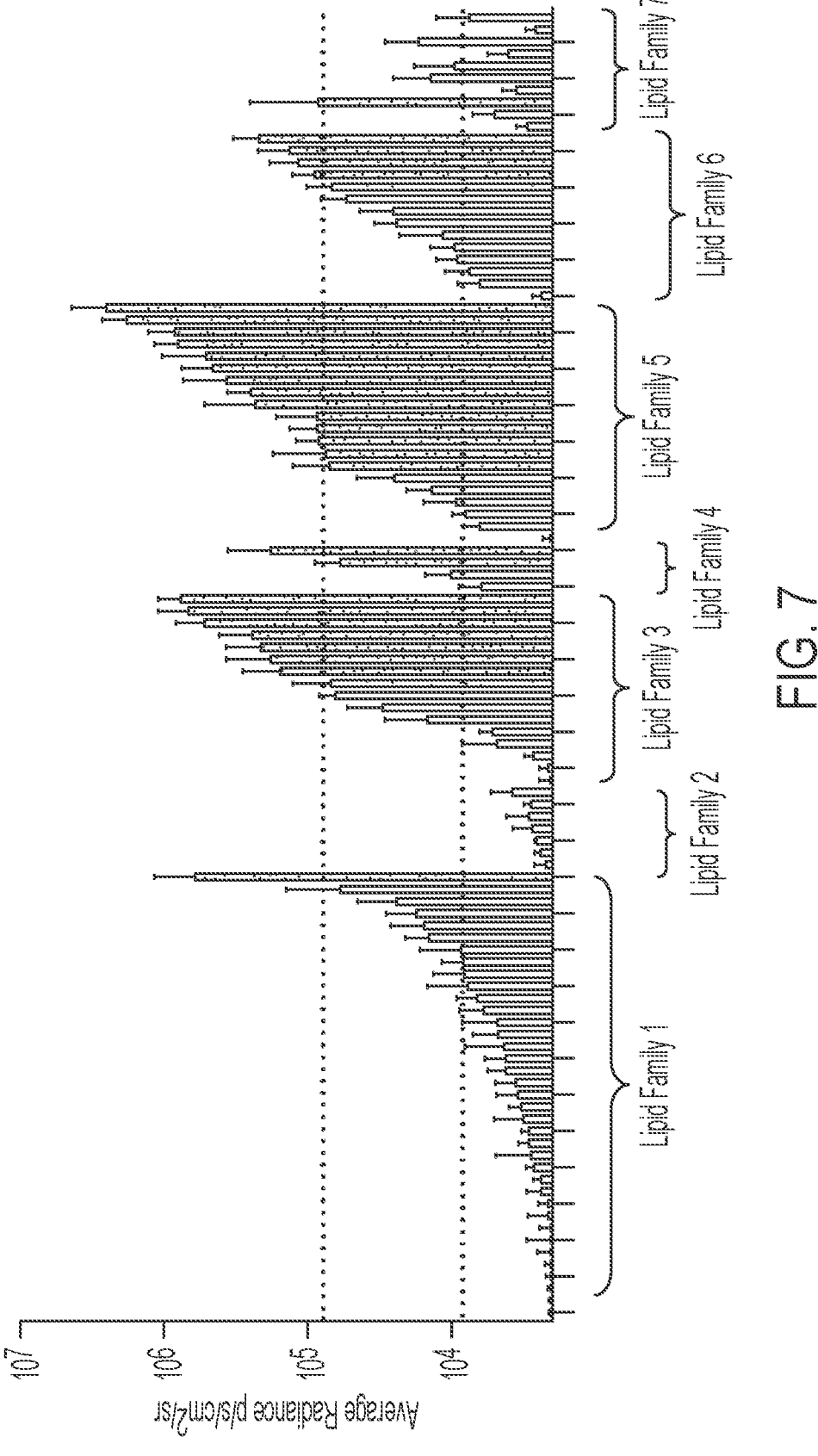
FIG. 7 is an exemplary bar graph that depicts the amount of radiance produced by luciferase protein expressed in mice after administration of mRNA-LNPs, each comprising a different cationic lipid component. The horizontal lines in the graph around $10^4$ p/s/cm$^2$sr represent the historical radiance/expression of pulmonary-delivered (e.g., nebulized) FFL mRNA encapsulated in an LNP comprising ICE as a cationic lipid. The horizontal lines in the graph around $10^6$ p/s/cm$^2$sr represent the historical radiance/expression of pulmonary-delivered (e.g., nebulized) FFL mRNA encapsulated in an LNP comprising ML2 as a cationic lipid. These thresholds can be used to screen lipids for pulmonary delivery.

About 150 cationic lipids were tested. (FIG. 7). Each cationic lipid was used in preparing lipid nanoparticles encapsulating mRNA encoding firefly luciferase protein (FFL mRNA) according to methods known in the art. For example, suitable methods for mRNA encapsulation include methods described in International Publication Nos. WO2016/004318 and WO 2018/089801, which is hereby incorporated by reference in its entirety. The tested lipid nanoparticles comprised a lipid component consisting of a cationic lipid, a non-cationic lipid (DOPE), a PEG-modified lipid (DMG-PEG2K), and optionally cholesterol.

Lipid nanoparticle formulations comprising FFL mRNA were administered to male CD1 mice by a single intratra- cheal administration via nebulization using a Micros- prayer®. At approximately 5 hours post-dose, the animals were dosed with luciferin by intraperitoneal injection and all animals were imaged using an IVIS imaging system to measure luciferase production in the lung. FIG. 7 shows that each cationic lipid has various efficacy of in vivo protein expression in the lung. Some cationic lipids remarkably had greater than 50-fold increase in pulmonary protein expres- sion as compared to other cationic lipids.

Based on their performance in this in vivo screen, nine cationic lipids were selected for further investigation: GL-TES-SA-DME-E18-2, TL1-01D-DMA, SY-3-E14- DMAPr, TL1-10D-DMA, HGT4002 (also referred to herein as Guan-SS-Chol), GL-TES-SA-DMP-E18-2, HEP-E4- E10, HEP-E3-E10, and TL1-04D-DMA. Of these, HEP-E4- E10, HEP-E3-E10, GL-TES-SA-DME-E18-2, GL-TES- SA-DMP-E18-2, TL1-01D-DMA and TL1-04D-DMA displayed particularly high potency as determined by the average radiance detected in mouse lungs.

Example 7. Evaluating Lipid Nanoparticles for Protein Expression

In this example, cationic lipids were tested for both in vivo mRNA delivery and protein expression to evaluate potency and biodistribution. In this study, cationic lipids TL-10D-DMA, SY-3-E14-DMAPr, and TD1-04D-DMA were used to prepare lipid nanoparticles LNP-A, LNP-B, and LNP-C, respectively, encapsulating mCherry mRNA.

Figure 8A:
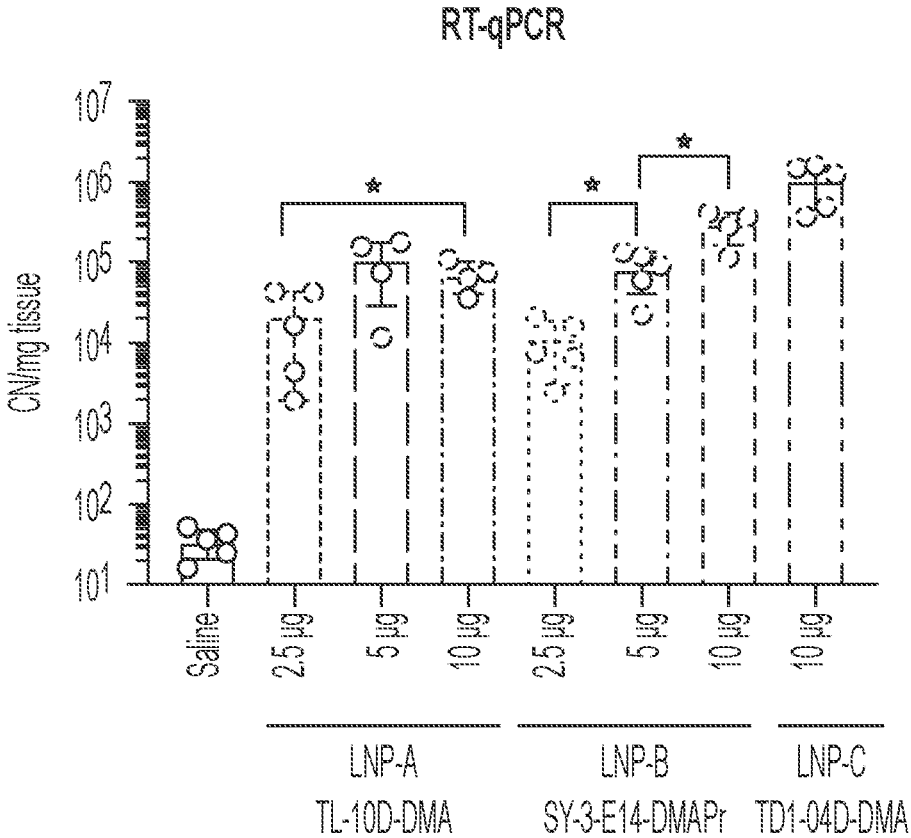
FIG. 8A is an exemplary bar graph that depicts the amount of mRNA delivered to the lung tissue as determined by RT-qPCR.
Figure 8B:
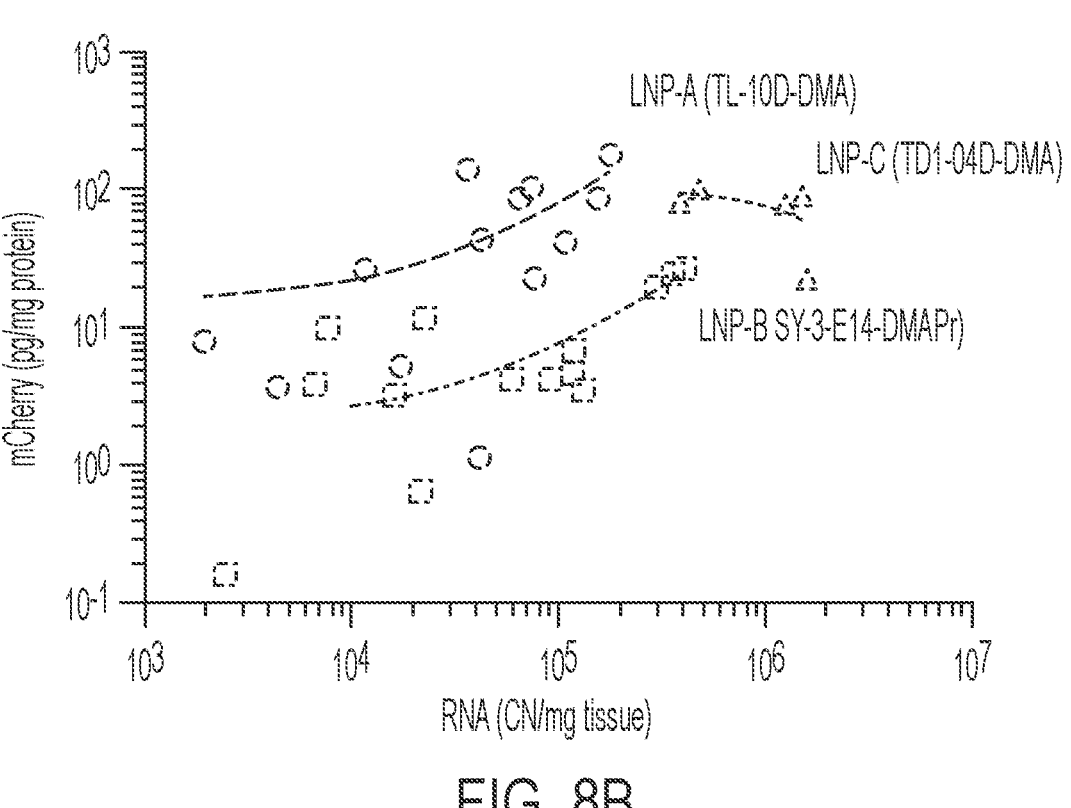
FIG. 8B is an exemplary plot that depicts the amount of mCherry protein (y-axis) produced per amount of mCherry mRNA (x-axis) delivered to the lung.

The mRNA-LNPs were administered to mice by intratra- cheal administration and the amount of mRNA delivered to the lung tissue was determined. As shown in FIG. 8A, all the mRNA-LNPs tested deliver mRNA more effectively to lung cells. To examine whether the amount of mRNA delivered to the lung cells correlates with protein expression in the lung, the amount of mCherry protein was determined by ELISA. FIG. 8B shows the amount of mRNA in the lung tissue in the x-axis and the amount of protein expressed in the lung in the y-axis. The data shows that certain LNPs have higher potency as shown by increased protein expression, even when the same amount of mRNA was delivered to the tissue. For example, for the same amount of $10^5$ CN/mg tissue RNA delivered, LNP-B resulted in about 10 pg/mg protein, whereas LNP-A resulted in about $10^2$ pg/mg protein.

Example 8. Evaluating Lipid Nanoparticles for Biodistribution by Pulmonary Delivery In this example, LNPs encapsulating mRNAs were tested for biodistribution when mRNA-LNPs were administered to mice by pulmonary delivery.

Figure 9A:
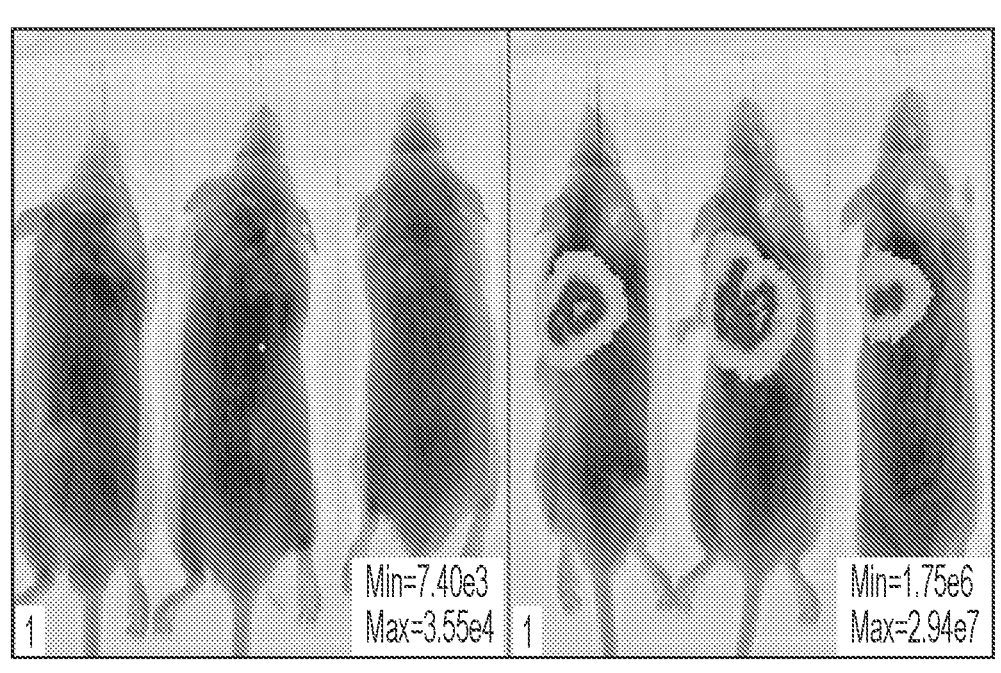
FIG. 9A is an exemplary imaging of whole mice that shows radiance of firefly luciferase expressed by the delivered mRNA-LNPs. The radiance shows that mRNA-LNPs were effectively delivered to mice lungs for in vivo expression.

First, a study was done to examine whether the mRNA- LNPs of the present invention are delivered effectively to the lungs in vivo. LNPs encapsulating FFL mRNA was admin- istered to CD-1 mice by intratracheal delivery, and radiance was detected at 24 hours post-administration. As shown in FIG. 9A, the results demonstrate that mRNA-LNPs were effectively delivered to the lungs of mice.

Figure 9B:
FIG. 9B is an exemplary imaging of mice by Cryofluorescence Tomography that shows expression of Cre recombinase mRNA. The imaging shows that expression of the delivered protein is detected in the lungs and branches of the airway, as indicated by the arrows.
Figure 9B:
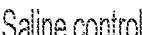
Figure 9B:

To identify which types of cells the mRNA-LNPs trans- fect in vivo, genetically modified mice were used whose cells, after successful transfection with Cre recombinase, express fluorescent tdTomato protein. Following in vivo administration of mRNA encoding Cre recombinase, it is possible to visualize successfully transfected cells in bulk tissues with single-cell resolution by detecting Cre-induced tdTomato expression. LNPs encapsulating Cre recombinase mRNA was administered to tdTomato transgenic mice by nebulization. After 48 hours, mice were imaged by Cryo- fluorescence Tomography. FIG. 9B shows that mRNA-LNPs were delivered effectively to the lung, and protein expres- sion was observed even in the branches of the airway, as indicated by the arrows.

Figure 9C:
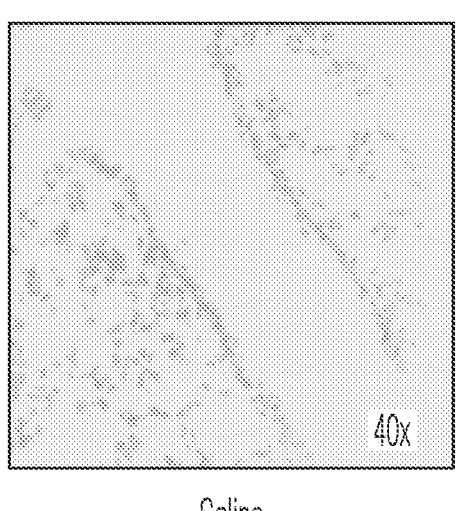
FIG. 9C is an exemplary immunofluorescence imaging of lung sections at 40× and 100× magnification. CFTR protein expressed by the delivered mRNA was evident in apical surface of the airways, as indicated by the arrows.
Figure 9C:
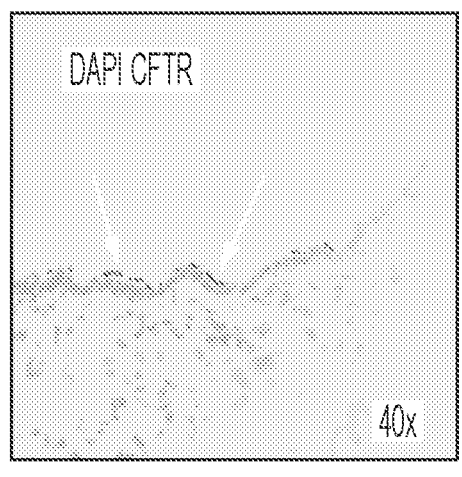
Figure 9C:
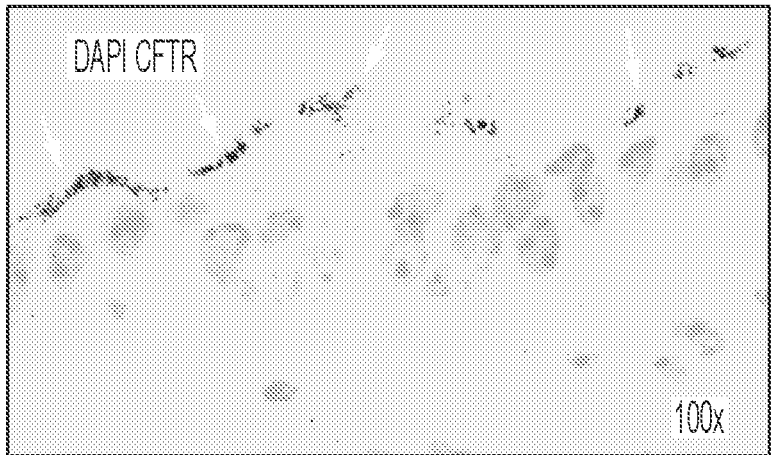

Next, to examine biodistribution and expression of mRNA-LNPs at high resolution, LNPs encapsulating CFTR mRNA were prepared. mRNA-LNPs were administered to CFTR knock-out (KO) mice by pulmonary delivery. Protein expression was detected by immunofluorescence. FIG. 9C shows that the CFTR proteins expressed by the delivered mRNA-LNPs were present on the apical surface of the airways, as indicated by the arrows, demonstrating the effectiveness of the mRNA-LNPs of the present invention.

Example 9. Evaluating Lipid Nanoparticles for Protein Expression by HBEC-ALI

In this example, LNPs encapsulating mRNAs were tested for protein expression using the HBEC-ALI (Human Bronchial Epithelial Cell—Air Liquid Interface) system. HBEC-ALI technique is advantageous as it reproduces a well differentiated airway epithelium with distinct, functional cells, allowing it to be used as a highly translatable airway cell model.

Figure 10A:
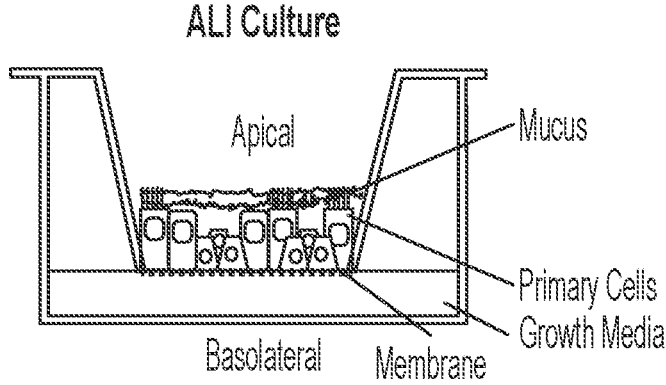
FIG. 10A is an exemplary HBEC-ALI (Human Bronchial Epithelial Cell—Air Liquid Interface) model and timeline for growing the ALI culture.
Figure 10A:
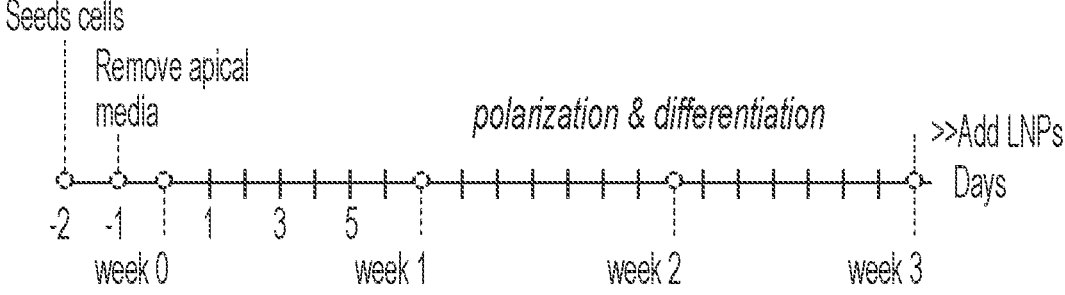
Figure 10B:
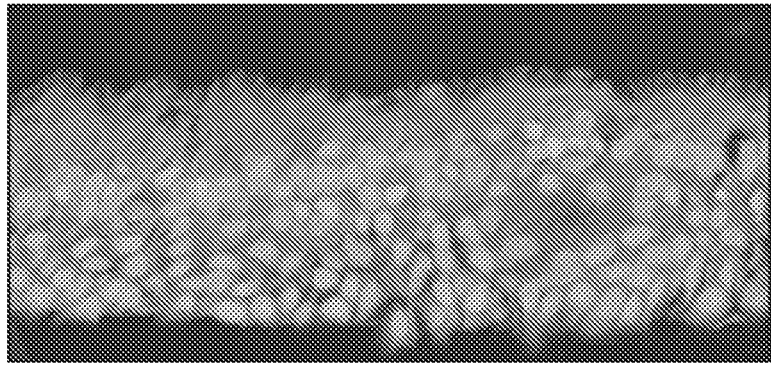
FIG. 10B is an exemplary imaging of the differentiated epithelium in HBEC-ALI model after staining with hematoxylin and eosin (H&E).

Obtaining a successful HBEC-ALI culture that can be used in future experiments is critical. Briefly, human bronchial epithelial cells were seeded on wells and grown in media. Upon reaching confluency, the apical media was removed and replaced with growth culture media. Cells were grown to allow polarization and differentiation before experiments with mRNA-LNPs were performed, as shown in FIG. 10A. The exemplary HBEC-ALI system schematic is shown in FIG. 10A. The differentiated epithelium were sectioned and stained with hematoxylin and eosin (H&E), as shown in FIG. 10B, which indicates the presence of multi-ciliated cells that can be used as airway cell model.

Figure 11A:
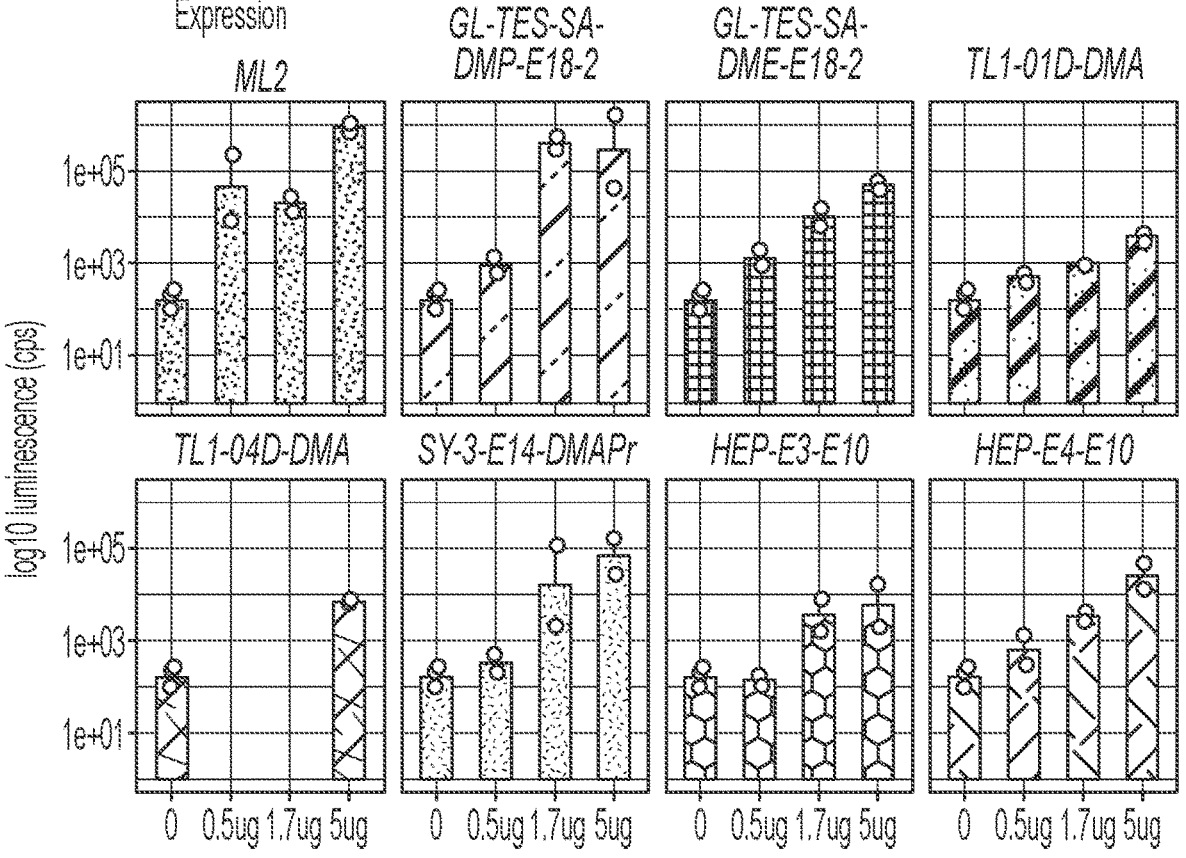
FIG. 11A is an exemplary bar graph that depicts the amount of luminescence produced (in log scale) by luciferase protein in cells in the HBEC-ALI model after transfection with mRNA-LNPs.
Figure 11B:
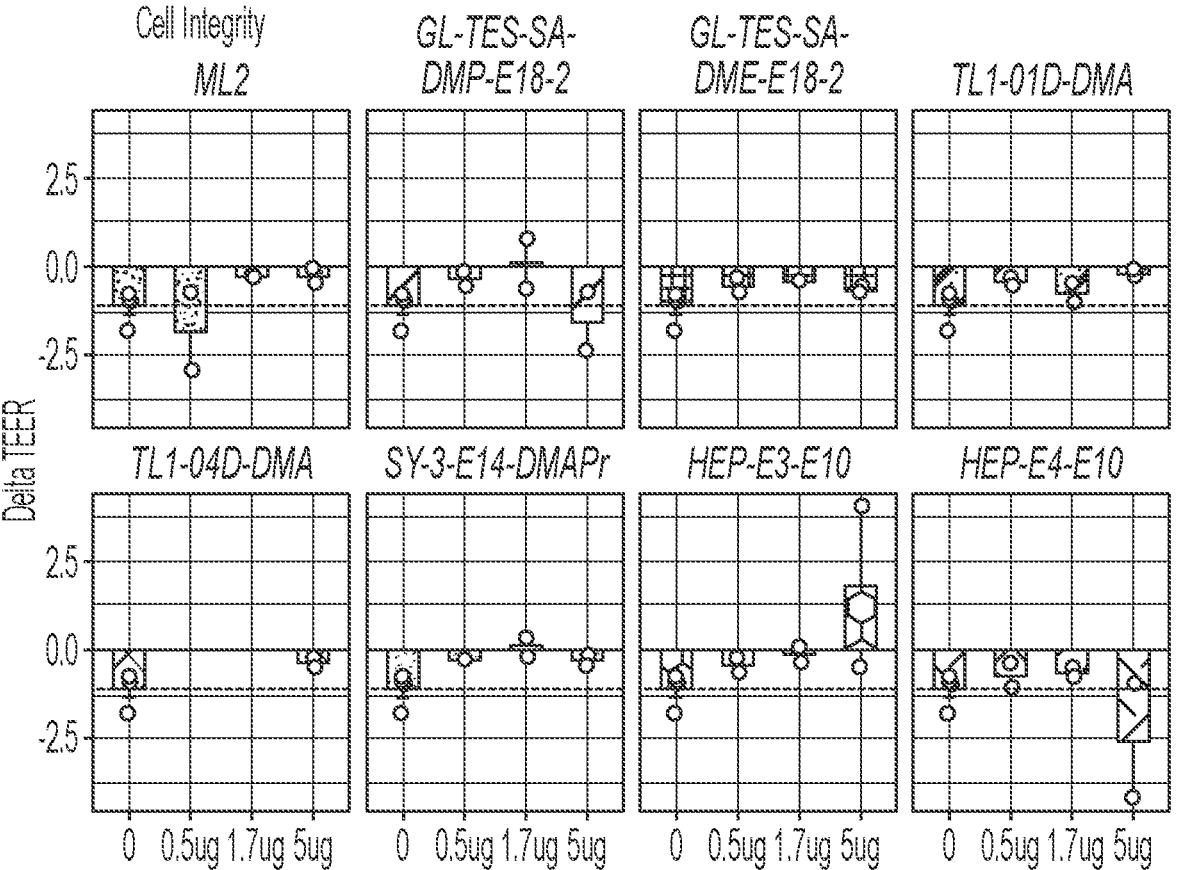
FIG. 11B is an exemplary bar graph that depicts cell integrity as measured by trans-epithelial electrical resistance (TEER), which is a strong indicator of epithelium integrity.

Cationic lipids ML2, GL-TES-SA-DMP-E18-2, GL-TES-SA-DME-E18-2, TL1-01D-DMA, TL1-04D-DMA, SY-3-E14-DMAPr, HEP-E3-E10, and HEP-E4-E10 were used to prepare LNPs encapsulating FFL mRNA. LNPs encapsulating FFL mRNA were added to apical layer of HBEC-ALI. Then, the luminescence was measured to evaluate the amount of luciferase protein expressed in the cells. As shown in FIG. 11A, all the mRNA-LNPs tested showed dose-dependent protein expression. Additionally, the mRNA-LNPs showed robust protein expression in the lung cells in the HEBC-ALI model. To examine if the human bronchial epithelial cells in the HBEC-ALI model maintain cell integrity during the experiments, trans-epithelial electrical resistance (TEER), which is a strong indicator of epithelium integrity, was measured. As shown in FIG. 11B, TEER did not significantly differ, indicating that the monolayer remained intact for most treatment with mRNA-LNPs. Therefore, the HBEC-ALI model can be used as a robust in vitro system for evaluating mRNA-LNPs for protein expression in lung cells.

Figure 12:
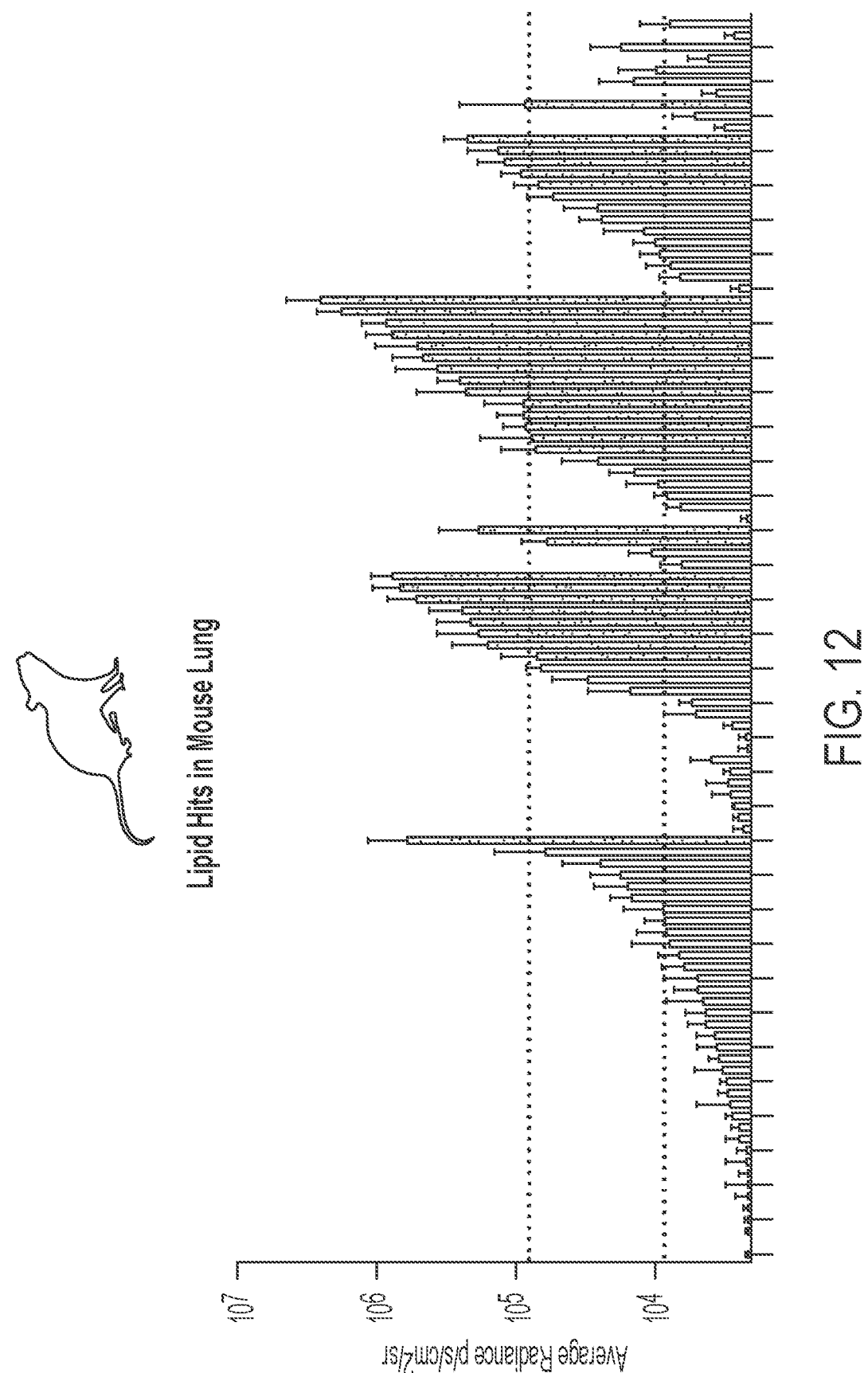
FIG. 12 is an exemplary ROC curve (receiver operating characteristic curve) demonstrating that HBEC-ALI model shows meaningful performance as classification model for screening and filtering lipids prior to in vivo evaluation.
Figure 12:
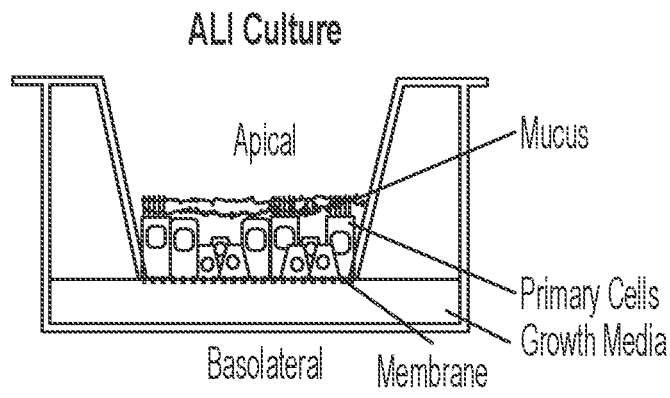
Figure 12:
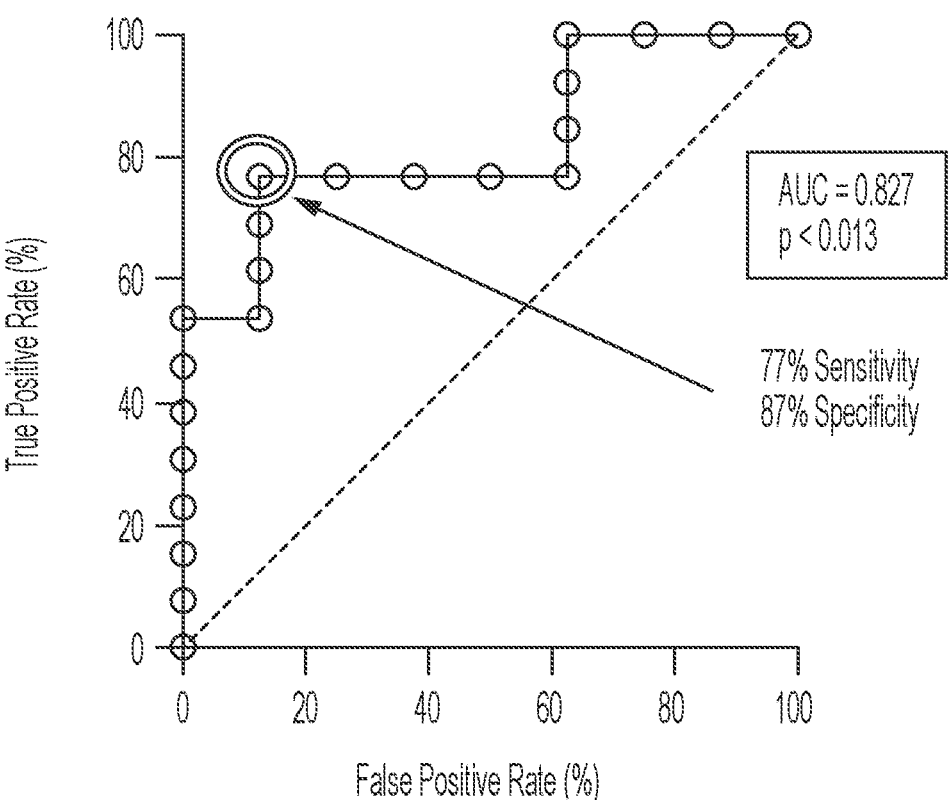

To further examine if the data from the HBEC-ALI model is a good predictor for in vivo protein expression, ROC curve (receiver operating characteristic curve) was plotted. Typically, the closer an ROC curve is to the upper left corner, the more efficient is the test. Statistics from the ROC curve show that the AUC (Area under the ROC Curve) is high (0.827) with a low p value (<0.013) (FIG. 12), indicating that data from HBEC-ALI model are translatable for determining in vivo potency of mRNA-LNPs, and that HBEC-ALI model can be used to predict mRNA-LNPs that warrant further investigation for in vivo applications.

Figures 13A, 13B:
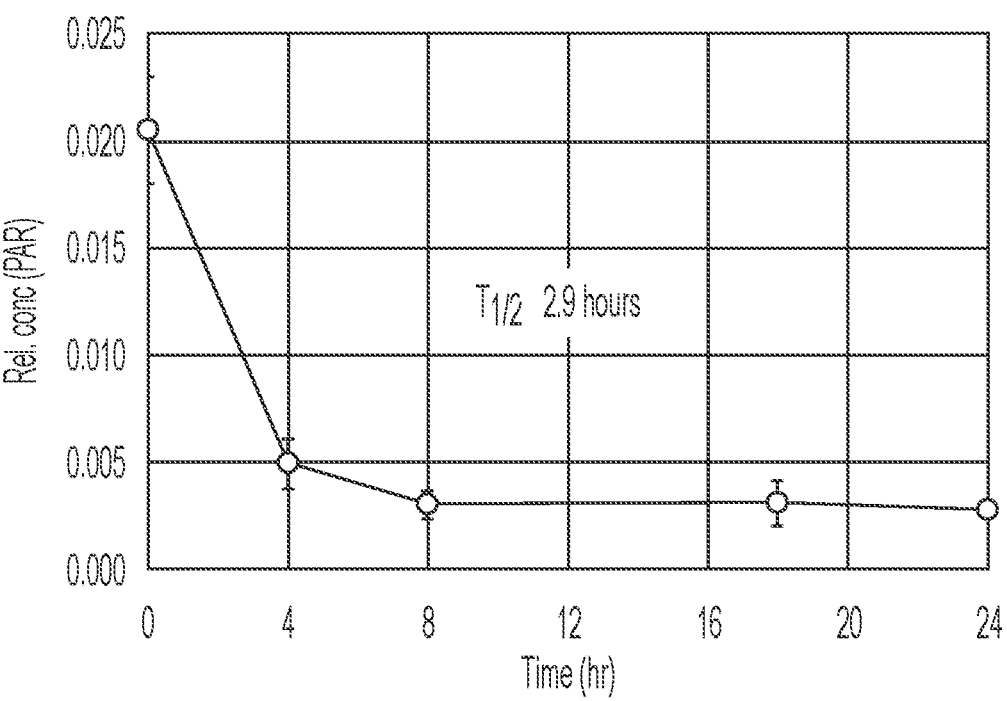
FIG. 13A is an exemplary graph that shows relative concentration of lipids in the HBEC-ALI model after transfection with mRNA-LNPs. The half-life determined from the graph is about 2.9 hours.
FIG. 13B is an exemplary table that shows half-life values determined from mouse and human lung homogenates.

Next, lipid degradation rate post HBEC-ALI transfection was determined and compared to results obtained with mouse and human lung homogenates. It is desirable if the lipids degrade rapidly to reduce potential toxicity of LNP components, including cationic lipids. Concentration of lipids was measured in the HBEC-ALI sample culture over time and plotted as shown in FIG. 13A. The results show that after transfection with mRNA-LNP, the lipids degrade rapidly over time, with a half-life of about 2.9 hours. The half-life value determined from the HBEC-ALI model was comparable to values determined from mouse and human lung homogenates, which were 4.5 and 3.6 hours, respectively, as shown in FIG. 13B. These results demonstrate that the HBEC-ALI model is a useful indicator for the performance of mRNA-LNPs in vivo.

Overall, the data in this example demonstrate that HBEC-ALI shows meaningful performance as classification model for screening and filtering lipids prior to in vivo evaluation. Furthermore, the mRNA-LNPs of the present invention have robust protein expression and rapid degradation. Combined with the in vivo data presented herein, the mRNA-LNPs of the present invention are predicted to perform exceptionally well in terms of both increased potency and improved tolerability in in vivo application involving the repeat delivery of mRNA to the lung via nebulization.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

---

We claim:

1. A codon-optimized mRNA molecule comprising a coding sequence encoding Cystic Fibrosis Transmembrane Conductance Regulator (CFTR) protein, wherein the coding sequence encodes the amino acid sequence set forth by SEQ ID NO: 1 and the coding sequence is at least 90%, at least 95%, at least 98%, at least 99%, or 100% identical to SEQ ID NO: 2 or SEQ ID NO: 3.

2. The mRNA molecule of claim 1, wherein the coding sequence is identical to any one of SEQ ID NOs: 2-11.

3. The mRNA molecule of claim 1, further comprising a 5'-UTR, and/or a 3' UTR,
   wherein the 5'-UTR comprises SEQ ID NO: 12, and
     wherein the 3'-UTR comprises SEQ ID NO: 13 or SEQ ID NO: 14.

4. A polynucleotide comprising a sequence encoding the mRNA of any one of SEQ ID NOs: 2-11.

5. The polynucleotide of claim 4, wherein the polynucleotide is a linear or circular polynucleotide comprising deoxyribonucleotide residues.

6. A pharmaceutical composition for treating cystic fibrosis, comprising a codon optimized mRNA encoding the Cystic Fibrosis Transmembrane Conductance Regulator (CFTR) protein set forth by SEQ ID NO: 1 and wherein the codon optimized CFTR mRNA comprises a polynucleotide sequence at least 90%, at least 95%, at least 98%, at least 99%, or 100% identical to SEQ ID NO: 2 or SEQ ID NO: 3.

7. The pharmaceutical composition of claim 6, wherein the codon optimized CFTR mRNA comprises any one of the sequences set forth by SEQ ID NOs: 2-11.

8. The pharmaceutical composition of claim 6, wherein the codon optimized CFTR mRNA further comprises a 5' untranslated region (UTR) sequence set forth by SEQ ID NO: 12, and wherein the codon optimized CFTR mRNA further comprises a 3' untranslated region (UTR) sequence set forth by SEQ ID NO: 13 or SEQ ID NO: 14.

9. The pharmaceutical composition of claim 6, wherein the codon optimized CFTR mRNA encoding the CFTR protein is encapsulated within a liposome.

10. The pharmaceutical composition of claim 9, wherein the liposome comprises one or more cationic lipids, one or more non-cationic lipids, and one or more PEG-modified lipids.

11. The pharmaceutical composition of claim 10, wherein the liposome further comprises one or more cholesterol-based lipids.

12. The pharmaceutical composition of claim 10, wherein the liposome consists of the one or more cationic lipids, the one or more non-cationic lipids, and the one or more PEG-modified lipids.

13. The pharmaceutical composition of claim 12, wherein the one or more cationic lipids is HGT4002, the one or more non-cationic lipids is DOPE and the one or more PEG-modified lipids is DMG-PEG2K, wherein HGT4002, DOPE and DMG-PEG2K are present in a molar ratio of approximately 60:35:5, respectively.

14. The pharmaceutical composition of claim 10, wherein the liposome comprises the one or more cationic lipid, the one or more non-cationic lipid, the one or more PEG-modified lipid, and cholesterol.

15. The pharmaceutical composition of claim 14, wherein the cationic lipid is selected from GL-TES-SA-DME-E18-2, TL1-01D-DMA, SY-3-E14-DMAPr, TL1-10D-DMA, GL-TES-SA-DMP-E18-2, HEP-E4-E10, HEP-E3-E10 and TL1-04D-DMA, wherein the non-cationic lipid is DOPE or DEPE, and wherein the PEG-modified lipid is DMG-PEG2K.

16. The pharmaceutical composition of claim 9, wherein the liposome has a size less than about 100 nm.

17. The pharmaceutical composition of claim 6 further comprising a CFTR potentiator, corrector and/or activator.

18. A method of treating cystic fibrosis comprising administering to a subject in need of treatment the pharmaceutical composition of claim 6.

19. The method of claim 18, wherein the pharmaceutical composition is administered to the subject via pulmonary delivery.

20. The method of claim 18, wherein treating the subject is achieved at a lower therapeutically effective dose in comparison to treating the subject with a non-codon optimized mRNA encoding the wild type CFTR, and/or treating the subject requires shorter times to administer the therapeutically effective dose in comparison to treating with the non-codon optimized mRNA encoding the wild type CFTR.

\* \* \* \* \*

SEQUENCE LISTING

```
<160> NUMBER OF SEQ ID NOS: 17

<210> SEQ ID NO 1
<211> LENGTH: 1480
<212> TYPE: PRT
<213> ORGANISM: Homo sapiens

<400> SEQUENCE: 1

Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Phe Leu Tyr Leu Gly Glu Val Thr Lys Ala
                85                  90                  95
```

-continued

```
Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
            115                 120                 125

Leu Leu Phe Ile Val Arg Thr Leu Leu Leu His Pro Ala Ile Phe Gly
        130                 135                 140

Leu His His Ile Gly Met Gln Met Arg Ile Ala Met Phe Ser Leu Ile
    145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
            195                 200                 205

Ala Leu Leu Met Gly Leu Ile Trp Glu Leu Leu Gln Ala Ser Ala Phe
        210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
            275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
                340                 345                 350

Gln Phe Pro Trp Ala Val Gln Thr Trp Tyr Asp Ser Leu Gly Ala Ile
            355                 360                 365

Asn Lys Ile Gln Asp Phe Leu Gln Lys Gln Glu Tyr Lys Thr Leu Glu
        370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Val Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510
```

```
Asp Glu Tyr Arg Tyr Arg Ser Val Ile Lys Ala Cys Gln Leu Glu Glu
        515                 520             525

Asp Ile Ser Lys Phe Ala Glu Lys Asp Asn Ile Val Leu Gly Glu Gly
        530                 535             540

Gly Ile Thr Leu Ser Gly Gly Gln Arg Ala Arg Ile Ser Leu Ala Arg
545                 550             555                 560

Ala Val Tyr Lys Asp Ala Asp Leu Tyr Leu Leu Asp Ser Pro Phe Gly
                565             570             575

Tyr Leu Asp Val Leu Thr Glu Lys Glu Ile Phe Glu Ser Cys Val Cys
            580             585             590

Lys Leu Met Ala Asn Lys Thr Arg Ile Leu Val Thr Ser Lys Met Glu
            595             600             605

His Leu Lys Lys Ala Asp Lys Ile Leu Ile Leu His Glu Gly Ser Ser
        610             615             620

Tyr Phe Tyr Gly Thr Phe Ser Glu Leu Gln Asn Leu Gln Pro Asp Phe
625             630             635             640

Ser Ser Lys Leu Met Gly Cys Asp Ser Phe Asp Gln Phe Ser Ala Glu
            645             650             655

Arg Arg Asn Ser Ile Leu Thr Glu Thr Leu His Arg Phe Ser Leu Glu
            660             665             670

Gly Asp Ala Pro Val Ser Trp Thr Glu Thr Lys Lys Gln Ser Phe Lys
            675             680             685

Gln Thr Gly Glu Phe Gly Glu Lys Arg Lys Asn Ser Ile Leu Asn Pro
        690             695             700

Ile Asn Ser Ile Arg Lys Phe Ser Ile Val Gln Lys Thr Pro Leu Gln
705             710             715             720

Met Asn Gly Ile Glu Glu Asp Ser Asp Glu Pro Leu Glu Arg Arg Leu
            725             730             735

Ser Leu Val Pro Asp Ser Glu Gln Gly Glu Ala Ile Leu Pro Arg Ile
            740             745             750

Ser Val Ile Ser Thr Gly Pro Thr Leu Gln Ala Arg Arg Arg Gln Ser
            755             760             765

Val Leu Asn Leu Met Thr His Ser Val Asn Gln Gly Gln Asn Ile His
        770             775             780

Arg Lys Thr Thr Ala Ser Thr Arg Lys Val Ser Leu Ala Pro Gln Ala
785             790             795             800

Asn Leu Thr Glu Leu Asp Ile Tyr Ser Arg Arg Leu Ser Gln Glu Thr
            805             810             815

Gly Leu Glu Ile Ser Glu Glu Ile Asn Glu Glu Asp Leu Lys Glu Cys
            820             825             830

Phe Phe Asp Asp Met Glu Ser Ile Pro Ala Val Thr Thr Trp Asn Thr
        835             840             845

Tyr Leu Arg Tyr Ile Thr Val His Lys Ser Leu Ile Phe Val Leu Ile
        850             855             860

Trp Cys Leu Val Ile Phe Leu Ala Glu Val Ala Ala Ser Leu Val Val
865             870             875             880

Leu Trp Leu Leu Gly Asn Thr Pro Leu Gln Asp Lys Gly Asn Ser Thr
            885             890             895

His Ser Arg Asn Asn Ser Tyr Ala Val Ile Ile Thr Ser Thr Ser Ser
            900             905             910

Tyr Tyr Val Phe Tyr Ile Tyr Val Gly Val Ala Asp Thr Leu Leu Ala
            915             920             925

Met Gly Phe Phe Arg Gly Leu Pro Leu Val His Thr Leu Ile Thr Val
```

-continued

```
          930              935              940
Ser Lys Ile Leu His His Lys Met Leu His Ser Val Leu Gln Ala Pro
945              950              955              960

Met Ser Thr Leu Asn Thr Leu Lys Ala Gly Gly Ile Leu Asn Arg Phe
              965              970              975

Ser Lys Asp Ile Ala Ile Leu Asp Asp Leu Leu Pro Leu Thr Ile Phe
              980              985              990

Asp Phe Ile Gln Leu Leu Leu Ile  Val Ile Gly Ala Ile  Ala Val Val
              995              1000              1005

Ala Val  Leu Gln Pro Tyr Ile  Phe Val Ala Thr Val  Pro Val Ile
     1010              1015              1020

Val Ala  Phe Ile Met Leu Arg  Ala Tyr Phe Leu Gln  Thr Ser Gln
     1025              1030              1035

Gln Leu  Lys Gln Leu Glu Ser  Glu Gly Arg Ser Pro  Ile Phe Thr
     1040              1045              1050

His Leu  Val Thr Ser Leu Lys  Gly Leu Trp Thr Leu  Arg Ala Phe
     1055              1060              1065

Gly Arg  Gln Pro Tyr Phe Glu  Thr Leu Phe His Lys  Ala Leu Asn
     1070              1075              1080

Leu His  Thr Ala Asn Trp Phe  Leu Tyr Leu Ser Thr  Leu Arg Trp
     1085              1090              1095

Phe Gln  Met Arg Ile Glu Met  Ile Phe Val Ile Phe  Phe Ile Ala
     1100              1105              1110

Val Thr  Phe Ile Ser Ile Leu  Thr Thr Gly Glu Gly  Glu Gly Arg
     1115              1120              1125

Val Gly  Ile Ile Leu Thr Leu  Ala Met Asn Ile Met  Ser Thr Leu
     1130              1135              1140

Gln Trp  Ala Val Asn Ser Ser  Ile Asp Val Asp Ser  Leu Met Arg
     1145              1150              1155

Ser Val  Ser Arg Val Phe Lys  Phe Ile Asp Met Pro  Thr Glu Gly
     1160              1165              1170

Lys Pro  Thr Lys Ser Thr Lys  Pro Tyr Lys Asn Gly  Gln Leu Ser
     1175              1180              1185

Lys Val  Met Ile Ile Glu Asn  Ser His Val Lys Lys  Asp Asp Ile
     1190              1195              1200

Trp Pro  Ser Gly Gly Gln Met  Thr Val Lys Asp Leu  Thr Ala Lys
     1205              1210              1215

Tyr Thr  Glu Gly Gly Asn Ala  Ile Leu Glu Asn Ile  Ser Phe Ser
     1220              1225              1230

Ile Ser  Pro Gly Gln Arg Val  Gly Leu Leu Gly Arg  Thr Gly Ser
     1235              1240              1245

Gly Lys  Ser Thr Leu Leu Ser  Ala Phe Leu Arg Leu  Leu Asn Thr
     1250              1255              1260

Glu Gly  Glu Ile Gln Ile Asp  Gly Val Ser Trp Asp  Ser Ile Thr
     1265              1270              1275

Leu Gln  Gln Trp Arg Lys Ala  Phe Gly Val Ile Pro  Gln Lys Val
     1280              1285              1290

Phe Ile  Phe Ser Gly Thr Phe  Arg Lys Asn Leu Asp  Pro Tyr Glu
     1295              1300              1305

Gln Trp  Ser Asp Gln Glu Ile  Trp Lys Val Ala Asp  Glu Val Gly
     1310              1315              1320

Leu Arg  Ser Val Ile Glu Gln  Phe Pro Gly Lys Leu  Asp Phe Val
     1325              1330              1335
```

```
Leu Val  Asp Gly Gly Cys Val  Leu Ser His Gly His  Lys Gln Leu
    1340                1345               1350

Met Cys  Leu Ala Arg Ser Val  Leu Ser Lys Ala Lys  Ile Leu Leu
    1355                1360               1365

Leu Asp  Glu Pro Ser Ala His  Leu Asp Pro Val Thr  Tyr Gln Ile
    1370                1375               1380

Ile Arg  Arg Thr Leu Lys Gln  Ala Phe Ala Asp Cys  Thr Val Ile
    1385                1390               1395

Leu Cys  Glu His Arg Ile Glu  Ala Met Leu Glu Cys  Gln Gln Phe
    1400                1405               1410

Leu Val  Ile Glu Glu Asn Lys  Val Arg Gln Tyr Asp  Ser Ile Gln
    1415                1420               1425

Lys Leu  Leu Asn Glu Arg Ser  Leu Phe Arg Gln Ala  Ile Ser Pro
    1430                1435               1440

Ser Asp  Arg Val Lys Leu Phe  Pro His Arg Asn Ser  Ser Lys Cys
    1445                1450               1455

Lys Ser  Lys Pro Gln Ile Ala  Ala Leu Lys Glu Glu  Thr Glu Glu
    1460                1465               1470

Glu Val  Gln Asp Thr Arg Leu
    1475                1480

<210> SEQ ID NO 2
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 2
atgcagcgtt ctcccctgga gaaggcttct gtggtgagta aacttttttt ctcctggacc      60
agacctatcc tgaggaaagg ctacaggcag agactggagc tctctgacat ataccagata     120
ccttcagtcg atagcgccga caacctgagc gagaagctgg aacgcgagtg ggacagagag     180
ctggcaagca agaagaaccc aaaagctgatt aatgccctga aaggtgtttt cttctggaga     240
ttcatgttct acggaatctt tctgtatctg ggggaggtta caaaggctgt gcaaccctg     300 ctgctcggca gaatcatcgc ctcatacgat ccagacaaca aggaagaaag aagcatcgcc     360
atctacctgg gcattggcct ctgcctcctg tttattgtgc ggactctgct gctgcaccca     420
gcaattttcg ggttgcatca tattggcatg cagatgcgca ttgctatgtt ttccctcatc     480
tacaaaaaga cactgaaact cagctcccgg gtgctggaca agatctccat cggccaactg     540
gtgtctctcc tgagcaataa cttgaataag ttcgacgaag ggctggccct ggcacacttc     600
gtgtggattg cccccctgca ggtggccctg ctgatgggac tgatttggga actgctgcag     660
gctagcgctt tctgcggcct gggggttcctg atcgtgctgg cactgtttca ggcaggcctg     720
ggccgtatga tgatgaagta cagagaccag agggccggga agatctccga acggctcgtt     780
attacctctg agatgatcga gaacattcag tctgtgaaag cctactgctg ggaggaggct     840
atggagaaga tgatcgagaa tctgagacag accgagctga gctgaccag aaaggccgcc     900 tacgtgaggt acttcaacag cagtgccttc ttcttctctg ggttcttcgt tgtgtttctg     960
agcgtgctgc atacgctct catcaaaggc atcatcctgc ggaagatctt caccaccatc    1020
agcttttgca tcgtgcttag aatggccgtg acacggcagt tcccatgggc cgttcaaact    1080
tggtatgatt ccctgggcgc catcaacaaa atccaggatt tcctgcagaa gcaggaatac    1140
```

-continued

```
aagacactcg aatataacct cacaactact gaggtggtta tggagaacgt gactgccttc     1200
tgggaggagg ggttcggaga gcttttgag aaggccaaac agaataataa taaccgcaaa      1260
accagcaacg gcgacgacag cctgttcttc tccaattttt ctctcctggg aacacccgtc     1320
ctcaaagaca tcaactttaa gatcgagagg ggccagctgc tcgccgtcgc cggatccaca      1380
ggcgccggca agacctctct gctgatggtt atcatgggcg aactggagcc ctccgagggc     1440
aagattaagc actcaggaag aatctccttt tgtagccagt tcagttggat tatgcccggc      1500
actattaagg agaatatcat ttttggggtg agctatgatg agtatcggta tcggagcgtt     1560
atcaaagcct gtcagctgga ggaggatatc agcaagttcg cagagaagga taatattgtg      1620
ctgggagagg gaggaatcac cctgagcgga ggccagagag ccagaatctc actggcccgg     1680
gccgtctaca aggacgccga cctttacctt ctggacagtc cctttggata tctggatgtg      1740
ctgactgaaa aggagatctt cgagtcttgt gtgtgcaagc tgatggctaa caagacccgg     1800
atcctagtga ctagtaagat ggagcacctg aagaaggcag acaagatctt gattctgcac      1860
gagggatcct cttactttta cggcaccttt agcgagctgc agaacctcca gcccgatttc     1920
tcatctaagc tgatgggctg tgatagcttc gaccagttct ctgccgagcg cagaaacagc      1980
atcctgacag agacactgca ccggtttttca ctggagggcg acgcccctgt cagctggacc     2040
gagaccaaaa agcagtcttt caagcagaca ggcgagttcg gcgagaagcg caaaaacagc      2100
atcctgaatc caatcaactc tataaggaag tttagcatcg tgcagaagac acccctccag      2160
atgaacggca tcgaagagga cagtgacgag cccctggagc ggcgcctgag cctcgtgcct     2220
gacagcgaac agggcgaggc catcctgcct aggatcagcg tgatttcaac cgggccaaca      2280
ctgcaggcta ggagaagaca gtcagtgctt aacctgatga cacatagcgt gaatcaggga     2340
cagaacatcc atcgaaaaac cacagcctct actcgcaaag tgtcactggc tcctcaggct      2400
aatctgacag agctggacat ctatagcagg aggctgagcc aggagacagg cctggagatc     2460
agtgaggaga tcaacgaaga ggacctgaag gagtgctttt tcgatgacat ggagagtatc      2520
cccgccgtca ccacctggaa tacctacctc cggtacatca cagtgcacaa gtccctcatc     2580
tttgtgctga tttggtgcct cgtgatcttt ctcgcagaag tggccgcctc cctggtggtg     2640
ctgtggctgt tggggaatac tccactgcag gacaaaggca attctacaca cagcaggaat      2700
aattcctatg ccgtgattat caccagcaca tcctcttact acgtgttcta catctacgtg     2760
ggagtggcag atactctgct tgcaatgggc ttcttcaggg ggctgcccct ggtgcacaca      2820
ctgatcacag tgtccaagat cctccaccat aaaaatgctcc acagcgtgct gcaggcaccc     2880
atgagcaccc tgaacacact gaaggccggc ggcatcctga atcgcttttc caaagacatc      2940
gccatcctcg acgatctcct gccactgacc atcttcgatt ttatccagct gctgctgatc      3000
gtgatcgggg ccatcgccgt ggtggccgtg ctgcagccat acatttttcgt ggctacagtg     3060 cccgtgatcg ttgcctttat catgctgaga gcctacttcc tgcagacttc tcagcagctg      3120
aagcagctgg agagcgaagg gagaagcccc atcttcactc acctggtgac aagcctgaag     3180
ggactctgga ccctgagagc cttcggccgg cagccctatt cgagaccct gtttcacaag        3240 gccctcaacc tgcacacagc caactggttc ctctacctgt ccaccctgag gtggttccag     3300
atgaggattg aaatgatctt cgtgattttt ttcatcgccg tgacattcat tagcattctg      3360
accaccggcg aggggagggg gagagtgggc atcatcctga cccttgccat gaacattatg     3420
agcacactgc agtgggccgt gaatagtagt atcgacgtgg acagtctgat gaggtccgtg     3480
agccgggtgt tcaagttcat tgacatgccc acagaaggga aacccaccaa aagcaccaag      3540
```

-continued

```
ccctacaaga acgggcagct gtccaaggtt atgatcatcg agaactctca cgtgaagaag      3600
gacgacattt ggcccagcgg cggccagatg acagtgaaag atctgaccgc caaatacacc      3660
gagggaggca acgccatcct cgaaaacatt agcttctcta tcagccctgg acagagggtg      3720
ggcctgctgg gccggacagg ctcagggaag agtactctgc tgtcagcatt cctgaggctc      3780
ctgaacacag agggcgagat ccagattgac ggcgtgtcct gggactccat caccctgcag      3840
cagtggcgga aggctttcgg ggtgatcccc cagaaggtgt tcatctttag cggcacttttc     3900 agaaagaatc tggacccttta tgagcagtgg agtgaccagg agatctggaa agtggccgat      3960
gaggtcggac tgaggagcgt gatcgagcag tttccaggga agctggactt tgtgctggtg      4020
gatggcggat gcgtgctgtc tcacggccat aaacagctga tgtgtctggc ccggtccgtg      4080
ctgtctaagg ccaagatcct gctgctggac gaaccctccg cccacctgga ccccgtgaca      4140
taccagatca tcaggagaac tctcaagcag gccttcgccg actgtaccgt gattctgtgc      4200
gagcaccgca ttgaagctat gctggagtgt cagcagttcc tggtgatcga ggaaaataag      4260
gtgaggcagt acgacagcat ccagaagctg ctgaacgagc gctccctgtt ccgccaggct      4320
atctccccat cagaccgggt gaagctcttc ccccacagaa actcctcaaa gtgcaagtcc      4380
aagccccaga tcgccgccct gaaggaggag accgaggagg aggtgcagga caccaggctg      4440
tga                                                                    4443
```

```
<210> SEQ ID NO 3
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 3
```

```
atgcagcgct cgcctctgga aaaggcgagc gtcgtgtcaa agctattctt ttcttggacc       60
cggcccattc tcaggaaggg ctacaggcag aggctggagt tgagcgacat ctatcagatt      120
ccttccgtgg acagcgccga caacctgagc gagaagctgg aaagggagtg ggaccgcgaa      180
ctggcaagca aaaagaaccc caagctgatc aatgccctga aaggtgtttt cttttggaga      240
ttcatgttct acgggatctt tctgtatctg ggcgaggtta caaaggctgt gcagccctg       300 ctgctcggca gaatcatcgc ctcatacgat ccagacaaca aggaagaaag aagcatcgcc      360
atctacctgg gcattggcct ctgcctcctg tttattgtgc ggactctgct gctgcaccca      420
gcaattttcg ggttgcatca tattggcatg cagatgcgca ttgctatgtt ttccctcatc      480
tacaaaaaga cactgaaact cagctcccgg gtgctggaca agatctccat cggccaactg      540
gtgtctctcc tgagcaataa cttgaataag ttcgacgaag ggctggccct ggcacacttc      600
gtgtggattg ccccccctgca ggtggccctg ctgatgggac tgatttggga actgctgcag      660
gctagcgctt tctgcggcct ggggttcctg atcgtgctgg cactgtttca ggcaggcctg      720
ggccgtatga tgatgaagta cagagaccag agggccggga agatctccga acggctcgtt      780
attacctctg agatgatcga gaacattcag tctgtgaaag cctactgctg ggaggaggct      840
atggagaaga tgatcgagaa tctgagacag accgagctga agctgaccag aaaggccgcc      900
tacgtgaggt acttcaacag cagtgccttc ttcttctctg cttcttcgt tgtgtttctg        960 agcgtgctgc catacgctct catcaaaggc atcatcctgc ggaagatctt caccaccatc       1020
agcttttgca tcgtgcttag aatggccgtg acccggcagt tcccatgggc cgtgcaaact      1080
```

-continued

```
tggtatgatt ccctgggcgc catcaacaaa atccaggatt tcctgcagaa gcaggaatac   1140
aagacactcg aatataatct cacaactact gaggtggtta tggagaacgt gactgccttc   1200
tgggaggagg ggttcggaga gcttttttgag aaggcaaaac agaataacaa caaccgcaaa   1260
accagcaacg gcgacgacag cctgttcttc tccaattttt ctctcctggg aacacccgtc   1320
ctcaaagaca tcaactttaa gatcgagagg ggacagctgc tcgcagtcgc cggatccaca   1380
ggcgccggca agacctctct gctgatggtt atcatgggcg aactggagcc atccgagggc   1440
aagattaagc acagtggaag aatctccttt tgtagccagt tcagttggat tatgcccggc   1500
actattaagg agaatatcat ttttgggggtg agctatgatg agtatcggta tcggagcgtt   1560
atcaaagcct gtcagctgga ggaggatatc agcaaattcg cagagaagga taatatcgtg   1620 ctggggagg ggggaatcac cctgagcgga ggccagagag ccagaatctc actggcccgg   1680
gccgtctaca aggacgccga cctttacctt ctggacagtc cctttggata tctggatgtg   1740
ctgactgaaa aggagatctt cgagtcttgt gtgtgcaagc tgatggctaa taagacccgg   1800
atcctagtga ccagtaagat ggagcacctg aagaaggcag acaagatctt gattctgcac   1860
gagggatcct cttactttta cggcacctttt agcgagctgc agaatctcca gcccgatttc   1920
tcatctaagc tgatgggctg tgatagcttc gaccagttct ctgccgagcg cagaaacagc   1980
atcctgacag agacactgca ccggtttttca ctggagggcg acgccctgt cagctggacc   2040 gagaccaaaa agcagtcttt caagcagaca ggcgagttcg gcgagaagcg caaaaacagc   2100
atcctgaatc caatcaactc tataaggaag tttagcatcg tgcagaagac accctccag   2160 atgaacggca tcgaagagga cagtgacgag cccctggagc ggcgcctgag cctcgtgcct   2220
gacagcgaac agggcgaggc catcctgcct aggatcagcg tgatttcaac cgggccaaca   2280
ctgcaggcta ggagaagaca gtcagtgctt aacctgatga cacatagcgt gaatcaggga   2340
cagaacatcc atcgaaaaac cacagcctct actcgcaaag tgtcactggc tcctcaggct   2400
aatctgacag agctggacat ctatagcagg aggctgagcc aggagacagg cctggagatc   2460
agtgaggaga tcaacgaaga ggacctgaag gagtgctttt tcgatgacat ggagagtatc   2520
cccgccgtca ccacctggaa tacctacctc cggtacatca cagtgcacaa gtccctcatc   2580
tttgtgctga tttggtgcct cgtgatcttt ctcgcagaag tggccgcctc cctggtggtg   2640
ctgtggctgt tggggaatac tccactgcag gacaaaggca attctacaca cagcaggaat   2700
aattcctatg ccgtgattat caccagcaca tcctcttact acgtgttcta catctacgtg   2760
ggagtggcag atactctgct tgcaatgggc ttcttcaggg ggctgccct ggtgcacaca   2820 ctgatcacag tgtccaagat cctccaccat aaaatgctcc acagcgtgct gcaggcaccc   2880
atgagcaccc tgaacacact gaaggccggc ggcatcctga atcgcttttc caaagacatc   2940
gccatcctcg acgatctcct gccactgacc atcttcgatt ttatccagct gctgctgatc   3000
gtgatcgggg ccatcgccgt ggtggccgtg ctgcagccat acatttttcgt ggctacagtg   3060 cccgtgatcg ttgcctttat catgctgaga gcctacttcc tgcagacttc tcagcagctg   3120
aagcagctgg agagcgaagg gagaagcccc atcttcactc acctggtgac aagcctgaag   3180
ggactctgga ccctgagagc cttcggccgg cagcccatt tcgagacct gtttcacaag   3240 gccctcaacc tgcacacagc caactggttt ctctacctgt ccaccctgag gtggttccag   3300
atgaggattg aaatgatctt cgtgattttt ttcatcgccg tgacattcat tagcattctg   3360
accaccggcg aggggagggg gagagtgggc atcatcctga cccttgccat gaacattatg   3420
tccacactgc agtgggccgt gaatagttca atcgacgtgg acagtctgat gaggtccgtg   3480
```

-continued

```
agccgggtgt tcaagttcat tgacatgccc acagagggga aacccaccaa aagcaccaag    3540
ccctacaaga acgggcagct gtccaaggtt atgatcatcg agaactctca cgtgaagaag    3600
gacgacattt ggcccagcgg cggccagatg acagtgaaag atctgaccgc caaatacacc    3660
gagggaggca acgccatcct cgaaaacatt agcttctcta tcagccctgg acagagggtg    3720
ggcctgctgg gccggacagg ctcagggaag agtactctgc tgtcagcatt cctgaggctc    3780
ctgaacacag agggcgagat ccagattgac ggcgtgtcct gggactccat caccctgcag    3840
cagtggcgga aggctttcgg ggtgatcccc cagaaggtgt tcatctttag cggcactttc    3900
agaaagaatc tggacccctta tgagcagtgg agtgaccagg agatctggaa agtggccgat    3960
gaggtcggac tgaggagcgt gatcgagcag tttccaggga agctggactt tgtgctggtg    4020
gatggcggat gcgtgctgtc tcacggccat aaacagctga tgtgtctggc ccggtccgtg    4080
ctgtctaagg ccaagatcct gctgctggac gaaccctccg cccacctgga ccccgtgaca    4140
taccagatca tcaggagaac tctcaagcag gccttcgccg actgtaccgt gattctgtgc    4200
gagcaccgca ttgaagctat gctggagtgt cagcagttcc tggtgatcga ggaaaataag    4260
gtgaggcagt acgacagcat ccagaagctg ctgaacgagc gctccctgtt ccgccaggct    4320
atctccccat cagaccgggt gaagctcttc ccccacagaa actcctcaaa gtgcaagtcc    4380
aagccccaga tcgccgccct gaaggaggag accgaggagg aggtgcagga caccaggctg    4440
tga                                                                   4443
```

```
<210> SEQ ID NO 4
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 4
```

```
atgcagcgtt ctcccctgga gaaggcttct gtggtgagta aacttttttt ctcctggacc      60
agacctatcc tgaggaaagg ctacaggcag agactggagc tctctgacat ataccagata     120
ccttcagtcg atagcgccga caacctgagc gagaagctgg aacgcgagtg ggacagagag     180
ctggcaagca agaagaaccc aaagctgatt aatgccctga aaggtgtttt cttctggaga     240
ttcatgttct acggaatctt tctgtatctg ggggaggtta caaaggctgt gcaacccctg     300
ctgctcggca gaatcatcgc ctcatacgat ccagacaaca aggaagaaag aagcatcgcc     360
atctacctgg gcattggcct ctgcctcctg tttattgtgc ggactctgct gctgcaccca     420
gcaattttcg ggttgcatca tattggcatg cagatgcgca ttgctatgtt ttccctcatc     480
tacaaaaaga cactgaaact cagctcccgg gtgctggaca agatctccat cggccaactg     540
gtgtctctcc tgagcaataa cttgaataag ttcgacgaag ggctggccct ggcacacttc     600
gtgtggattg ccccctgca ggtggccctg ctgatgggac tgatttggga actgctgcag     660
gctagcgctt tctgcggcct ggggttcctg atcgtgctgg cactgtttca ggcaggcctg     720
ggccgtatga tgatgaagta cagagaccag aggcccggga gatctccga acggctcgtt     780 attacctctg agatgatcga gaacattcag tctgtgaaag cctactgctg ggaggaggct     840
atggagaaga tgatcgagaa tctgagacag accgagctga gctgaccag aaaggccgcc     900 tacgtgaggt acttcaacag cagtgccttc ttcttctctg ggttcttcgt tgtgtttctg     960
agcgtgctgc catacgctct catcaaaggc atcatcctgc ggaagatctt caccaccatc    1020
```

```
agcttttgca tcgtgcttag aatggccgtg accoggcagt tcccatgggc cgtgcaaact   1080
tggtatgatt ccctgggcgc catcaacaaa atccaggatt tcctgcagaa gcaggaatac   1140
aagacactcg aatataatct cacaactact gaggtggtta tggagaacgt gactgccttc   1200
tgggaggagg ggttcggaga gcttttttgag aaggcaaaac agaataacaa caaccgcaaa   1260
accagcaacg gcgacgacag cctgttcttc tccattttt ctctcctggg aacacccgtc   1320
ctcaaagaca tcaactttaa gatcgagagg ggccagctgc tcgccgtcgc cggatccaca   1380
ggcgccggca agacctctct gctgatggtt atcatgggcg aactggagcc ctccgagggc   1440
aagattaagc actcaggaag aatctccttt tgtagccagt tcagttggat tatgcccggc   1500
actattaagg agaatatcat ttttgggtg agctatgatg agtatcggta cggagcgtt   1560 atcaaagcct gtcagctgga ggaggatatc agcaagttcg cagagaagga taatattgtg   1620
ctgggagagg gaggaatcac cctgagcgga ggccagagag ccagaatctc actggcccgg   1680
gccgtctaca aggacgccga cctttacctt ctggacagtc cctttggata tctggatgtg   1740
ctgactgaaa aggagatctt cgagtcttgt gtgtgcaagc tgatggctaa taagacccgg   1800
atcctagtga ccagtaagat ggagcacctg aagaaggcag acaagatctt gattctgcac   1860
gagggatcct cttacttta cggcaccttt agcgagctgc agaatctcca gcccgatttc   1920
tcatctaagc tgatgggctg tgatagcttc gaccagttct ctgccgagcg cagaaacagc   1980
atcctgacag agacactgca ccggtttttca ctggagggcg acgcccctgt cagctggacc   2040
gagaccaaaa agcagtcttt caagcagaca ggcgagttcg gcgagaagcg caaaaacagc   2100
atcctgaatc caatcaactc tataaggaag tttagcatcg tgcagaagac acccctccag   2160
atgaacggca tcgaagagga cagtgacgag ccctggagc ggcgcctgag cctcgtgcct   2220
gacagcgaac agggcgaggc catcctgcct aggatcagcg tgatttcaac cgggccaaca   2280
ctgcaggcta ggagaagaca gtcagtgctt aacctgatga cacatagcgt gaatcaggga   2340
cagaacatcc atcgaaaaac cacagcctct actcgcaaag tgtcactggc tcctcaggct   2400
aatctgacag agctggacat ctatagcagg aggctgagcc aggagacagg cctggagatc   2460
agtgaggaga tcaacgaaga ggacctgaag gagtgctttt tcgatgacat ggagagtatc   2520
cccgccgtca ccacctggaa tacctacctc cggtacatca cagtgcacaa gtccctcatc   2580
tttgtgctga tttggtgcct cgtgatcttt ctcgcagaag tggccgcctc cctggtggtg   2640
ctgtggctgt tggggaatac tccactgcag gacaaaggca attctacaca cagcaggaat   2700
aattcctatg ccgtgattat caccagcaca tcctcttact acgtgttcta catctacgtg   2760
ggagtggcag atactctgct tgcaatgggc ttcttcaggg ggctgcccct ggtgcacaca   2820
ctgatcacag tgtccaagat cctccaccat aaaatgctcc acagcgtgct gcaggcaccc   2880
atgagcaccc tgaacacact gaaggccggc ggcatcctga atcgcttttc caaagacatc   2940
gccatcctcg acgatctcct gccactgacc atcttcgatt ttatccagct gctgctgatc   3000
gtgatcgggg ccatcgccgt ggtggccgtg ctgcagccat acattttcgt ggctacagtg   3060
cccgtgatcg ttgcctttat catgctgaga gcctacttcc tgcagacttc tcagcagctg   3120
aagcagctgg agagcgaagg gagaagcccc atcttcactc acctggtgac aagcctgaag   3180
ggactctgga ccctgagagc cttcggccgg cagccctatt cgagaccct gtttcacaag   3240 gccctcaacc tgcacacagc caactggttt ctctacctgt ccaccctgag gtggttccag   3300
atgaggattg aaatgatctt cgtgattttt ttcatcgccg tgacattcat tagcattctg   3360
accaccggcg aggggagg gagagtgggc atcatcctga cccttgccat gaacattatg   3420
```

-continued

```
agcacactgc agtgggccgt gaatagtagt atcgacgtgg acagtctgat gaggtccgtg      3480
agccgggtgt tcaagttcat tgacatgccc acagaaggga aacccaccaa aagcaccaag      3540
ccctacaaga acgggcagct gtccaaggtt atgatcatcg agaactctca cgtgaagaag      3600
gacgacattt ggcccagcgg cggccagatg acagtgaaag atctgaccgc caaatacacc      3660
gagggaggca acgccatcct cgaaaacatt agcttctcta tcagccctgg acagagggtg      3720
ggcctgctgg gccggacagg ctcagggaag agtactctgc tgtcagcatt cctgaggctc      3780
ctgaacacag agggcgagat ccagattgac ggcgtgtcct gggactccat caccctgcag      3840
cagtggcgga aggctttcgg ggtgatcccc cagaaggtgt tcatctttag cggcactttc      3900
agaaagaatc tggaccctta tgagcagtgg agtgaccagg agatctggaa agtggccgat      3960
gaggtcggac tgaggagcgt gatcgagcag tttccaggga agctggactt tgtgctggtg      4020
gatggcggat gcgtgctgtc tcacggccat aaacagctga tgtgtctggc ccggtccgtg      4080
ctgtctaagg ccaagatcct gctgctggac gaaccctccg cccacctgga ccccgtgaca      4140
taccagatca tcaggagaac tctcaagcag gccttcgccg actgtaccgt gattctgtgc      4200
gagcaccgca ttgaagctat gctggagtgt cagcagttcc tggtgatcga ggaaaataag      4260
gtgaggcagt acgacagcat ccagaagctg ctgaacgagc gctccctgtt ccgccaggct      4320
atctccccat cagaccgggt gaaactcttc ccccacagaa actcctcaaa gtgcaagtcc      4380
aagccccaga tcgccgccct gaaggaggag accgaggagg aggtgcagga caccaggctg      4440
tga                                                                   4443
```

```
<210> SEQ ID NO 5
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 5
```

```
atgcagcgct cgcctctgga aaaggcgagc gtcgtgtcaa agctattctt ttcttggacc        60
cggcccattc tcaggaaggg ctacaggcag aggctggagt tgagcgacat ctatcagatt       120
ccttccgtgg acagcgccga caacctgagc gagaagctgg aaagggagtg ggaccgcgaa       180
ctggcaagca aaaagaaccc caagctgatc aatgccctga aaggtgtttt cttttggaga       240
ttcatgttct acgggatctt tctgtatctg ggcgaggtta caaaggctgt gcagccctg       300 ctgctcggca gaatcatcgc ctcatacgat ccagacaaca aggaagaaag aagcatcgcc       360
atctacctgg gcattggcct ctgcctcctg tttattgtgc ggactctgct gctgcaccca       420
gcaattttcg ggttgcatca tattggcatg cagatgcgca ttgctatgtt ttccctcatc       480
tacaaaaaga cactgaaact cagctcccgg gtgctggaca agatctccat cggccaactg       540
gtgtctctcc tgagcaataa cttgaataag ttcgacgaag ggctggccct ggcacacttc       600
gtgtggattg ccccctgca ggtggccctg ctgatgggac tgatttggga actgctgcag       660
gctagcgctt tctgcggcct ggggttcctg atcgtgctgg cactgtttca ggcaggcctg       720
ggccgtatga tgatgaagta cagagaccag agggccggga gatctccga acggctcgtt       780 attacctctg agatgatcga gaacattcag tctgtgaaag cctactgctg ggaggaggct       840
atggagaaga tgatcgagaa tctgagacag accgagctga agctgaccag aaaggccgcc       900
tacgtgaggt acttcaacag cagtgccttc ttcttctctg gcttcttcgt tgtgtttctg       960
```

-continued

```
agcgtgctgc catacgctct catcaaaggc atcatcctgc ggaagatctt caccaccatc   1020
agcttttgca tcgtgcttag aatggccgtg acacggcagt tcccatgggc cgttcaaact   1080
tggtatgatt ccctgggcgc catcaacaaa atccaggatt tcctgcagaa gcaggaatac   1140
aagacactcg aatataacct cacaactact gaggtggtta tggagaacgt gactgccttc   1200
tgggaggagg ggttcggaga gctttttgag aaggccaaac agaataataa taaccgcaaa   1260
accagcaacg gcgacgacag cctgttcttc tccaattttt ctctcctggg aacacccgtc   1320
ctcaaagaca tcaactttaa gatcgagagg ggacagctgc tcgcagtcgc cggatccaca   1380
ggcgccggca agacctctct gctgatggtt atcatgggcg aactggagcc atccgagggc   1440
aagattaagc acagtggaag aatctccttt tgtagccagt tcagttggat tatgcccggc   1500
actattaagg agaatatcat ttttgggggtg agctatgatg agtatcggta tcggagcgtt   1560
atcaaagcct gtcagctgga ggaggatatc agcaaattcg cagagaagga taatatcgtg   1620
ctgggggagg ggggaatcac cctgagcgga ggccagagag ccagaatctc actggcccgg   1680
gccgtctaca aggacgccga cctttacctt ctggacagtc cctttggata tctggatgtg   1740
ctgactgaaa aggagatctt cgagtcttgt gtgtgcaagc tgatggctaa caagacccgg   1800
atcctagtga ctagtaagat ggagcacctg aagaaggcag acaagatctt gattctgcac   1860
gagggatcct cttactttta cggcaccttt agcgagctgc agaacctcca gcccgatttc   1920
tcatctaagc tgatgggctg tgatagcttc gaccagttct ctgccgagcg cagaaacagc   1980
atcctgacag agacactgca ccggtttttca ctggagggcg acgccctgt cagctggacc   2040 gagaccaaaa agcagtcttt caagcagaca ggcgagttcg gcgagaagcg caaaaacagc   2100
atcctgaatc caatcaactc tataaggaag tttagcatcg tgcagaagac accctccag   2160 atgaacggca tcgaagagga cagtgacgag cccctggagc ggcgcctgag cctcgtgcct   2220
gacagcgaac agggcgaggc catcctgcct aggatcagcg tgatttcaac cgggccaaca   2280
ctgcaggcta ggagaagaca gtcagtgctt aacctgatga cacatagcgt gaatcaggga   2340
cagaacatcc atcgaaaaac cacagcctct actcgcaaag tgtcactggc tcctcaggct   2400
aatctgacag agctggacat ctatagcagg aggctgagcc aggagacagg cctggagatc   2460
agtgaggaga tcaacgaaga ggacctgaag gagtgctttt tcgatgacat ggagagtatc   2520
cccgccgtca ccacctggaa tacctacctc cggtacatca cagtgcacaa gtccctcatc   2580
tttgtgctga tttggtgcct cgtgatcttt ctcgcagaag tggccgcctc cctggtggtg   2640
ctgtggctgt ggggaatac tccactgcag gacaaaggca attctacaca cagcaggaat   2700
aattcctatg ccgtgattat caccagcaca tcctcttact acgtgttcta catctacgtg   2760
ggagtggcag atactctgct tgcaatgggc ttcttcaggg ggctgcccct ggtgcacaca   2820
ctgatcacag tgtccaagat cctccaccat aaaatgctcc acagcgtgct gcaggcaccc   2880
atgagcaccc tgaacacact gaaggccggc ggcatcctga atcgcttttc caaagacatc   2940
gccatcctcg acgatctcct gccactgacc atcttcgatt ttatccagct gctgctgatc   3000
gtgatcgggg ccatcgccgt ggtggccgtg ctgcagccat acattttttcgt ggctacagtg   3060 cccgtgatct tgcctttat catgctgaga gcctacttcc tgcagacttc tcagcagctg   3120
aagcagctgg agagcgaagg gagaagcccc atcttcactc acctggtgac aagcctgaag   3180
ggactctgga ccctgagagc cttcggccgg cagccctatt cgagaccct gtttcacaag   3240 gccctcaacc tgcacacagc caactggttc ctctacctgt ccaccctgag gtggttccag   3300
atgaggattg aaatgatctt cgtgattttt ttcatcgccg tgacattcat tagcattctg   3360
```

-continued

```
accaccggcg aggggggaggg gagagtgggc atcatcctga cccttgccat gaacattatg    3420
tccacactgc agtgggccgt gaatagttca atcgacgtgg acagtctgat gaggtccgtg    3480
agccgggtgt tcaagttcat tgacatgccc acagagggga aacccaccaa aagcaccaag    3540
ccctacaaga acgggcagct gtccaaggtt atgatcatcg agaactctca cgtgaagaag    3600
gacgacattt ggcccagcgg cggccagatg acagtgaaag atctgaccgc caaatacacc    3660
gagggaggca acgccatcct cgaaaacatt agcttctcta tcagccctgg acagagggtg    3720
ggcctgctgg gccggacagg ctcagggaag agtactctgc tgtcagcatt cctgaggctc    3780
ctgaacacag agggcgagat ccagattgac ggcgtgtcct gggactccat caccctgcag    3840
cagtggcgga aggctttcgg ggtgatcccc cagaaggtgt tcatctttag cggcactttc    3900
agaaagaatc tggacccctta tgagcagtgg agtgaccagg agatctggaa agtggccgat    3960
gaggtcggac tgaggagcgt gatcgagcag tttccaggga agctggactt tgtgctggtg    4020 gatgggcggat gcgtgctgtc tcacggccat aaacagctga tgtgtctggc ccggtccgtg    4080
ctgtctaagg ccaagatcct gctgctggac gaaccctccg cccacctgga ccccgtgaca    4140
taccagatca tcaggagaac tctcaagcag gccttcgccg actgtaccgt gattctgtgc    4200
gagcaccgca ttgaagctat gctggagtgt cagcagttcc tggtgatcga ggaaaataag    4260
gtgaggcagt acgacagcat ccagaagctg ctgaacgagc gctccctgtt ccgccaggct    4320
atctccccat cagaccgggt gaaactcttc ccccacagaa actcctcaaa gtgcaagtcc    4380
aagccccaga tcgccgccct gaaggaggag accgaggagg aggtgcagga caccaggctg    4440
tga                                                                  4443
```

```
<210> SEQ ID NO 6
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 6
```

```
atgcagcgtt ctcccctgga gaaggcttct gtggtgagta aacttttttt ctcctggacc     60
agacctatcc tgaggaaagg ctacaggcag agactggagc tctctgacat ataccagata    120
ccttcagtcg atagcgccga caacctgagc gagaagctgg aacgcgagtg ggacagagag    180
ctggcaagca agaagaaccc aaagctgatt aatgccctga aaggtgtttt cttctggaga    240
ttcatgttct acggaatctt tctgtatctg ggggaggtta caaaggctgt gcaaccctcg    300
ctgctcggca gaatcatcgc ctcatacgat ccagacaaca aggaagaaag aagcatcgcc    360
atctacctgg gcattggcct ctgcctcctg tttattgtgc ggactctgct gctgcaccca    420
gcaattttcg ggttgcatca tattggcatg cagatgcgca ttgctatgtt ttccctcatc    480
tacaaaaaga cactgaaact cagctcccgg gtgctggaca agatctccat cggccaactg    540
gtgtctctcc tgagcaataa cttgaataag ttcgacgaag ggctggccct ggcacacttc    600
gtgtggattg cccccctgca ggtggccctg ctgatgggac tgatttggga actgctgcag    660
gctagcgctt ctgcggcct ggggttcctg atcgtgctgg cactgtttca ggcaggcctg    720
ggccgtatga tgatgaagta cagagaccag agggccggga agatctccga acggctcgtt    780
attacctctg agatgatcga gaacattcag tctgtgaaag cctactgctg ggaggaggct    840
atggagaaga tgatcgagaa tctgagacag accgagctga agctgaccag aaaggccgcc    900
```

-continued

```
tacgtgaggt acttcaacag cagtgccttc ttcttctctg gcttcttcgt tgtgtttctg      960
agcgtgctgc catacgctct catcaaaggc atcatcctgc ggaagatctt caccaccatc     1020
agcttttgca tcgtgcttag aatggccgtg acccggcagt tcccatgggc cgtgcaaact     1080
tggtatgatt ccctgggcgc catcaacaaa atccaggatt tcctgcagaa gcaggaatac     1140
aagacactcg aatataatct cacaactact gaggtggtta tggagaacgt gactgccttc     1200
tgggaggagg ggtccggaga gcttttttgag aaggcaaaac agaataacaa caaccgcaaa     1260
accagcaacg gcgacgacag cctgttcttc tccaattttt ctctcctggg aacacccgtc     1320
ctcaaagaca tcaactttaa gatcgagagg ggccagctgc tcgccgtcgc cggatccaca     1380
ggcgccggca agacctctct gctgatggtt atcatgggcg aactggagcc ctccgagggc     1440
aagattaagc actcaggaag aatctccttt tgtagccagt tcagttggat tatgcccggc     1500
actattaagg agaatatcat ttttgggggtg agctatgatg agtatcggta tcggagcgtt     1560
atcaaagcct gtcagctgga ggaggatatc agcaagttcg cagagaagga taatattgtg     1620
ctgggagagg gaggaatcac cctgagcgga ggccagagag ccagaatctc actggcccgg     1680
gccgtctaca aggacgccga cctttacctt ctggacagtc cctttggata tctggatgtg     1740
ctgactgaaa aggagatctt cgagtcttgt gtgtgcaagc tgatggctaa caagacccgg     1800
atcctagtga ctagtaagat ggagcacctg aagaaggcag acaagatctt gattctgcac     1860
gagggatcct cttacttta cggcacctt agcgagctgc agaacctcca gcccgatttc     1920
tcatctaagc tgatgggctg tgatagcttc gaccagttct ctgccgagcg cagaaacagc     1980
atcctgacag agacactgca ccggttttca ctggagggcg acgcccctgt cagctggacc     2040
gagaccaaaa agcagtcttt caagcagaca ggcgagttcg gcgagaagcg caaaaacagc     2100
atcctgaatc caatcaactc tataaggaag tttagcatcg tgcagaagac acccctccag     2160
atgaacggca tcgaagagga cagtgacgag cccctggagc ggcgcctgag cctcgtgcct     2220
gacagcgaac agggcgaggc catcctgcct aggatcagcg tgatttcaac cgggccaaca     2280
ctgcaggcta ggagaagaca gtcagtgctt aacctgatga cacatagcgt gaatcaggga     2340
cagaacatcc atcgaaaaac cacagcctct actcgcaaag tgtcactggc tcctcaggct     2400
aatctgacag agctggacat ctatagcagg aggctgagcc aggagacagg cctggagatc     2460
agtgaggaga tcaacgaaga ggacctgaag gagtgctttt tcgatgacat ggagagtatc     2520
cccgccgtca ccacctggaa tacctacctc cggtacatca cagtgcacaa gtccctcatc     2580
tttgtgctga tttggtgcct cgtgatcttt ctcgcagaag tggccgcctc cctggtggtg     2640
ctgtggctgt gggggaatac tccactgcag gacaaaggca attctacaca cagcaggaat     2700
aattcctatg ccgtgattat caccagcaca tcctcttact acgtgttcta catctacgtg     2760
ggagtggcag atactctgct tgcaatgggc ttcttcaggg ggctgccct ggtgcacaca     2820 ctgatcacag tgtccaagat cctccaccat aaaatgctcc acagcgtgct gcaggcaccc     2880
atgagcaccc tgaacacact gaaggccggc ggcatcctga atcgcttttc caaagacatc     2940
gccatcctcg acgatctcct gccactgacc atcttcgatt ttatccagct gctgctgatc     3000
gtgatcgggg ccatcgccgt ggtggccgtg ctgcagccat acattttcgt ggctacagtg     3060
cccgtgatcg ttgcctttat catgctgaga gcctacttcc tgcagacttc tcagcagctg     3120
aagcagctgg agagcgaagg gagaagcccc atcttcactc acctggtgac aagcctgaag     3180
ggactctgga ccctgagagc cttcggccgg cagcccatt tcgagaccct gtttcacaag     3240
gccctcaacc tgcacacagc caactggttc ctctacctgt ccacccctgag gtggttccag     3300
```

-continued

```
atgaggattg aaatgatctt cgtgatttt  ttcatcgccg tgacattcat tagcattctg      3360
accaccggcg aggggaggg gagagtgggc atcatcctga cccttgccat gaacattatg      3420
tccacactgc agtgggccgt gaatagttca atcgacgtgg acagtctgat gaggtccgtg      3480
agccgggtgt tcaagttcat tgacatgccc acagagggga aacccaccaa aagcaccaag      3540
ccctacaaga acgggcagct gtccaaggtt atgatcatcg agaactctca cgtgaagaag      3600
gacgacattt ggcccagcgg cggccagatg acagtgaaag atctgaccgc caaatacacc      3660
gagggaggca acgccatcct cgaaaacatt agcttctcta tcagccctgg acagagggtg      3720
ggcctgctgg gccggacagg ctcagggaag agtactctgc tgtcagcatt cctgaggctc      3780
ctgaacacag agggcgagat ccagattgac ggcgtgtcct gggactccat caccctgcag      3840
cagtggcgga aggctttcgg ggtgatcccc cagaaggtgt tcatctttag cggcactttc      3900
agaaagaatc tggacccta tgagcagtgg agtgaccagg agatctggaa agtggccgat      3960
gaggtcggac tgaggagcgt gatcgagcag tttccaggga agctggactt tgtgctggtg      4020
gatggcggat gcgtgctgtc tcacggccat aaacagctga tgtgtctggc ccggtccgtg      4080
ctgtctaagg ccaagatcct gctgctggac gaaccctccg cccacctgga ccccgtgaca      4140
taccagatca tcaggagaac tctcaagcag gccttcgccg actgtaccgt gattctgtgc      4200
gagcaccgca ttgaagctat gctggagtgt cagcagttcc tggtgatcga ggaaaataag      4260
gtgaggcagt acgacagcat ccagaagctg ctgaacgagc gctccctgtt ccgccaggct      4320
atctccccat cagaccgggt gaaactcttc ccccacagaa actcctcaaa gtgcaagtcc      4380
aagccccaga tcgccgccct gaaggaggag accgaggagg aggtgcagga caccaggctg      4440
tga                                                                       4443
```

<210> SEQ ID NO 7
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 7

```
atgcagcgtt ctccctgga gaaggcttct gtggtgagta aactttttt ctcctggacc          60 agacctatcc tgaggaaagg ctacaggcag agactggagc tctctgacat ataccagata         120
ccttcagtcg atagcgccga caacctgagc gagaagctgg aacgcgagtg ggacagagag         180
ctggcaagca agaagaaccc aaagctgatt aatgccctga aaggtgttt cttctggaga         240 ttcatgttct acggaatctt tctgtatctg ggggaggtta caaaggctgt gcaaccctg          300 ctgctcggca gaatcatcgc ctcatacgat ccagacaaca aggaagaaag aagcatcgcc         360
atctacctgg gcattggcct ctgcctcctg tttattgtgc ggactctgct gctgcaccca         420
gcaattttcg ggttgcatca tattggcatg cagatgcgca ttgctatgtt ttccctcatc         480
tacaaaaaga cactgaaact cagctcccgg gtgctggaca agatctccat cggccaactg         540
gtgtctctcc tgagcaataa cttgaataag ttcgacgaag ggctggccct ggcacacttc         600
gtgtggattg ccccctgca ggtggccctg ctgatggac tgatttggga actgctgcag          660
gctagcgctt tctgcggcct gggggttcctg atcgtgctgg cactgtttca ggcaggcctg       720
ggccgtatga tgatgaagta cagagaccag aggggccggga agatctccga acggctcgtt        780
attacctctg agatgatcga gaacattcag tctgtgaaag cctactgctg ggaggaggct         840
```

-continued

```
atggagaaga tgatcgagaa tctgagacag accgagctga agctgaccag aaaggccgcc      900
tacgtgaggt acttcaacag cagtgccttc ttcttctctg ggttcttcgt tgtgtttctg      960
agcgtgctgc catacgctct catcaaaggc atcatcctgc ggaagatctt caccaccatc     1020
agcttttgca tcgtgcttag aatggccgtg acacggcagt tcccatgggc cgttcaaact     1080
tggtatgatt ccctgggcgc catcaacaaa atccaggatt tcctgcagaa gcaggaatac     1140
aagacactcg aatataacct cacaactact gaggtggtta tggagaacgt gactgccttc     1200
tgggaggagg ggttcggaga gcttttgag aaggccaaac agaataataa taaccgcaaa      1260
accagcaacg gcgacgacag cctgttcttc tccattttt ctctcctggg aacacccgtc      1320
ctcaaagaca tcaactttaa gatcgagagg ggccagctgc tcgccgtcgc cggatccaca     1380
ggcgccggca agacctctct gctgatggtt atcatgggcg aactggagcc ctccgagggc     1440
aagattaagc actcaggaag aatctccttt tgtagccagt tcagttggat tatgcccggc     1500
actattaagg agaatatcat ttttggggtg agctatgatg agtatcggta tcggagcgtt     1560
atcaaagcct gtcagctgga ggaggatatc agcaagttcg cagagaagga taatattgtg     1620
ctgggagagg gaggaatcac cctgagcgga ggccagagag ccagaatctc actggcccgg     1680
gccgtctaca aggacgccga cctttacctt ctggacagtc cctttggata tctggatgtg     1740
ctgactgaaa aggagatctt cgagtcttgt gtgtgcaagc tgatggctaa caagacccgg     1800
atcctagtga ctagtaagat ggagcacctg aagaaggcag acaagatctt gattctgcac     1860
gagggatcct cttacttta cggcaccttt agcgagctgc agaacctcca gcccgatttc     1920
tcatctaagc tgatgggctg tgatagcttc gaccagttct ctgccgagcg cagaaacagc     1980
atcctgacag agacactgca ccggtttca ctggagggcg acgcccctgt cagctggacc      2040
gagaccaaaa agcagtcttt caagcagaca ggcgagttcg gcgagaagcg caaaaacagc     2100
atcctgaatc caatcaactc tataaggaag tttagcatcg tgcagaagac acccctccag     2160
atgaacggca tcgaagagga cagtgacgag cccctggagc ggcgcctgag cctcgtgcct     2220
gacagcgaac agggcgaggc catcctgcct aggatcagcg tgatttcaac cgggccaaca     2280
ctgcaggcta ggagaagaca gtcagtgctt aacctgatga cacatagcgt gaatcaggga     2340
cagaacatcc atcgaaaaac cacagcctct actcgcaaag tgtcactggc tcctcaggct     2400
aatctgacag agctggacat ctatagcagg aggctgagcc aggagacagg cctggagatc     2460
agtgaggaga tcaacgaaga ggacctgaag gagtgctttt tcgatgacat ggagagtatc     2520
cccgccgtca ccacctggaa tacctacctc cggtacatca cagtgcacaa gtccctcatc     2580
tttgtgctga tttggtgcct cgtgatcttt ctcgcagaag tggccgcctc cctggtggtg     2640
ctgtggctgt tggggaatac tccactgcag gacaaaggca attctacaca cagcaggaat     2700
aattcctatg ccgtgattat caccagcaca tcctcttact acgtgttcta catctacgtg     2760
ggagtggcag atactctgct tgcaatgggc ttcttcaggg ggctgcccct ggtgcacaca     2820
ctgatcacag tgtccaagat cctccaccat aaaatgctcc acagcgtgct gcaggcaccc     2880
atgagcaccc tgaacacact gaaggccggc ggcatcctga atcgcttttc caaagacatc     2940
gccatcctcg acgatctcct gccactgacc atcttcgatt ttatccagct gctgctgatc     3000
gtgatcgggg ccatcgccgt ggtggccgtg ctgcagccat acattttcgt ggctacagtg     3060
cccgtgatcg ttgcctttat catgctgaga gcctacttcc tgcagacttc tcagcagctg     3120
aagcagctga gagcgaagg gagaagcccc atcttcactc acctggtgac aagcctgaag     3180
ggactctgga ccctgagagc cttcggccgg cagccctatt tcgagaccct gtttcacaag     3240
```

-continued

```
gccctcaacc tgcacacagc caactggttc ctctacctgt ccaccctgag gtggttccag        3300
atgaggattg aaatgatctt cgtgattttt ttcatcgccg tgacattcat tagcattctg        3360
accaccggcg aggggagggg gagagtgggc atcatcctga cccttgccat gaacattatg        3420
agcacactgc agtgggccgt gaatagtagt atcgacgtgg acagtctgat gaggtccgtg        3480
agccgggtgt tcaagttcat tgacatgccc acagaaggga aacccaccaa aagcaccaag        3540
ccctacaaga acgggcagct gtccaaggtt atgatcatcg agaactctca cgtgaagaag        3600
gacgacattt ggcccagcgg cggccagatg acagtgaaag atctgaccgc caaatacacc        3660
gagggaggca acgccatcct cgaaaacatt agcttctcta tcagccctgg acagagggtg        3720
ggcctgctgg gccggacagg ctcagggaag agtactctgc tgtcagcatt cctgaggctc        3780
ctgaacacag agggcgagat ccagattgac ggcgtgtcct gggactccat caccctgcag        3840
cagtggcgga aggctttcgg ggtgatcccc cagaaggtgt tcatctttag cggcactttc        3900
agaaagaatc tggaccctta tgagcagtgg agtgaccagg agatctggaa agtggccgat        3960
gaggtcggac tgaggagcgt gatcgagcag tttccaggga agctggactt tgtgctggtg        4020
gatgccggat gcgtgctgtc tcacggccat aaacagctga tgtgtctggc ccggtccgtg        4080
ctgtctaagg ccaagatcct gctgctggac gaaccctccg cccacctgga ccccgtgaca        4140
taccagatca tcaggagaac tctcaagcag gccttcgccg actgtaccgt gattctgtgc        4200
gagcaccgca ttgaagctat gctggagtgt cagcagttcc tggtgatcga ggaaaataag        4260
gtgaggcagt acgacagcat ccagaagctg ctgaacgagc gctccctgtt ccgccaggct        4320
atctccccat cagaccgggt gaagctcttt ccccacagaa actcctcaaa gtgcaagtcc        4380
aagccccaga tcgccgccct gaaggaggag accgaggagg aggtgcagga caccaggctg        4440
tga                                                                      4443
```

```
<210> SEQ ID NO 8
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 8
```

```
atgcagcgtt ctcccctgga gaaggcttct gtggtgagta aacttttttt ctcctggacc          60
agacctatcc tgaggaaagg ctacaggcag agactggagc tctctgacat ataccagata         120
ccttcagtcg atagcgccga caacctgagc gagaagctgg aacgcgagtg ggacagagag         180
ctggcaagca agaagaaccc aaagctgatt aatgccctga aaggtgtttt cttctggaga         240
ttcatgttct acggaatctt tctgtatctg ggggaggtta caaaggctgt gcaacccctg         300
ctgctcggca gaatcatcgc ctcatacgat ccagacaata aggaagagag atctatcgcc         360
atctacctgg gaattggcct gtgtctgctg ttcatcgtgc gcaccctgct cctccaccca         420
gccatttttg ggctgcatca catcggaatg cagatgagga ttgctatgtt ttccctgatc         480
tataagaaga ccctgaaact ctcaagcaga gtgctggaca aaatttccat tggccagctg         540
gtgtctctgc tgtccaataa tctcaataag tttgacgagg gcctggccct ggcacacttc         600
gtctggattg cccctctcca ggtcgctctg ctgatgggcc tgatctggga gctgctgcag        660
gcatccgctt tctgcggcct ggggttcctg atcgtgctgg cactgtttca ggcaggcctg        720
ggccgtatga tgatgaagta cagagaccag agggccggga agatctccga acggctcgtt        780
```

-continued

```
attacctctg agatgatcga gaacattcag tctgtgaaag cctactgctg ggaggaggct      840
atggagaaga tgatcgagaa tctgagacag accgagctga agctgaccag aaaggccgcc      900
tacgtgaggt acttcaacag cagtgccttc ttcttctctg gcttcttcgt tgtgtttctg      960
agcgtgctgc catacgctct catcaaaggc atcatcctga ggaagatctt cactacaatc     1020
tccttctgca tcgtactcag aatggccgtg acccgccagt ttccctgggc cgtgcagaca     1080
tggtacgact ccctcggcgc cattaataag atccaggatt ttctgcagaa acaggaatac     1140
aagacactgg aatacaacct gacaacaaca gaggtggtca tggaaaacgt gaccgcattt     1200
tgggaggaag gcttcggaga gctctttgaa aaagctaagc agaacaacaa taacaggaaa     1260
acctctaatg gggacgacag cctgtttttc agcaattttt ctctgctggg gacacctgtg     1320
ctgaaggaca ttaactttaa gatcgagagg ggacagctgc tcgcagtcgc cggatccaca     1380
ggcgccggca agacctctct gctgatggtt atcatgggcg aactggagcc atccgagggc     1440
aagattaagc acagtggaag aatctccttt tgtagccagt tcagttggat tatgcccggc     1500
actattaagg agaatatcat ttttgggggtg agctatgatg agtatcggta tcggagcgtt     1560
atcaaagcct gtcagctgga ggaggatatc agcaaattcg cagagaagga taatatcgtg     1620
ctgggggagg ggggaatcac cctgagcgga ggccagagag ccagaatcag cctggcaagg     1680
gcagtgtata aagacgctga cctgtacttg ctggactccc cttttggcta cctggacgtg     1740
ctgaccgaaa aggaaatctt tgagtcctgc gtctgcaagc tgatggcaaa caagaccaga     1800
atcctggtga cctccaagat ggaacatctg aagaaggcag ataaaatcct catcctgcat     1860
gagggatctt cttactttta tggaactttt agcgagctgc agaacctgca gccagacttc     1920
tccagcaagc tgatgggatg cgactccttt gaccagttct ccgccgaacg gcgcaattct     1980
atcctgaccg aaaccctgca ccggttttca ctggagggcg acgccctgt cagctggacc     2040 gagaccaaaa agcagtcttt caagcagaca ggcgagttcg gcgagaagcg caaaaacagc     2100
atcctgaatc caatcaactc tataaggaag tttagcatcg tgcagaagac acccctccag     2160
atgaacggca tcgaagagga cagtgacgag cccctggagc ggcgcctgag cctcgtgcct     2220
gacagcgaac agggcgaggc catcctgcct aggatcagcg tgatttcaac cgggccaaca     2280
ctgcaggcta ggagaagaca gtcagtgctt aacctgatga cacatagcgt gaatcaggga     2340
cagaacatcc atcgaaaaac cacagcctct actcgcaaag tgtcactggc tcctcaggct     2400
aatctgacag agctggacat ctatagcagg aggctgagcc aggagacagg cctggagatc     2460
agtgaggaga tcaacgaaga ggacctgaag gagtgctttt tcgatgacat ggagagtatc     2520
cccgccgtca ccacctggaa tacctacctc cggtacatca cagtgcacaa gtccctcatc     2580
tttgtgctga tttggtgcct cgtgatcttt ctcgcagaag tggccgcctc cctggtggtg     2640
ctgtggctgt tggggaatac tccactgcag gacaaaggca attctacaca cagcaggaat     2700
aattcctatg ccgtgattat caccagcaca tcctcttact acgtgttcta catctacgtg     2760
ggagtggcag atactctgct tgcaatgggc ttcttcaggg gctgcccct ggtgcacaca     2820 ctgatcacag tgtccaagat cctccaccat aaaatgctcc acagcgtgct gcaggcaccc     2880
atgagcaccc tgaacacact gaaggccggc ggcatcctga atcgcttttc caaagacatc     2940
gccatcctcg acgatctcct gccactgacc atcttcgatt ttatccagct gctgctgatc     3000
gtgatcgggg ccatcgccgt ggtggccgtg ctgcagccat acattttcgt ggctacagtg     3060
cccgtgatcg ttgcctttat catgctgaga gcctacttcc tgcagacttc tcagcagctg     3120
aagcagctgg agagcgaagg gagaagcccc atcttcactc acctggtgac aagcctgaag     3180
```

-continued

```
ggactctgga ccctgagagc cttcggccgg cagccctatt tcgagaccct gtttcacaag    3240
gccctcaacc tgcacacagc caactggttt ctctacctgt ccaccctgag gtggttccag    3300
atgaggattg aaatgatctt cgtgattttt ttcatcgccg tgacattcat tagcattctg    3360
accaccggcg aggggaggg gagagtgggc atcatcctga cccttgccat gaacattatg    3420
tccacactgc agtgggccgt gaatagttca atcgacgtgg acagtctgat gaggtccgtg    3480
agccgggtgt tcaagttcat tgacatgccc acagagggga aacccaccaa aagcaccaag    3540
ccctacaaga acgggcagct gtccaaggtt atgatcatcg agaactctca cgtgaagaag    3600
gacgacattt ggcccagcgg cggccagatg acagtgaaag atctgaccgc caaatacacc    3660
gagggaggca acgccatcct cgaaaacatt agcttctcta tcagccctgg acagagggtg    3720
ggcctgctgg gccggacagg ctcagggaag agtactctgc tgtcagcatt cctgaggctc    3780
ctgaacacag agggcgagat ccagattgac ggcgtgtcct gggactccat caccctgcag    3840
cagtggcgga aggctttcgg ggtgatcccc cagaaggtgt tcatctttag cggcactttc    3900
agaaagaatc tggacccttta tgagcagtgg agtgaccagg agatctggaa agtggccgat    3960
gaggtcggac tgaggagcgt gatcgagcag tttccaggga agctggactt tgtgctggtg    4020
gatggcggat gcgtgctgtc tcacggccat aaacagctga tgtgtctggc ccggtccgtg    4080
ctgtctaagg ccaagatcct gctgctggac gaaccctccg cccacctgga ccccgtgaca    4140
taccagatca tcaggagaac tctcaagcag gccttcgccg actgtaccgt gattctgtgc    4200
gagcaccgca ttgaagctat gctggagtgt cagcagttcc tggtgatcga ggaaaataag    4260
gtgaggcagt acgacagcat ccagaagctg ctgaacgagc gctccctgtt ccgccaggct    4320
atctccccat cagaccgggt gaaactcttc ccccacagaa actcctcaaa gtgcaagtcc    4380
aagccccaga tcgccgccct gaaggaggag accgaggagg aggtgcagga caccaggctg    4440
tga                                                                  4443
```

<210> SEQ ID NO 9
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 9

```
atgcagcgct cgcctctgga aaaggcgagc gtcgtgtcaa agctattctt ttcttggacc      60
cggcccattc tcaggaaggg ctacaggcag aggctggagt tgagcgacat ctatcagatt     120
ccttccgtgg acagcgccga caacctgagc gagaagctgg aaagggagtg ggaccgcgaa     180
ctggcaagca aaaagaaccc caagctgatc aatgccctga aaggtgtttt cttttggagaa     240 ttcatgttct acgggatctt tctgtatctg ggcgaggtta caaaggctgt gcagcccctg     300
ctgctcggca gaatcatcgc ctcatacgat ccagacaaca aggaagaaag aagcatcgcc     360
atctacctgg cattggcct ctgcctcctg tttattgtgc ggactctgct gctgcaccca     420
gcaattttcg ggttgcatca tattggcatg cagatgcgca ttgctatgtt ttccctcatc     480
tacaaaaaga cactgaaact cagctcccgg gtgctggaca agatctccat cggccaactg     540
gtgtctctcc tgagcaataa cttgaataag ttcgacgaag ggctggccct ggcacacttc     600
gtgtggattg ccccctgca ggtggccctg ctgatgggac tgatttggga actgctgcag     660
gctagcgctt tctgcggcct ggggttcctg atcgtgctgg cactgttca ggcaggcctg     720
```

-continued

```
ggccgtatga tgatgaagta cagagaccag agggccggga agatctccga acggctcgtt      780
attacctctg agatgatcga gaacattcag tctgtgaaag cctactgctg ggaggaggct      840
atggagaaga tgatcgagaa tctgagacag accgagctga agctgaccag aaaggccgcc      900
tacgtgaggt acttcaacag cagtgccttc ttcttctctg ggttcttcgt tgtgtttctg      960
agcgtgctgc catacgctct catcaaaggc atcatcctgc ggaagatctt caccaccatc     1020
agcttttgca tcgtgcttag aatggccgtg acacggcagt tcccatgggc cgttcaaact     1080
tggtatgatt ccctgggcgc catcaacaaa atccaggatt tcctgcagaa gcaggaatac     1140
aagacactcg aatataacct cacaactact gaggtggtta tggagaacgt gactgccttc     1200
tgggaggagg ggttcggaga gcttttttgag aaggccaaac agaataataa taaccgcaaa     1260
accagcaacg cgacgacag cctgttcttc tccaattttt ctctcctggg aacacccgtc      1320
ctcaaagaca tcaactttaa gatcgagagg ggccagctgc tcgccgtcgc cggatccaca     1380
ggcgccggca agacctctct gctgatggtt atcatgggcg aactggagcc ctccgagggc     1440
aagattaagc actcaggaag aatctccttt tgtagccagt tcagttggat tatgcccggc     1500
actattaagg agaatatcat ttttgggggtg agctatgatg agtatcggta tcggagcgtt     1560
atcaaagcct gtcagctgga ggaggatatc agcaagttcg cagagaagga taatattgtg     1620
ctgggagagg gaggaatcac cctgagcgga ggccagagag ccagaatctc actggcccgg     1680
gccgtctaca aggacgccga cctttacctt ctggacagtc cctttggata tctggatgtg     1740
ctgactgaaa aggagatctt cgagtcttgt gtgtgcaagc tgatggctaa caagacccgg     1800
atcctagtga ctagtaagat ggagcacctg aagaaggcag acaagatctt gattctgcac     1860
gagggatcct cttactttta cggcaccttt agcgagctgc agaacctcca gcccgatttc     1920
tcatctaagc tgatgggctg tgatagcttc gaccagttct ctgccgagcg cagaaacagc     1980
atcctgacag agacactgca ccggttttca ctggagggcg acgccctgt cagctggacc      2040 gagaccaaaa agcagtcttt caagcagaca ggcgagttcg gcgagaagcg caaaaacagc     2100
atcctgaatc caatcaactc tataaggaag tttagcatcg tgcagaagac acccctccag     2160
atgaacggca tcgaagagga cagtgacgag ccccctggagc ggcgcctgag cctcgtgcct     2220
gacagcgaac agggcgaggc catcctgcct aggatcagcg tgatttcaac cgggccaaca     2280
ctgcaggcta ggagaagaca gtcagtgctt aacctgatga cacatagcgt gaatcaggga     2340
cagaacatcc atcgaaaaac cacagcctct actcgcaaag tgtcactggc tcctcaggct     2400
aatctgacag agctggacat ctatagcagg aggctgagcc aggagacagg cctggagatc     2460
agtgaggaga tcaacgaaga ggacctgaag gagtgctttt tcgatgacat ggagagtatc     2520
cccgccgtca ccacctggaa tacctacctc cggtacatca cagtgcacaa gtccctcatc     2580
tttgtgctga tttggtgcct cgtgatcttt ctcgcagaag tggccgcctc cctggtggtg     2640
ctgtggctgt tggggaatac tccactgcag gacaaaggca attctacaca cagcaggaat     2700
aattcctatg ccgtgattat caccagcaca tcctcttact acgtgttcta catctacgtg     2760
ggagtggcag atactctgct tgcaatgggc ttcttcaggg ggctgccccct ggtgcacaca     2820 ctgatcacag tgtccaagat cctccaccat aaaaatgctcc acagcgtgct gcaggcaccc     2880
atgagcaccc tgaacacact gaaggccggc ggcatcctga atcgctttttc caaagacatc     2940 gccatcctcg acgatctcct gccactgacc atcttcgatt ttatccagct gctgctgatc     3000
gtgatcgggg ccatcgccgt ggtggccgtg ctgcagccat acatttttcgt ggctacagtg     3060 cccgtgatcg ttgcctttat catgctgaga gcctacttcc tgcagacttc tcagcagctg     3120
```

-continued

```
aagcagctgg agagcgaagg gagaagcccc atcttcactc acctggtgac aagcctgaag     3180
ggactctgga ccctgagagc cttcggccgg cagccctatt tcgagaccct gtttcacaag     3240
gccctcaacc tgcacacagc caactggttc ctctacctgt ccaccctgag gtggttccag     3300
atgaggattg aaatgatctt cgtgattttt ttcatcgccg tgacattcat tagcattctg     3360
accaccggcg aggggggaggg gagagtgggc atcatcctga cccttgccat gaacattatg     3420
agcacactgc agtgggccgt gaatagtagt atcgacgtgg acagtctgat gaggtccgtg     3480
agccgggtgt tcaagttcat tgacatgccc acagaaggga aacccaccaa aagcaccaag     3540
ccctacaaga acgggcagct gtccaaggtt atgatcatcg agaactctca cgtgaagaag     3600
gacgacattt ggcccagcgg cggccagatg acagtgaaag atctgaccgc caaatacacc     3660
gagggaggca acgccatcct cgaaaacatt agcttctcta tcagccctgg acagagggtg     3720
ggcctgctgg gccggacagg ctcagggaag agtactctgc tgtcagcatt cctgaggctc     3780
ctgaacacag agggcgagat ccagattgac ggcgtgtcct gggactccat caccctgcag     3840
cagtggcgga aggctttcgg ggtgatcccc cagaaggtgt tcatctttag cggcacttc      3900 agaaagaatc tggacccctta tgagcagtgg agtgaccagg agatctggaa agtggccgat    3960
gaggtcggac tgaggagcgt gatcgagcag tttccaggga agctggactt tgtgctggtg     4020 gatgcggat gcgtgctgtc tcacggccat aaacagctga tgtgtctggc ccggtccgtg      4080
ctgtctaagg ccaagatcct gctgctggac gaaccctccg cccacctgga ccccgtgaca    4140
taccagatca tcaggagaac tctcaagcag gccttcgccg actgtaccgt gattctgtgc    4200
gagcaccgca ttgaagctat gctggagtgt cagcagttcc tggtgatcga ggaaaataag    4260
gtgaggcagt acgacagcat ccagaagctg ctgaacgagc gctccctgtt ccgccaggct    4320
atctccccat cagaccgggt gaaactcttc ccccacagaa actcctcaaa gtgcaagtcc    4380
aagccccaga tcgccgccct gaaggaggag accgaggagg aggtgcagga caccaggctg    4440
tga                                                                   4443
```

```
<210> SEQ ID NO 10
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 10
```

```
atgcagcgtt ctccctgga gaaggcttct gtggtgagta aactttttt ctcctggacc        60 agacctatcc tgaggaaagg ctacaggcag agactggagc tctctgacat ataccagata      120
ccttcagtcg atagcgccga caacctgagc gagaagctgg aacgcgagtg ggacagagag      180
ctggcaagca agaagaaccc aaagctgatt aatgccctga gaaggtgttt cttctggaga      240
ttcatgttct acggaatctt tctgtatctg ggggaggtta caaaggctgt gcaaccctg       300 ctgctcggca gaatcatcgc ctcatacgat ccagacaata aggaagagag atctatcgcc      360
atctacctgg gaattggcct gtgtctgctg ttcatcgtgc gcaccctgct cctccaccca      420
gccatttttg ggctgcatca catcggaatg cagatgagga ttgctatgtt ttccctgatc      480
tataagaaga ccctgaaact ctcaagcaga gtgctggaca aaatttccat tggccagctg      540
gtgtctctgc tgtccaataa tctcaataag tttgacgagg gcctggccct ggcacacttc      600
gtctggattg cccctctcca ggtcgctctg ctgatgggcc tgatctggga gctgctgcag      660
```

-continued

```
gcatccgctt tctgcggcct ggggttcctg atcgtgctgg cactgtttca ggcaggcctg      720
ggccgtatga tgatgaagta cagagaccag agggccggga agatctccga acggctcgtt      780
attacctctg agatgatcga gaacattcag tctgtgaaag cctactgctg ggaggaggct      840
atggagaaga tgatcgagaa tctgagacag accgagctga agctgaccag aaaggccgcc      900
tacgtgaggt acttcaacag cagtgccttc ttcttctctg ggttcttcgt tgtgtttctg      960
agcgtgctgc catacgctct catcaaaggc atcatcctga ggaagatctt cactacaatc     1020
tccttctgca tcgtactcag aatggccgtg acccgccagt ttccctgggc cgtgcagaca     1080
tggtacgact ccctcggcgc cattaataag atccaggatt ttctgcagaa acaggaatac     1140
aagacactgg aatacaacct gacaacaaca gaggtggtca tggaaaacgt gaccgcattt     1200
tgggaggaag gcttcggaga gctctttgaa aaagctaagc agaacaacaa taacaggaaa     1260
acctctaatg gggacgacag cctgtttttc agcaattttt ctctgctggg gacacctgtg     1320
ctgaaggaca ttaactttaa gatcgagagg ggacagctgc tcgcagtcgc cggatccaca     1380
ggcgccggca agacctctct gctgatggtt atcatgggcg aactggagcc atccgagggc     1440
aagattaagc acagtggaag aatctccttt tgtagccagt tcagttggat tatgcccggc     1500
actattaagg agaatatcat ttttgggggtg agctatgatg agtatcggta tcggagcgtt     1560
atcaaagcct gtcagctgga ggaggatatc agcaaattcg cagagaagga taatatcgtg     1620
ctgggggagg ggggaatcac cctgagcgga ggccagagag ccagaatttc tctggccaga     1680
gccgtgtaca aagatgccga cctgtacctg ctggacagcc catttggcta tctggacgtg     1740
ctgaccgaaa aagagatttt cgagtcatgc gtttgtaagc tgatggccaa caagactcgc     1800
atcctggtga cttcgaagat ggaacatctg aagaaagctg ataagattct gatcctgcac     1860
gaaggcagct cctactttta cgggaccttc tccgagctcc agaacctgca gcctgatttc     1920
agctctaagc tgatgggctg cgatagcttt gaccagttta gcgcagaaag cgcgcaactct    1980 attctgactg agacactgca ccggtttttca ctggagggcg acgcccctgt cagctggacc     2040
gagaccaaaa agcagtcttt caagcagaca ggcgagttcg gcgagaagcg caaaaacagc     2100
atcctgaatc caatcaactc tataaggaag tttagcatcg tgcagaagac accctccag      2160 atgaacggca tcgaagagga cagtgacgag cccctggagc ggcgcctgag cctcgtgcct     2220
gacagcgaac agggcgaggc catcctgcct aggatcagcg tgatttcaac cgggccaaca     2280
ctgcaggcta ggagaagaca gtcagtgctt aacctgatga cacatagcgt gaatcaggga     2340
cagaacatcc atcgaaaaac cacagcctct actcgcaaag tgtcactggc tcctcaggct     2400
aatctgacag agctggacat ctatagcagg aggctgagcc aggagacagg cctggagatc     2460
agtgaggaga tcaacgaaga ggacctgaag gagtgctttt tcgatgacat ggagagtatc     2520
cccgccgtca ccacctggaa tacctacctc cggtacatca cagtgcacaa gtccctcatc     2580
tttgtgctga tttggtgcct cgtgatcttt ctcgcagaag tggccgcctc cctggtggtg     2640
ctgtggctgt tggggaatac tccactgcag gacaaaggca attctacaca cagcaggaat     2700
aattcctatg ccgtgattat caccagcaca tcctcttact acgtgttcta catctacgtg     2760
ggagtggcag atactctgct tgcaatgggc ttcttcaggg gctgcccct ggtgcacaca      2820 ctgatcacag tgtccaagat cctccaccat aaaatgctcc acagcgtgct gcaggcaccc     2880
atgagcaccc tgaacacact gaaggccggc ggcatcctga atcgcttttc caaagacatc     2940
gccatcctcg acgatctcct gccactgacc atcttcgatt ttatccagct gctgctgatc     3000
gtgatcgggg ccatcgccgt ggtggccgtg ctgcagccat acattttcgt ggctacagtg     3060
```

-continued

```
cccgtgatcg ttgcctttat catgctgaga gcctacttcc tgcagacttc tcagcagctg       3120
aagcagctgg agagcgaagg gagaagcccc atcttcactc acctggtgac aagcctgaag       3180
ggactctgga ccctgagagc cttcggccgg cagccctatt tcgagaccct gtttcacaag       3240
gccctcaacc tgcacacagc caactggttt ctctacctgt ccaccctgag gtggttccag       3300
atgaggattg aaatgatctt cgtgattttt ttcatcgccg tgacattcat tagcattctg       3360
accaccggcg agggggaggg gagagtgggc atcatcctga cccttgccat gaacattatg       3420
tccacactgc agtgggccgt gaatagttca atcgacgtgg acagtctgat gaggtccgtg       3480
agccgggtgt tcaagttcat tgacatgccc acagaggggg aacccaccaa aagcaccaag       3540
ccctacaaga acgggcagct gtccaaggtt atgatcatcg agaactctca cgtgaagaag       3600
gacgacattt ggcccagcgg cggccagatg acagtgaaag atctgaccgc caaatacacc       3660
gagggaggca acgccatcct cgaaaacatt agcttctcta tcagccctgg acagagggtg       3720
ggcctgctgg gccggacagg ctcagggaag agtactctgc tgtcagcatt cctgaggctc       3780
ctgaacacag agggcgagat ccagattgac ggcgtgtcct gggactccat caccctgcag       3840
cagtggcgga aggctttcgg ggtgatcccc cagaaggtgt tcatctttag cggcacttttc       3900 agaaagaatc tggacccctta tgagcagtgg agtgaccagg agatctggaa agtggccgat       3960
gaggtcggac tgaggagcgt gatcgagcag tttccaggga agctggactt tgtgctggtg       4020
gatggcggat gcgtgctgtc tcacggccat aaacagctga tgtgtctggc ccggtccgtg       4080
ctgtctaagg ccaagatcct gctgctggac gaaccctccg cccacctgga ccccgtgaca       4140
taccagatca tcaggagaac tctcaagcag gccttcgccg actgtaccgt gattctgtgc       4200
gagcaccgca ttgaagctat gctggagtgt cagcagttcc tggtgatcga ggaaaataag       4260
gtgaggcagt acgacagcat ccagaagctg ctgaacgagc gctccctgtt ccgccaggct       4320
atctccccat cagaccgggt gaaactcttc ccccacagaa actcctcaaa gtgcaagtcc       4380
aagccccaga tcgccgccct gaaggaggag accgaggagg aggtgcagga caccaggctg       4440
tga                                                                     4443
```

<210> SEQ ID NO 11
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 11

```
atgcagcgct cgcctctgga aaaggcgagc gtcgtgtcaa agctattctt ttcttggacc         60
cggcccattc tcaggaaggg ctacaggcag aggctggagt tgagcgacat ctatcagatt        120
ccttccgtgg acagcgccga caacctgagc gagaagctgg aaagggagtg ggaccgcgaa        180
ctggcaagca aaagaaccc caagctgatc aatgccctga aaggtgtttt cttttggaga        240
ttcatgttct acgggatctt tctgtatctg ggcgaggtta caaaggctgt gcagcccctg        300
ctgctcggca gaatcatcgc ctcatacgat ccagacaata aggaagagag atctatcgcc        360
atctacctgg gaattggcct gtgtctgctg ttcatcgtgc gcaccctgct cctccaccca        420
gccatttttg ggctgcatca atcggaatg cagatgagga ttgctatgtt ttccctgatc        480
tataagaaga ccctgaaact ctcaagcaga gtgctggaca aaatttccat tggccagctg        540
gtgtctctgc tgtccaataa tctcaataag tttgacgagg cctggcccct ggcacacttc        600
```

-continued

```
gtctggattg cccctctcca ggtcgctctg ctgatgggcc tgatctggga gctgctgcag      660
gcatccgctt tctgcggcct ggggttcctg atcgtgctgg cactgtttca ggcaggcctg      720
ggccgtatga tgatgaagta cagagaccag agggccggga agatctccga acggctcgtt      780
attacctctg agatgatcga gaacattcag tctgtgaaag cctactgctg ggaggaggct      840
atggagaaga tgatcgagaa tctgagacag accgagctga agctgaccag aaaggccgcc      900
tacgtgaggt acttcaacag cagtgccttc ttcttctctg gcttcttcgt tgtgtttctg      960
agcgtgctgc catacgctct catcaaaggc atcatcctga gaaaaatttt cacaaccatc     1020 tcctttttgca tcgtgctgag aatggccgtg acaaggcagt tcccttgggc tgtgcagacc     1080
tggtacgaca gcctgggagc tattaataag attcaagatt tcctgcagaa gcaggaatac     1140
aaaacactgg aatacaacct gacaactact gaggtcgtta tggagaacgt gacagcattt     1200
tgggaggagg ggttcgggga actcttcgag aaggcaaagc agaacaacaa caatcggaag     1260
acatccaacg gcgacgacag cctgttcttt tccaacttca gcctgctggg aactccagtg     1320
ctcaaagaca ttaactttaa gatcgagagg ggccagctgc tcgccgtcgc cggatccaca     1380
ggcgccggca agacctctct gctgatggtt atcatgggcg aactggagcc ctccgagggc     1440
aagattaagc actcaggaag aatctccttt tgtagccagt tcagttggat tatgcccggc     1500
actattaagg agaatatcat ttttgggggtg agctatgatg agtatcggta tcggagcgtt     1560
atcaaagcct gtcagctgga ggaggatatc agcaagttcg cagagaagga taatattgtg     1620
ctgggagagg gaggaatcac cctgagcgga ggccagagag ccagaattag cctcgcccgg     1680
gcagtctaca aagatgccga cctgtacctg ctggacagcc cttttggcta tttggatgtg     1740
ctgactgaaa aggaaatctt cgagagctgc gtgtgcaagc tgatggccaa caagacccgc     1800
atcctcgtca ctagcaagat ggaacacctg aagaaggccg acaagatcct gattctgcac     1860
gaggggagca gctacttcta tggcactttt tccgagctgc aaaatctcca gcctgacttc     1920
tcttccaagc tgatgggatg tgacagcttt gaccagtttt ccgctgagcg cgcgcaatagc     1980 atcctgaccg aaaccctgca ccggttttca ctggagggcg acgcccctgt cagctggacc     2040
gagaccaaaa agcagtcttt caagcagaca ggcgagttcg gcgagaagcg caaaaacagc     2100
atcctgaatc caatcaactc tataaggaag tttagcatcg tgcagaagac acccctccag     2160
atgaacggca tcgaagagga cagtgacgag ccccctggagc ggcgcctgag cctcgtgcct     2220
gacagcgaac agggcgaggc catcctgcct aggatcagcg tgatttcaac cgggccaaca     2280
ctgcaggcta ggagaagaca gtcagtgctt aacctgatga cacatagcgt gaatcaggga     2340
cagaacatcc atcgaaaaac cacagcctct actcgcaaag tgtcactggc tcctcaggct     2400
aatctgacag agctggacat ctatagcagg aggctgagcc aggagacagg cctggagatc     2460
agtgaggaga tcaacgaaga ggacctgaag gagtgctttt cgatgacat ggagagtatc     2520 cccgccgtca ccacctggaa tacctacctc cggtacatca cagtgcacaa gtccctcatc     2580
tttgtgctga tttggtgcct cgtgatcttt ctcgcagaag tggccgcctc cctggtggtg     2640
ctgtggctgt gggggaatac tccactgcag gacaaaggca attctacaca cagcaggaat     2700
aattcctatg ccgtgattat caccagcaca tcctcttact acgtgttcta catctacgtg     2760
ggagtggcag atactctgct tgcaatgggc ttcttcaggg gctgcccct ggtgcacaca     2820 ctgatcacag tgtccaagat cctccaccat aaaaatgctcc acagcgtgct gcaggcaccc     2880
atgagcaccc tgaacacact gaaggccggc ggcatcctga atcgcttttc caaagacatc     2940
gccatcctcg acgatctcct gccactgacc atcttcgatt ttatccagct gctgctgatc     3000
```

-continued

```
gtgatcgggg ccatcgccgt ggtggccgtg ctgcagccat acattttcgt ggctacagtg    3060
cccgtgatcg ttgcctttat catgctgaga gcctacttcc tgcagacttc tcagcagctg    3120
aagcagctgg agagcgaagg gagaagcccc atcttcactc acctggtgac aagcctgaag    3180
ggactctgga ccctgagagc cttcggccgg cagcccatt tcgagaccct gtttcacaag    3240
gccctcaacc tgcacacagc caactggttc ctctacctgt ccaccctgag gtggttccag    3300
atgaggattg aaatgatctt cgtgattttt ttcatcgccg tgacattcat tagcattctg    3360
accaccggcg aggggagggg gagagtgggc atcatcctga cccttgccat gaacattatg    3420
agcacactgc agtgggccgt gaatagtagt atcgacgtgg acagtctgat gaggtccgtg    3480
agccgggtgt tcaagttcat tgacatgccc acagaaggga aacccaccaa aagcaccaag    3540
ccctacaaga acgggcagct gtccaaggtt atgatcatcg agaactctca cgtgaagaag    3600
gacgacattt ggcccagcgg cggccagatg acagtgaaag atctgaccgc caaatacacc    3660
gagggaggca acgccatcct cgaaaacatt agcttctcta tcagccctgg acagagggtg    3720
ggcctgctgg gccggacagg ctcagggaag agtactctgc tgtcagcatt cctgaggctc    3780
ctgaacacag agggcgagat ccagattgac ggcgtgtcct gggactccat caccctgcag    3840
cagtggcgga aggctttcgg ggtgatcccc cagaaggtgt tcatctttag cggcactttc    3900
agaaagaatc tggacccta tgagcagtgg agtgaccagg agatctggaa agtggccgat    3960
gaggtcggac tgaggagcgt gatcgagcag tttccaggga agctggactt tgtgctggtg    4020
gatggcggat gcgtgctgtc tcacggccat aaacagctga tgtgtctggc ccggtccgtg    4080
ctgtctaagg ccaagatcct gctgctggac gaaccctccg cccacctgga ccccgtgaca    4140
taccagatca tcaggagaac tctcaagcag gccttcgccg actgtaccgt gattctgtgc    4200
gagcaccgca ttgaagctat gctggagtgt cagcagttcc tggtgatcga ggaaaataag    4260
gtgaggcagt acgacagcat ccagaagctg ctgaacgagc gctccctgtt ccgccaggct    4320
atctccccat cagaccgggt gaaactcttc ccccacagaa actcctcaaa gtgcaagtcc    4380
aagccccaga tcgccgccct gaaggaggag accgaggagg aggtgcagga caccaggctg    4440
tga                                                                  4443
```

<210> SEQ ID NO 12
<211> LENGTH: 140
<212> TYPE: RNA
<213> ORGANISM: Artificial Sequence
<220> FEATURE:
<223> OTHER INFORMATION: Synthetic polynucleotide

<400> SEQUENCE: 12

```
ggacagaucg ccuggagacg ccauccacgc uguuuugacc uccauagaag acaccgggac      60
cgauccagcc uccgcggccg ggaacggugc auuggaacgc ggauuccccg ugccaagagu     120
gacucaccgu ccuugacacg                                                 140
```

<210> SEQ ID NO 13
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 13

```
cggguggcau cccugugacc ccuccccagu gccucuccug gcccuggaag uugccacucc      60
```

```
agugcccacc agccuugucc uaauaaaauu aaguugcauc aagcu                  105

<210> SEQ ID NO 14
<211> LENGTH: 105
<212> TYPE: RNA
<213> ORGANISM: Artificial Sequence
<220> FEATURE:
<223> OTHER INFORMATION: Synthetic polynucleotide

<400> SEQUENCE: 14
ggguggcauc ccugugaccc cucccccagug ccucuccugg cccuggaagu ugccacucca     60
gugcccacca gccuuguccu aauaaaauua aguugcauca aagcu                  105

<210> SEQ ID NO 15
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 15
atgcaacgct ctcctcttga aaaggcctcg gtggtgtcca agctcttctt ctcgtggact     60
agacccatcc tgagaaaggg gtacagacag cgcttggagc tgtccgatat ctatcaaatc    120
ccttccgtgg actccgcgga caacctgtcc gagaagctcg agagagaatg ggacagagaa    180
ctcgcctcaa agaagaaccc gaagctgatt aatgcgctta ggcggtgctt tttctggcgg    240
ttcatgttct acggcatctt cctctacctg ggagaggtca ccaaggccgt gcagcccctg    300
ttgctgggac ggattattgc ctcctacgac cccgacaaca aggaagaaag aagcatcgct    360
atctacttgg gcatcggtct gtgcctgctt ttcatcgtcc ggaccctctt gttgcatcct    420
gctattttcg gcctgcatca cattggcatg cagatgagaa ttgccatgtt ttccctgatc    480
tacaagaaaa ctctgaagct ctcgagccgc gtgcttgaca agatttccat cggccagctc    540
gtgtccctgc tctccaacaa tctgaacaag ttcgacgagg gcctcgccct ggcccacttc    600
gtgtggatcg cccctctgca agtggcgctt ctgatgggcc tgatctggga gctgctgcaa    660
gcctcggcat tctgtgggct tggattcctg atcgtgctgg cactgttcca ggccggactg    720
gggcggatga tgatgaagta cagggaccag agagccggaa agatttccga acggctggtg    780
atcacttcgg aaatgatcga aaacatccag tcagtgaagg cctactgctg ggaagaggcc    840
atggaaaaga tgattgaaaa cctccggcaa accgagctga agctgacccg caaggccgct    900
tacgtgcgct atttcaactc gtccgctttc ttcttctccg ggttcttcgt ggtgtttctc    960
tccgtgctcc cctacgccct gattaaggga atcatcctca ggaagatctt caccaccatt   1020
tccttctgta tcgtgctccg catggccgtg accggcagt tcccatgggc cgtgcagact   1080
tggtacgact ccctgggagc cattaacaag atccaggact tccttcaaaa gcaggagtac   1140
aagaccctcg agtacaacct gactactacc gaggtcgtga tggaaaacgt caccgccttt   1200
tgggaggagg gatttggcga actgttcgag aaggccaagc agaacaacaa caaccgcaag   1260
acctcgaacg gtgacgactc cctcttcttt tcaaacttca gcctgctcgg gacgcccgtg   1320
ctgaaggaca ttaacttcaa gatcgaaaga ggacagctcc tggcggtggc cggatcgacc   1380
ggagccggaa agacttccct gctgatggtg atcatgggag agcttgaacc tagcgaggga   1440
aagatcaagc actccggccg catcagcttc tgtagccagt tttcctggat catgcccgga   1500
accattaagg aaaacatcat cttcggcgtg tcctacgatg aataccgcta ccggtccgtg   1560
atcaaagcct gccagctgga agaggatatt tcaaagttcg cggagaaaga taacatcgtg   1620
```

-continued

```
ctgggcgaag ggggtattac cttgtcgggg ggccagcggg ctagaatctc gctggccaga      1680
gccgtgtata aggacgccga cctgtatctc ctggactccc ccttcggata cctggacgtc      1740
ctgaccgaaa aggagatctt cgaatcgtgc gtgtgcaagc tgatggctaa caagactcgc      1800
atcctcgtga cctccaaaat ggagcacctg aagaaggcag acaagattct gattctgcat      1860 gagggggtcct cctactttta cggcaccttc tcggagttgc agaacttgca gcccgacttc      1920
tcatcgaagc tgatgggttg cgacagcttc gaccagttct ccgccgaaag aaggaactcg      1980
atcctgacgg aaaccttgca ccgcttctct ttggaaggcg acgccctgt gtcatggacc      2040 gagactaaga agcagagctt caagcagacc ggggaattcg gcgaaaagag gaagaacagc      2100
atcttgaacc ccattaactc catccgcaag ttctcaatcg tgcaaaagac gccactgcag      2160
atgaacggca ttgaggagga ctccgacgaa ccccttgaga ggcgcctgtc cctggtgccg      2220
gacagcgagc agggagaagc catcctgcct cggatttccg tgatctccac tggtccgacg      2280
ctccaagccc ggcggcggca gtccgtgctg aacctgatga cccacagcgt gaaccagggc      2340
caaaacattc accgcaagac taccgcatcc acccggaaag tgtccctggc acctcaagcg      2400
aatcttaccg agctcgacat ctactcccgg agactgtcgc aggaaaccgg gctcgaaatt      2460
tccgaagaaa tcaacgagga ggatctgaaa gagtgcttct tcgacgatat ggagtcgata      2520
cccgccgtga cgacttggaa cacttatctg cggtacatca ctgtgcacaa gtcattgatc      2580
ttcgtgctga tttggtgcct ggtgattttc ctggccgagg tcgcggcctc actggtggtg      2640
ctctggctgt tgggaaacac gcctctgcaa gacaagggaa actccacgca ctcgagaaac      2700
aacagctatg ccgtgattat cacttccacc tcctcttatt acgtgttcta catctacgtc      2760
ggagtggcgg ataccctgct cgcgatgggt ttcttcagag gactgccgct ggtccacacc      2820
ttgatcaccg tcagcaagat tcttcaccac aagatgttgc atagcgtgct gcaggccccc      2880
atgtccaccc tcaacactct gaaggccgga ggcattctga acagattctc caaggacatc      2940
gctatcctgg acgatctcct gccgcttacc atctttgact tcatccagct gctgctgatc      3000
gtgattggag caatcgcagt ggtggcggtg ctgcagcctt acattttcgt ggccactgtg      3060
ccggtcattg tggcgttcat catgctgcgg gcctacttcc tccaaaccag ccagcagctg      3120
aagcaactgg aatccgaggg acgatccccc atcttcactc accttgtgac gtcgttgaag      3180
ggactgtgga ccctccgggc tttcggacgg cagccctact tcgaaaccct cttccacaag      3240
gccctgaacc tccacaccgc caattggttc ctgtacctgt ccaccctgcg gtggttccag      3300
atgcgcatcg agatgatttt cgtcatcttc ttcatcgcgg tcacattcat cagcatcctg      3360
actaccggag agggagaggg acgggtcgga ataatcctga ccctcgccat gaacattatg      3420
agcaccctgc agtgggcagt gaacagctcg atcgacgtgg acagcctgat gcgaagcgtc      3480
agccgcgtgt tcaagttcat cgacatgcct actgagggaa aacccactaa gtccactaag      3540
ccctacaaaa atggccagct gagcaaggtc atgatcatcg aaaactccca cgtgaagaag      3600
gacgatattt ggccctccgg aggtcaaatg accgtgaagg acctgaccgc aaagtacacc      3660
gagggaggaa acgccattct cgaaaacatc agcttctcca tttcgccggg acagcgggtc      3720
ggccttctcg ggcggaccgg ttccgggaag tcaactctgc tgtcggcttt cctccggctg      3780
ctgaataccg aggggaaat ccaaattgac ggccgtgtct tgggattccat tactctgcag      3840 cagtggcgga aggccttcgg cgtgatcccc cagaaggtgt tcatcttctc gggtaccttc      3900
cggaagaacc tggatcctta cgagcagtgg agcgaccaag aaatctggaa ggtcgccgac      3960
```

-continued

```
gaggtcggcc tgcgctccgt gattgaacaa tttcctggaa agctggactt cgtgctcgtc    4020
gacgggggat gtgtcctgtc gcacggacat aagcagctca tgtgcctcgc acggtccgtg    4080
ctctccaagg ccaagattct gctgctggac gaaccttcgg cccacctgga tccggtcacc    4140
taccagatca tcaggaggac cctgaagcag gcctttgccg attgcaccgt gattctctgc    4200
gagcaccgca tcgaggccat gctggagtgc cagcagttcc tggtcatcga ggagaacaag    4260
gtccgccaat acgactccat tcaaaagctc ctcaacgagc ggtcgctgtt cagacaagct    4320
atttcaccgt ccgatagagt gaagctcttc ccgcatcgga acagctcaaa gtgcaaatcg    4380
aagccgcaga tcgcagcctt gaaggaagag actgaggaag aggtgcagga cacccggctt    4440
taa                                                                   4443
```

<210> SEQ ID NO 16
<211> LENGTH: 4443
<212> TYPE: DNA
<213> ORGANISM: Artificial Sequence
<220> FEATURE:
<223> OTHER INFORMATION: Synthetic polynucleotide

<400> SEQUENCE: 16

```
atgcagcggt ccccgctcga aaaggccagt gtcgtgtcca aactcttctt ctcatggact      60
cggcctatcc ttagaaaggg gtatcggcag aggcttgagt tgtctgacat ctaccagatc     120
ccctcggtag attcggcgga taacctctcg gagaagctcg aacgggaatg ggaccgcgaa     180
ctcgcgtcta agaaaaaccc gaagctcatc aacgcactga gaaggtgctt cttctggcgg     240
ttcatgttct acggtatctt cttgtatctc ggggaggtca caaaagcagt ccaacccctg     300
ttgttgggtc gcattatcgc ctcgtacgac cccgataaca agaagaacg gagcatcgcg       360 atctacctcg ggatcggact gtgtttgctt ttcatcgtca gaacactttt gttgcatcca     420
gcaatcttcg gcctccatca catcggtatg cagatgcgaa tcgctatgtt tagcttgatc     480
tacaaaaaga cactgaaact ctcgtcgcgg gtgttggata agatttccat cggtcagttg     540
gtgtccctgc ttagtaataa cctcaacaaa ttcgatgagg gactggcgct ggcacatttc     600
gtgtggattc ccccgttgca agtcgccctt ttgatgggcc ttatttggga actcttgcag     660
gcatctgcct tttgtggcct gggatttctg attgtgttgg cattgtttca ggctgggctt     720
gggcggatga tgatgaagta tcgcgaccag agagcgggta aaatctcgga aagactcgtc     780
atcacttcgg aaatgatcga aaacatccag tcggtcaaag cctattgctg ggaagaagct     840
atggagaaga tgattgaaaa cctccgccaa actgagctga aactgacccg caaggcggcg     900
tatgtccggt atttcaattc gtcagcgttc ttcttttccg ggttcttcgt tgtctttctc     960
tcggttttgc cttatgcctt gattaagggg attatcctcc gcaagatttt caccacgatt    1020
tcgttctgca ttgtattgcg catggcagtg acacggcaat ttccgtgggc cgtgcagaca    1080
tggtatgact cgcttggagc gatcaacaaa atccaagact tcttgcaaaa gcaagagtac    1140
aagaccctgg agtacaatct tactactacg gaggtagtaa tggagaatgt gacggctttt    1200
tgggaagagg gttttggaga gctcttcgag aaagcaaagc agaataacaa caaccgcaag    1260
acctcaaatg gggacgattc cctgtttttc tcgaacttct ccctgctcgg aacacccgtg    1320
ttgaaggaca tcaatttcaa gattgagagg ggacagcttc tcgcggtagc gggaagcact    1380
ggtgcgggaa aaactagcct cttgatggtg attatggggg agcttgagcc cagcgagggg    1440
aagattaaac actccgggcg tatctcattc tgtagccagt tttcatggat catgcccgga    1500
accattaaag agaacatcat tttcggagta tcctatgatg agtaccgata cagatcggtc    1560
```

-continued

```
attaaggcgt gccagttgga agaggacatt tctaagttcg ccgagaagga taacatcgtc      1620
ttgggagaag ggggtattac attgtcggga gggcagcgag cgcggatcag cctcgcgaga      1680
gcggtataca aagatgcaga tttgtacctg ctcgattcac cgtttggata cctcgacgta      1740
ttgacagaaa aagaaatctt cgagtcgtgc gtgtgtaaac ttatggctaa taagacgaga      1800
atcctggtga catcaaaaat ggaacacctt aagaaggcgg acaagatcct gatcctccac      1860
gaaggatcgt cctactttta cggcactttc tcagagttgc aaaacttgca gccggacttc      1920
tcaagcaaac tcatggggtg tgactcattc gaccagttca gcgcggaacg gcggaactcg      1980
atcttgacgg aaacgctgca ccgattctcg cttgagggtg atgccccggt atcgtggacc      2040
gagacaaaga agcagtcgtt taagcagaca ggagaatttg gtgagaaaag aaagaacagt      2100
atcttgaatc ctattaactc aattcgcaag ttctcaatcg tccagaaaac tccactgcag      2160
atgaatggaa ttgaagagga ttcggacgaa cccctggagc gcaggcttag cctcgtgccg      2220
gattcagagc aaggggaggc cattcttccc cggatttcgg tgatttcaac cggacctaca      2280
cttcaggcga ggcgaaggca atccgtgctc aacctcatga cgcattcggt aaaccagggg      2340
caaaacattc accgcaaaac gacggcctca acgagaaaag tgtcacttgc accccaggcg      2400
aatttgactg aactcgacat ctacagccgt aggctttcgc aagaaaccgg acttgagatc      2460
agcgaagaaa tcaatgaaga agatttgaaa gagtgtttct ttgatgacat ggaatcaatc      2520
ccagcggtga caacgtggaa cacatacttg cgttacatca cggtgcacaa gtccttgatt      2580
ttcgtcctca tttggtgcct cgtgatcttt ctcgctgagg tcgcagcgtc acttgtggtc      2640
ctctggctgc ttggtaatac gcccttgcaa gacaaaggca attctacaca ctcaagaaac      2700
aattcctatg ccgtgattat cacttctaca agctcgtatt acgtgtttta catctacgta      2760
ggagtggccg acactctgct cgcgatgggt ttcttccgag gactcccact cgttcacacg      2820
cttatcactg tctccaagat tctccaccat aagatgcttc atagcgtact gcaggctccc      2880
atgtccacct tgaatacgct caaggcggga ggtattttga atcgcttctc aaaagatatt      2940
gcaattttgg atgaccttct gcccctgacg atcttcgact tcatccagtt gttgctgatc      3000
gtgattgggg ctattgcagt agtcgctgtc ctccagcctt acattttttgt cgcgaccgtt      3060 ccggtgatcg tggcgtttat catgctgcgg gcctatttct tgcagacgtc acagcagctt      3120
aagcaactgg agtctgaagg gaggtcgcct atctttacgc atcttgtgac cagtttgaag      3180
ggattgtgga cgttgcgcgc ctttggcagg cagccctact ttgaaacact gttccacaaa      3240
gcgctgaatc tccatacggc aaattggttt ttgtatttga gtaccctccg atggtttcag      3300
atgcgcattg agatgatttt tgtgatcttc tttatcgcgg tgactttttat ctccatcttg      3360 accacgggag agggcgaggg acgggtcggt attatcctga cactcgccat gaacattatg      3420
agcactttgc agtgggcagt gaacagctcg attgatgtgg atagcctgat gaggtccgtt      3480
tcgagggtct ttaagttcat cgacatgccg acggagggaa agcccacaaa aagtacgaaa      3540
ccctataaga atgggcaatt gagtaaggta atgatcatcg agaacagtca cgtgaagaag      3600
gatgacatct ggcctagcgg gggtcagatg accgtgaagg acctgacggc aaaatacacc      3660
gagggaggga acgcaatcct tgaaaacatc tcgttcagca ttagccccgg tcagcgtgtg      3720
gggttgctcg ggaggaccgg gtcaggaaaa tcgacgttgc tgtcggcctt cttgagactt      3780
ctgaatacag agggtgagat ccagatcgac ggcgtttcgt gggatagcat caccttgcag      3840
cagtggcgga aagcgtttgg agtaatcccc caaaaggtct ttatctttag cggaaccttc      3900
```

-continued

```
cgaaagaatc tcgatcctta tgaacagtgg tcagatcaag agatttggaa agtcgcggac    3960
gaggttggcc ttcggagtgt aatcgagcag tttccgggaa aactcgactt tgtccttgta    4020
gatgggggat gcgtcctgtc gcatgggcac aagcagctca tgtgcctggc gcgatccgtc    4080
ctctctaaag cgaaaattct tctcttggat gaaccttcgg cccatctgga cccggtaacg    4140
tatcagatca tcagaaggac acttaagcag gcgtttgccg actgcacggt gattctctgt    4200
gagcatcgta tcgaggccat gctcgaatgc cagcaatttc ttgtcatcga agagaataag    4260
gtccgccagt acgactccat ccagaagctg cttaatgaga gatcattgtt ccggcaggcg    4320
atttcaccat ccgatagggt gaaacttttt ccacacagaa attcgtcgaa gtgcaagtcc    4380
aaaccgcaga tcgcggcctt gaagaagag actgaagaag aagttcaaga cacgcgtctt    4440
taa                                                                  4443
```

```
<210> SEQ ID NO 17
<211> LENGTH: 874
<212> TYPE: PRT
<213> ORGANISM: Artificial Sequence
<220> FEATURE:
<223> OTHER INFORMATION: Synthetic polypeptide

<400> SEQUENCE: 17

Met Gln Asp Leu His Ala Ile Gln Leu Gln Leu Glu Glu Glu Met Phe
1               5                   10                  15

Asn Gly Gly Ile Arg Arg Phe Glu Ala Asp Gln Gln Arg Gln Ile Ala
                20                  25                  30

Ala Gly Ser Glu Ser Asp Thr Ala Trp Asn Arg Arg Leu Leu Ser Glu
            35                  40                  45

Leu Ile Ala Pro Met Ala Glu Gly Ile Gln Ala Tyr Lys Glu Glu Tyr
        50                  55                  60

Glu Gly Lys Lys Gly Arg Ala Pro Arg Ala Leu Ala Phe Leu Gln Cys
65                  70                  75                  80

Val Glu Asn Glu Val Ala Ala Tyr Ile Thr Met Lys Val Val Met Asp
                85                  90                  95

Met Leu Asn Thr Asp Ala Thr Leu Gln Ala Ile Ala Met Ser Val Ala
                100                 105                 110

Glu Arg Ile Glu Asp Gln Val Arg Phe Ser Lys Leu Glu Gly His Ala
            115                 120                 125

Ala Lys Tyr Phe Glu Lys Val Lys Lys Ser Leu Lys Ala Ser Arg Thr
        130                 135                 140

Lys Ser Tyr Arg His Ala His Asn Val Ala Val Val Ala Glu Lys Ser
145                 150                 155                 160

Val Ala Glu Lys Asp Ala Asp Phe Asp Arg Trp Glu Ala Trp Pro Lys
                165                 170                 175

Glu Thr Gln Leu Gln Ile Gly Thr Thr Leu Leu Glu Ile Leu Glu Gly
            180                 185                 190

Ser Val Phe Tyr Asn Gly Glu Pro Val Phe Met Arg Ala Met Arg Thr
        195                 200                 205

Tyr Gly Gly Lys Thr Ile Tyr Tyr Leu Gln Thr Ser Glu Ser Val Gly
        210                 215                 220

Gln Trp Ile Ser Ala Phe Lys Glu His Val Ala Gln Leu Ser Pro Ala
225                 230                 235                 240

Tyr Ala Pro Cys Val Ile Pro Pro Arg Pro Trp Arg Thr Pro Phe Asn
                245                 250                 255

Gly Gly Phe His Thr Glu Lys Val Ala Ser Arg Ile Arg Leu Val Lys
```

-continued

```
              260                265                270

Gly Asn Arg Glu His Val Arg Lys Leu Thr Gln Lys Gln Met Pro Lys
          275                280                285

Val Tyr Lys Ala Ile Asn Ala Leu Gln Asn Thr Gln Trp Gln Ile Asn
          290                295                300

Lys Asp Val Leu Ala Val Ile Glu Glu Val Ile Arg Leu Asp Leu Gly
305                310                315                320

Tyr Gly Val Pro Ser Phe Lys Pro Leu Ile Asp Lys Glu Asn Lys Pro
              325                330                335

Ala Asn Pro Val Pro Val Glu Phe Gln His Leu Arg Gly Arg Glu Leu
              340                345                350

Lys Glu Met Leu Ser Pro Glu Gln Trp Gln Gln Phe Ile Asn Trp Lys
          355                360                365

Gly Glu Cys Ala Arg Leu Tyr Thr Ala Glu Thr Lys Arg Gly Ser Lys
          370                375                380

Ser Ala Ala Val Val Arg Met Val Gly Gln Ala Arg Lys Tyr Ser Ala
385                390                395                400

Phe Glu Ser Ile Tyr Phe Val Tyr Ala Met Asp Ser Arg Ser Arg Val
              405                410                415

Tyr Val Gln Ser Ser Thr Leu Ser Pro Gln Ser Asn Asp Leu Gly Lys
          420                425                430

Ala Leu Leu Arg Phe Thr Glu Gly Arg Pro Val Asn Gly Val Glu Ala
          435                440                445

Leu Lys Trp Phe Cys Ile Asn Gly Ala Asn Leu Trp Gly Trp Asp Lys
          450                455                460

Lys Thr Phe Asp Val Arg Val Ser Asn Val Leu Asp Glu Glu Phe Gln
465                470                475                480

Asp Met Cys Arg Asp Ile Ala Ala Asp Pro Leu Thr Phe Thr Gln Trp
              485                490                495

Ala Lys Ala Asp Ala Pro Tyr Glu Phe Leu Ala Trp Cys Phe Glu Tyr
              500                505                510

Ala Gln Tyr Leu Asp Leu Val Asp Glu Gly Arg Ala Asp Glu Phe Arg
          515                520                525

Thr His Leu Pro Val His Gln Asp Gly Ser Cys Ser Gly Ile Gln His
          530                535                540

Tyr Ser Ala Met Leu Arg Asp Glu Val Gly Ala Lys Ala Val Asn Leu
545                550                555                560

Lys Pro Ser Asp Ala Pro Gln Asp Ile Tyr Gly Ala Val Ala Gln Val
              565                570                575

Val Ile Lys Lys Asn Ala Leu Tyr Met Asp Ala Asp Asp Ala Thr Thr
              580                585                590

Phe Thr Ser Gly Ser Val Thr Leu Ser Gly Thr Glu Leu Arg Ala Met
          595                600                605

Ala Ser Ala Trp Asp Ser Ile Gly Ile Thr Arg Ser Leu Thr Lys Lys
          610                615                620

Pro Val Met Thr Leu Pro Tyr Gly Ser Thr Arg Leu Thr Cys Arg Glu
625                630                635                640

Ser Val Ile Asp Tyr Ile Val Asp Leu Glu Glu Lys Glu Ala Gln Lys
              645                650                655

Ala Val Ala Glu Gly Arg Thr Ala Asn Lys Val His Pro Phe Glu Asp
              660                665                670

Asp Arg Gln Asp Tyr Leu Thr Pro Gly Ala Ala Tyr Asn Tyr Met Thr
          675                680                685
```

-continued

```
Ala Leu Ile Trp Pro Ser Ile Ser Glu Val Val Lys Ala Pro Ile Val
    690                 695             700

Ala Met Lys Met Ile Arg Gln Leu Ala Arg Phe Ala Ala Lys Arg Asn
705                 710             715                         720

Glu Gly Leu Met Tyr Thr Leu Pro Thr Gly Phe Ile Leu Glu Gln Lys
                725             730                 735

Ile Met Ala Thr Glu Met Leu Arg Val Arg Thr Cys Leu Met Gly Asp
                740             745             750

Ile Lys Met Ser Leu Gln Val Glu Thr Asp Ile Val Asp Glu Ala Ala
                755             760             765

Met Met Gly Ala Ala Ala Pro Asn Phe Val His Gly His Asp Ala Ser
    770             775             780

His Leu Ile Leu Thr Val Cys Glu Leu Val Asp Lys Gly Val Thr Ser
785             790             795                         800

Ile Ala Val Ile His Asp Ser Phe Gly Thr His Ala Asp Asn Thr Leu
                805             810                 815

Thr Leu Arg Val Ala Leu Lys Gly Gln Met Val Ala Met Tyr Ile Asp
                820             825             830

Gly Asn Ala Leu Gln Lys Leu Leu Glu Glu His Glu Val Arg Trp Met
            835             840             845

Val Asp Thr Gly Ile Glu Val Pro Glu Gln Gly Glu Phe Asp Leu Asn
    850             855             860

Glu Ile Met Asp Ser Glu Tyr Val Phe Ala
865             870
```